(12) United States Patent
Rajaiah et al.

(10) Patent No.: US 12,337,044 B2
(45) Date of Patent: *Jun. 24, 2025

(54) ELECTROMAGNETIC RADIATION AND MULTI-PHASE ORAL COMPOSITIONS FOR ORAL CARE

(71) Applicant: The Procter & Gamble Company, Cincinnati, OH (US)

(72) Inventors: Jayanth Rajaiah, Loveland, OH (US); Paul Albert Sagel, Maineville, OH (US); Franco Silva Medeiros, Loveland, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/432,157

(22) Filed: Feb. 5, 2024

(65) Prior Publication Data

US 2024/0173217 A1   May 30, 2024

Related U.S. Application Data

(63) Continuation of application No. 17/991,885, filed on Nov. 22, 2022, now Pat. No. 11,938,206, which is a
(Continued)

(51) Int. Cl.
*A61K 8/06* (2006.01)
*A61C 19/06* (2006.01)
(Continued)

(52) U.S. Cl.
CPC ............ *A61K 8/064* (2013.01); *A61C 19/066* (2013.01); *A61K 8/0216* (2013.01); *A61K 8/062* (2013.01);
(Continued)

(58) Field of Classification Search
CPC ........ A61K 8/064; A61K 8/345; A61K 8/062; A61K 8/0216; A61K 8/92; A61K 8/86;
(Continued)

(56) References Cited

U.S. PATENT DOCUMENTS 2,798,053 A   7/1957   Brown
2,835,628 A   5/1958   Saffir
(Continued)

FOREIGN PATENT DOCUMENTS

CN   1345223 A   4/2002
CN   1893915 A   1/2007
(Continued)

OTHER PUBLICATIONS

PCT Search Report and Written Opinion for PCT/US2017/057864 dated Dec. 19, 2017, 12 pages.
(Continued)

*Primary Examiner* — Matthew M Nelson
(74) *Attorney, Agent, or Firm* — John G. Powell; Elizabeth A. Conklin

(57) ABSTRACT

A kit includes a multi-phase oral composition for whitening teeth and a delivery carrier. The multi-phase oral composition for whitening teeth includes from about 0.002% to about 30%, by weight of the multi-phase oral composition, of a discontinuous aqueous phase having up to 10%, by weight of the multi-phase oral composition, of a bleaching agent and a continuous hydrophobic phase having at least about 50%, by weight of the multi-phase oral composition, of petrolatum.

20 Claims, 7 Drawing Sheets

Related U.S. Application Data continuation of application No. 17/699,272, filed on Mar. 21, 2022, now Pat. No. 11,878,068, which is a continuation of application No. 15/790,903, filed on Oct. 23, 2017, now Pat. No. 11,278,476.

(60) Provisional application No. 62/413,214, filed on Oct. 26, 2016, provisional application No. 62/413,237, filed on Oct. 26, 2016, provisional application No. 62/413,222, filed on Oct. 26, 2016, provisional application No. 62/413,229, filed on Oct. 26, 2016, provisional application No. 62/413,189, filed on Oct. 26, 2016, provisional application No. 62/413,200, filed on Oct. 26, 2016, provisional application No. 62/413,205, filed on Oct. 26, 2016.

(51) Int. Cl.
| | | |
|---|---|---|
| *A61K 8/02* | (2006.01) | |
| *A61K 8/22* | (2006.01) | |
| *A61K 8/31* | (2006.01) | |
| *A61K 8/34* | (2006.01) | |
| *A61K 8/81* | (2006.01) | |
| *A61K 8/86* | (2006.01) | |
| *A61K 8/92* | (2006.01) | |
| *A61N 5/06* | (2006.01) | |
| *A61Q 11/00* | (2006.01) | |
| *A61Q 11/02* | (2006.01) | |

(52) U.S. Cl.
CPC ............... *A61K 8/22* (2013.01); *A61K 8/31* (2013.01); *A61K 8/345* (2013.01); *A61K 8/8111* (2013.01); *A61K 8/86* (2013.01); *A61K 8/92* (2013.01); *A61N 5/0603* (2013.01); *A61N 5/062* (2013.01); *A61Q 11/00* (2013.01); *A61Q 11/02* (2013.01); *A61K 2800/42* (2013.01); *A61K 2800/81* (2013.01); *A61K 2800/87* (2013.01); *A61K 2800/884* (2013.01); *A61K 2800/92* (2013.01); *A61N 2005/0606* (2013.01); *A61N 2005/0663* (2013.01)

(58) Field of Classification Search
CPC .......... A61K 8/22; A61K 8/8111; A61K 8/31; A61K 2800/92; A61K 2800/42; A61K 2800/87; A61K 2800/884; A61K 2800/81; A61N 5/0603; A61N 5/062; A61N 2005/0663; A61N 2005/0606; A61C 19/066; A61Q 11/00; A61Q 11/02
USPC .......................................................... 433/29
See application file for complete search history.

(56) References Cited

U.S. PATENT DOCUMENTS

| | | | |
|---|---|---|---|
| 3,506,720 | A | 4/1970 | Bindler et al. |
| 3,959,458 | A | 5/1976 | Agricola et al. |
| 3,988,433 | A | 10/1976 | Benedict |
| 4,013,770 | A | 3/1977 | Bharucha |
| 4,051,234 | A | 9/1977 | Gieske et al. |
| 5,016,784 | A | 5/1991 | Batson |
| 5,024,701 | A | 6/1991 | Desmarais |
| 5,484,542 | A | 1/1996 | Cahoon |
| 5,512,278 | A | 4/1996 | Mundschenk |
| 5,766,011 | A | 6/1998 | Sibner |
| 5,879,691 | A | 3/1999 | Sagel et al. |
| 5,891,453 | A | 4/1999 | Sagel et al. |
| 5,894,017 | A | 4/1999 | Sagel et al. |
| 5,989,569 | A | 11/1999 | Dirksing et al. |
| 6,040,160 | A | 3/2000 | Kojima et al. |
| 6,045,811 | A | 4/2000 | Dirksing et al. |
| 6,096,328 | A | 8/2000 | Sagel et al. |
| 6,136,297 | A | 10/2000 | Sagel |
| 6,509,007 | B2 | 1/2003 | Rajaiah |
| 7,025,950 | B2 | 4/2006 | Majeti |
| 8,540,971 | B2 | 9/2013 | Zaidel et al. |
| 8,623,388 | B2 | 1/2014 | Rajaiah |
| 8,945,519 | B2 | 2/2015 | Sharma |
| 9,138,387 | B2 | 9/2015 | Shiba |
| 10,688,026 | B2 | 6/2020 | Latta |
| 10,849,729 | B2 | 12/2020 | Sagel et al. |
| 11,123,270 | B2 | 9/2021 | Rajaiah et al. |
| 11,147,753 | B2 * | 10/2021 | Rajaiah ................. A61K 8/064 |
| 11,253,442 | B2 * | 2/2022 | Rajaiah ................. A61K 8/0216 |
| 11,259,998 | B2 * | 3/2022 | Rajaiah ................. A61Q 11/00 |
| 11,266,581 | B2 * | 3/2022 | Rajaiah ................. A61K 8/064 |
| 11,278,476 | B2 * | 3/2022 | Rajaiah ................. A61N 5/062 |
| 11,559,473 | B2 | 1/2023 | Sagel et al. |
| 11,607,300 | B2 | 3/2023 | Sagel et al. |
| 11,878,068 | B2 | 1/2024 | Rajaiah |
| 11,938,206 | B2 | 3/2024 | Rajaiah |
| 2002/0006388 | A1 | 1/2002 | Sagel et al. |
| 2002/0176827 | A1 | 11/2002 | Rajaiah et al. |
| 2003/0072722 | A1 | 4/2003 | Nathoo |
| 2003/0113276 | A1 | 6/2003 | Rajaiah et al. |
| 2005/0008584 | A1 | 1/2005 | Montgomery |
| 2005/0036958 | A1 | 2/2005 | Feng |
| 2005/0063923 | A1 | 3/2005 | Prencipe |
| 2005/0064371 | A1 | 3/2005 | Soukos |
| 2005/0137109 | A1 * | 6/2005 | Quan .................. A61K 8/0208 |
| | | | 510/303 |
| 2005/0137110 | A1 | 6/2005 | Scott |
| 2005/0143274 | A1 | 6/2005 | Ghosh |
| 2006/0019214 | A1 | 1/2006 | Lawrence |
| 2006/0204453 | A1 | 9/2006 | Giniger |
| 2007/0054233 | A1 | 3/2007 | Rizoiu et al. |
| 2007/0054235 | A1 | 3/2007 | Rizoui et al. |
| 2007/0054236 | A1 | 3/2007 | Rizoiu et al. |
| 2007/0059660 | A1 | 3/2007 | Rizoiu et al. |
| 2007/0151480 | A1 | 7/2007 | Bloom |
| 2007/0280894 | A1 * | 12/2007 | Romano .................. A61K 8/90 |
| | | | 424/53 |
| 2007/0292459 | A1 | 12/2007 | Cooper |
| 2008/0274067 | A1 | 11/2008 | Chaffer |
| 2009/0029311 | A1 | 1/2009 | Chan |
| 2009/0081136 | A1 | 3/2009 | Sharma |
| 2009/0181071 | A1 | 7/2009 | St. John |
| 2009/0208543 | A1 | 8/2009 | Nathoo |
| 2010/0196857 | A1 | 8/2010 | Yarborough |
| 2011/0306004 | A1 | 12/2011 | Sagel |
| 2012/0037038 | A1 | 2/2012 | Rajaiah |
| 2012/0134936 | A1 * | 5/2012 | Kwak .................. A61K 8/064 |
| | | | 424/53 |
| 2013/0149262 | A1 | 6/2013 | Sharma |
| 2013/0295525 | A1 | 11/2013 | Sagel |
| 2014/0178443 | A1 | 6/2014 | Sagel et al. |
| 2014/0335028 | A1 | 11/2014 | Prencipe et al. |
| 2015/0037266 | A1 | 2/2015 | Boyd et al. |
| 2015/0238399 | A1 | 8/2015 | Spaid |
| 2016/0074290 | A1 | 3/2016 | Sagel et al. |
| 2016/0279039 | A1 * | 9/2016 | Giniger .................. A61K 8/046 |
| 2017/0172864 | A1 * | 6/2017 | Evans .................... A61Q 11/00 |
| 2017/0239029 | A1 | 8/2017 | Sagel |
| 2018/0133119 | A1 | 5/2018 | Rajaiah et al. |
| 2018/0133120 | A1 | 5/2018 | Rajaiah et al. |
| 2018/0133121 | A1 | 5/2018 | Rajaiah et al. |
| 2018/0133122 | A1 | 5/2018 | Rajaiah et al. |
| 2018/0133123 | A1 | 5/2018 | Rajaiah |
| 2018/0133128 | A1 | 5/2018 | Rajaiah et al. |
| 2018/0133502 | A1 | 5/2018 | Rajaiah et al. |
| 2018/0140516 | A1 | 5/2018 | Rajaiah et al. |
| 2018/0243178 | A1 * | 8/2018 | Nesta .................... A61K 8/891 |
| 2018/0280259 | A1 * | 10/2018 | De Laat .................. A61K 8/90 |
| 2022/0040061 | A1 | 2/2022 | Rajaiah et al. |
| 2022/0280397 | A1 | 9/2022 | Rajaiah et al. |
| 2023/0091576 | A1 | 3/2023 | Rajaiah et al. |

FOREIGN PATENT DOCUMENTS

| | | |
|---|---|---|
| CN | 1893917 A | 1/2007 |
| CN | 1933800 A | 3/2007 |

(56) References Cited

FOREIGN PATENT DOCUMENTS

| | | | | |
|---|---|---|---|---|
| CN | 101019812 | A | 8/2007 | |
| CN | 200984244 | Y | 12/2007 | |
| CN | 101663017 | A | 3/2010 | |
| CN | 102614090 | A | 8/2012 | |
| CN | 102961261 | A | 3/2013 | |
| CN | 105640787 | A | 6/2016 | |
| DE | 102007013040 | A1 | 9/2008 | |
| EP | 0251591 | A1 | 7/1988 | |
| EP | 1696866 | B1 | 9/2006 | |
| EP | 3315119 | A1 * | 5/2018 | ............ A61K 8/064 |
| GB | 1492660 | A | 11/1977 | |
| JP | 2009126819 | A | 6/2009 | |
| JP | 2016017072 | A | 7/2014 | |
| JP | 2014152166 | A | 8/2014 | |
| JP | 2015117217 | A | 6/2015 | |
| JP | 2015528505 | A | 9/2015 | |
| WO | 03015656 | A2 | 2/2003 | |
| WO | 2005058267 | A1 | 6/2005 | |
| WO | 2006138550 | A1 | 9/2008 | |
| WO | 2010098761 | A1 | 9/2010 | |
| WO | WO-2013093743 | A1 * | 6/2013 | ........... A61C 19/066 |
| WO | 201783570 | A1 | 5/2017 | |

OTHER PUBLICATIONS

All Office Actions; U.S. Appl. No. 15/790,702, filed Oct. 23, 2017.
All Office Actions; U.S. Appl. No. 15/790,820, filed Oct. 23, 2017.
All Office Actions; U.S. Appl. No. 15/790,877, filed Oct. 23, 2017.
All Office Actions; U.S. Appl. No. 15/790,903, filed Oct. 23, 2017.
All Office Actions; U.S. Appl. No. 15/790,740, filed Oct. 23, 2017.
All Office Actions; U.S. Appl. No. 15/790,788br, filed Oct. 23, 2017.
All Office Actions; U.S. Appl. No. 15/790,951, filed Oct. 23, 2017.
All Office Actions; U.S. Appl. No. 17/503,762, filed Oct. 18, 2021.
All Office Actions; U.S. Appl. No. 17/503,553, filed Oct. 18, 2021.
All Office Actions; U.S. Appl. No. 17/529,716, filed Nov. 18, 2021.
All Office Actions; U.S. Appl. No. 17/529,681, filed Nov. 18, 2021.
All Office Actions; U.S. Appl. No. 17/699,272, filed Mar. 21, 2022.
All Office Actions; U.S. Appl. No. 17/991,885, filed Nov. 22, 2022.
Chemistry and Technology of Silicones, Walter Noll, Academic Press Inc, (Harcourt Brue Javanovich, Publishers, New York), 1968, pp. 282-287 and 409-426.
Definition of "Matrix" by Online Merriam-Webster Dictionary; Dated Jun. 3, 2020; 9 pages.
E. Dickeinson, "Emulsions and droplet size control." Chapter 7, pp. 191-216 of book entitled: Control Particle, Droplet and Bubble Formation, Edited by David J. Bwdlock, 1994 (Year: 1994).
Encyclopedia of Polymer Science and Engineering, vol. 15, 2nd ed., pp. 204 308 Silicones, 1989.
Kirk-Othmer, Encyclopedia of Chemical Technology, Fourth Edition, vol. 21, Jan. 6, 1997, pp. 207-218.
Kostansek, Edward, and Updated by Staff. "Emulsions." Kirk-Othmer Encyclopedia of Chemicalpp. 1-24.
Machinery Lubrication, "A Better Way to Test Grease Consistency." www.machinerylubrication.com/Read/30271/grease-consistency, Year 2015, 18 pages.
Marshall et al. "Hydrogen Peroxide: A Review of Its Use in Dentistry", In Journal of Periodontology, vol. 66, Issue 9 (Year: 1995), 8 Pages.
Mishra, et al., "Microemulsions: as drug delivery system." In Journal of Scientific Innovative Research 3(4), 2014, pp. 467-474.
Penreco, "Intelligent Gel Technology Product Specifications: Versagel M." www.penreco.com, Jun. 2016, 2 pages.
www.fao.org, "petroleum jelly—FAO". Prepared at the 51st JECFA (1998), published in FNP.
All Office Actions; U.S. Appl. No. 18/906,271, filed Oct. 4, 2024.
U.S. Appl. No. 18/906,271, filed Oct. 4, 2024, Jayanth Rajaiah et al.

* cited by examiner

ELECTROMAGNETIC RADIATION AND MULTI-PHASE ORAL COMPOSITIONS FOR ORAL CARE

TECHNICAL FIELD

The present technology relates to multi-phase oral compositions used for whitening teeth and related kits and methods.

BACKGROUND

Currently in the marketplace are dental products by which various cosmetic and/or therapeutic actives are delivered to teeth and the oral cavity. Examples of such products include: brushing aids, such as dentifrice products for delivery of oral care actives for example polyphosphates or fluorides; mouthwashes containing breath fresheners or antibacterial actives; and whitening strips for the delivery of bleaching actives to the teeth. In particular, the use of a dental strip has been recognized as a convenient and inexpensive way to deliver cosmetic and therapeutic benefits to the teeth and mucosal surfaces of the oral cavity; for example, dental whitening strips, where a whitening composition is applied to a strip and thereafter applied to the teeth to achieve sustained contact between the teeth and the whitening composition.

Despite the above known approaches for the treatment of oral conditions, especially for the whitening of teeth, a need still exists for providing products with both improved bleaching efficacy, increased speed of whitening, decreased tooth-sensitivity, and/or decreased oral soft tissue irritation. The prior art has generally attempted to address improved bleaching efficacy or increased speed of whitening by increasing the level of bleaching agent in the compositions. This approach, however, presents several problems. First the participant may experience increased irritation and/or sensitivity which may be associated with using an increased amount of a bleaching agent. Furthermore, some regulatory authorities and legislation in various geographies throughout the world do not allow bleaching agents to be used in products at levels above certain concentrations. Therefore, despite the above known approaches for the treatment of oral conditions, especially for the whitening of teeth, a need still exists for providing products with improved bleaching efficacy, increased speed of whitening, decreased tooth-sensitivity, and/or decreased oral soft tissue irritation.

SUMMARY

Without being bound to a theory it was surprisingly found that bleaching agents are effective in very low concentration, if presented in a multi-phase oral composition as disclosed herein.

A kit is provided that comprises in certain embodiments a multi-phase oral composition for whitening teeth, comprising in certain embodiments from about 0.002% to about 30% by weight of the multi-phase oral composition of a discontinuous aqueous phase having a bleaching agent; a hydrophobic phase; and a delivery carrier.

Embodiments of the present invention may be used to deliver whitening benefits to the oral cavity by directly applying the composition to the teeth.

A=strip of Munsell N8 Matte Color sheet attached to the strip holder to serve as a built-in Munsell N8 reference within each image.

B=Scale place in location where the peroxide test strip would normally be placed to show the approximate physical dimensions of the imaged objects.

C=DGK Plastic Gray card XL used as the background.

Figure 11:
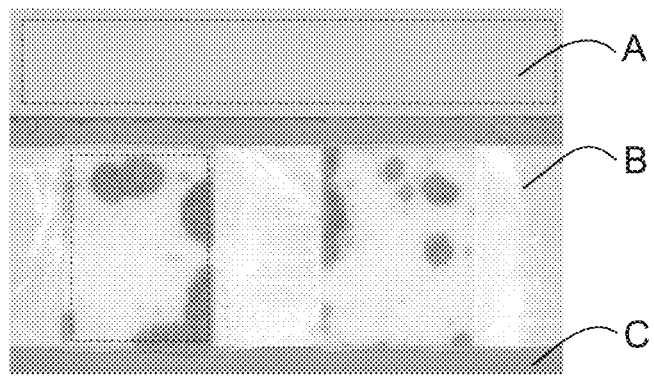

FIG. 11 is a sample digital image taken using the equipment, system configuration, and procedure specified herein as part of the procedure to measure the mean and standard deviation of the peroxide concentration of a multi-phase oral composition smeared onto test strips.

A=Strip of Munsell N8 Matte Color sheet attached to the strip holder to serve as a built-in Munsell N8 reference within each image. Dotted line illustrates the area selected by the rectangular marquee tool in Adobe CS4.

B=Peroxide test strip showing the two reaction-zones and spots of high peroxide concentration. Dotted line illustrates the area selected by the rectangular marquee tool in Adobe CS4.

C=DGK Plastic Gray card XL used as the background.

Figure 12:
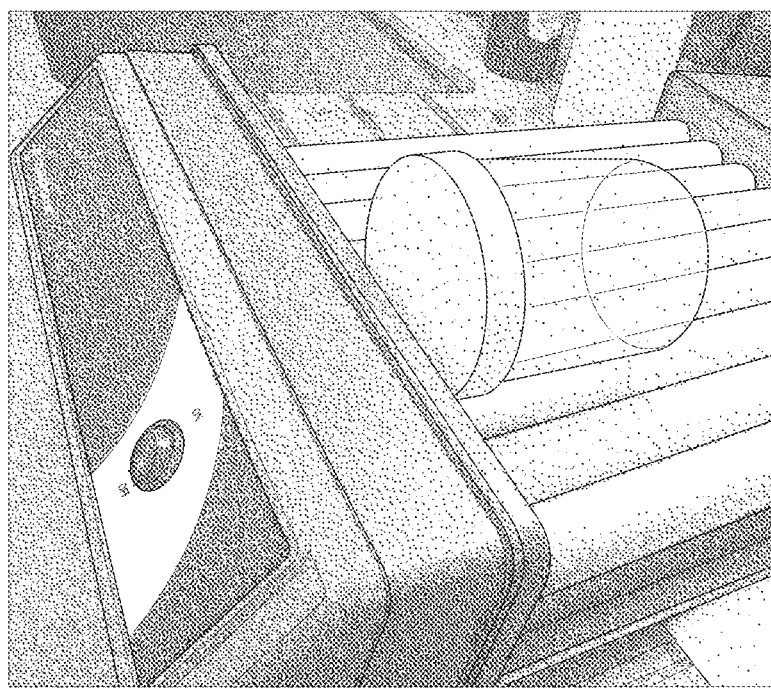

FIG. 12 illustrates the container and roller mixer used as part of the procedure to measure the residual peroxide concentration of a multiphase oral composition smeared onto teeth.

Figure 13:
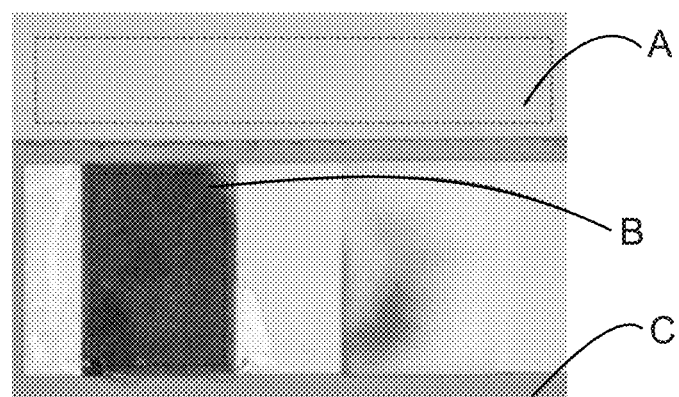

FIG. 13 is a sample digital image taken using the equipment, system configuration, and procedure specified herein as part of the procedure to measure the residual peroxide concentration of a multi-phase oral composition smeared onto teeth.

A=Strip of Munsell N8 Matte Color sheet attached to the strip holder to serve as a built-in Munsell N8 reference within each image. Dotted line illustrates the area selected by the rectangular marquee tool in Adobe CS4. B=Peroxide test strip showing the reaction-zone that was pressed against the tooth-disc and spots of high peroxide concentration. Dotted line illustrates the area selected by the rectangular marquee tool in Adobe CS4. C=DGK Plastic Gray card Xl used as the background.

DETAILED DESCRIPTION OF THE INVENTION

The present invention comprises a multi-phase oral composition for whitening teeth, having an aqueous phase, which in certain embodiments may range from about 0.002% to about 5% by weight of the multi-phase oral composition; a hydrophobic phase; and at least one oral care active agent in the aqueous phase; wherein the active agent is a bleaching agent, which in certain embodiments may be present up to 0.1% by weight of the multi-phase oral composition.

By "oral care composition", as used herein, is meant a product, which in the ordinary course of usage, is not intentionally swallowed for purposes of systemic administration of particular therapeutic agents, but is rather retained in the oral cavity for a time sufficient to contact dental surfaces or oral tissues. Examples of oral care compositions include dentifrice, tooth gel, subgingival gel, mouth rinse, mousse, foam, mouth spray, lozenge, chewable tablet, chewing gum, tooth whitening strips, floss and floss coatings, breath freshening dissolvable strips, or denture care or adhesive product. The oral care composition may also be incorporated onto strips or films for direct application or attachment to oral surfaces.

The term "dentifrice", as used herein, includes tooth or subgingival-paste, gel, or liquid formulations unless otherwise specified. The dentifrice composition may be a single phase composition or may be a combination of two or more separate dentifrice compositions. The dentifrice composition may be in any desired form, such as deep striped, surface striped, multilayered, having a gel surrounding a paste, or any combination thereof. Each dentifrice composition in a dentifrice comprising two or more separate dentifrice compositions may be contained in a physically separated compartment of a dispenser and dispensed side-by-side.

The term "immiscible" as used herein means less than 1 part by weight of the substance dissolves in 99 parts by weight of a second substance.

The term "phase" as used herein means a physically distinct region or regions, which may be continuous or discontinuous, having one or more properties that are different from another phase. Non-limiting examples of properties that may be different between phases include composition, viscosity, solubility, hydrophobicity, hydrophilicity, and miscibility.

The term "multi-phase oral composition" as used herein comprises a mixture of two or more phases that are immiscible with each other, for example such as water in oil emulsions. The phases may be continuous, discontinuous, or combinations thereof. Examples of multi-phase oral compositions include emulsions, in particular water in oil emulsions. Examples of multi-phase oral compositions also include oil-in-water emulsions, water-in-oil-in-water emulsions, and oil-in-water-in-oil emulsions. Examples of multi-phase oral compositions also include compositions where the phases are multi-continuous including bi-continuous, layered, striped, marbled, ribbons, swirled, and combinations thereof.

The term "emulsion" as understood herein is an example of a multi-phase oral composition wherein 1) at least one of the phases is discontinuous and 2) at least one of the phases is continuous. Examples of emulsions include droplets of water dispersed in oil. In this example the water and oil would be mutually immiscible with each other, water would be the discontinuous phase, and the oil would be the continuous phase.

The term "water-in-oil emulsion" as understood herein is an example of an emulsion wherein 1) the discontinuous phase is aqueous, and 2) the continuous phase is hydrophobic.

The term "aqueous phase" as understood herein is at least one phase that comprises water and a bleaching agent, and is immiscible with the hydrophobic phase. In certain embodiments, each part of the aqueous phase contains at least 2% of the bleaching agent by weight of the aqueous phase. Optionally the aqueous phase may further comprise ingredients that are water soluble, water miscible, or combinations thereof, such as for example water soluble solvents, alcohol, polyethylene glycol, carbopol, etc. or mixtures thereof. In some embodiments, if and when immiscible fillers are added to the aqueous phase, the percentage of the aqueous phase in the composition is calculated by excluding the immiscible filler.

The term "hydrophobic phase" as understood herein means all components of the composition that are immiscible with the aqueous phase. Optionally the hydrophobic phase may further comprise ingredients that are soluble, miscible or combinations thereof in the hydrophobic phase, such as for example hydrocarbon solvents dissolved into the hydrophobic phase, polyethylene dissolved into the hydrophobic phase, microcrystalline wax dissolved into the hydrophobic phase, or mixtures thereof.

The term "delivery carrier" as used herein comprises a material or an appliance that is used to hold the multi-phase oral composition against the tooth surface. Examples of delivery carriers include strips or dental trays.

The term "strip" as used herein comprises a material 1) whose longest dimension length is generally greater than its width, and 2) whose width is generally greater than its thickness. Strips may be rectangular, arched, curved, semi-circular, have rounded corners, have slits cut into it, have notches cut into it, bent into three dimensional shapes, or combinations thereof. Strips may be solid, semi-solid, textured, moldable, flexible, deformable, permanently deformable, or combinations thereof. Strips may be made from plastic sheets including polyethylene, or wax sheets. Examples of strips include a piece of polyethylene about 66 mm long, 15 mm wide and 0.0178 mm thick. Examples of permanently deformable strips include a piece of casting wax sheet about 66 mm long, 15 mm wide, and 0.4 mm thick.

The multi-phase oral compositions herein, which may be water in oil emulsions, are useful for topical application, in particular for topical application in the mouth. For example, the composition might be an oral care composition; by "oral care composition" or "multi-phase oral composition" as used herein is meant a product which in the ordinary course of usage is not intentionally swallowed for purposes of systemic administration of therapeutic agents, but is retained in the oral cavity for a sufficient time to contact the dental surfaces for purposes of whitening efficacy.

As used herein, the word "or" when used as a connector of two or more elements is meant to include the elements individually and in combination; for example X or Y, means X or Y or both.

As used herein, the articles "a" and "an" are understood to mean one or more of the material that is claimed or described, for example, "an oral care composition" or "a bleaching agent."

By "safe and effective amount" as used herein means an amount of a component, high enough to significantly (positively) modify the condition to be treated or to affect the desired whitening result, but low enough to avoid serious side effects (at a reasonable benefit/risk ratio), within the scope of sound medical/dental judgment. The safe and effective amount of a component, will vary with the particular condition being treated, the age and physical condition of the patient being treated, the severity of the condition, the duration of treatment, the nature of concurrent therapy, the specific form employed, and the particular vehicle from which the component is applied.

By "a sufficient period of time to achieve whitening" as used herein is meant that the composition is used or worn by the participant or the participant is instructed to use or wear the composition for greater than about 10 seconds; or greater than about 1 minute, such as from about 2.5 minutes to about 12 hours (for example overnight treatment), or from about 3 minutes to about 180 minutes; or greater than about 5 minutes, such as from about 5 minutes to about 60 minutes; or greater than about 10 minutes, such as from about 10 minutes to about 60 minutes; or from about 1, 5, 10, or 15 minutes to about 20, 30, 60, 120 minutes per application; or any other numerical range, which is narrower and which falls within such broader numerical range, as if such narrower numerical ranges were all expressly written herein. In addition, the treatments may be applied from about 1, 2, or 3 times a day to about 4, 5, 6 or 7 times a day. The treatments may be applied for from about 1, 2, 3, 4, 5, 6, or about 7 days to about 8, 9, 10, 11, 12, 13, 14, 21, or 28 days or any other numerical range, which is narrower and which falls within such broader numerical range, as if such narrower numerical ranges were all expressly written herein. Further, the length of treatment to achieve the desired benefit, for example, tooth whitening, may last for a specified period of time, which may be repeated if necessary, for example from about one day to about six months, in particular from about one day to about 28 days, or from about 7 to about 28 days. The optimal duration and frequency of application will depend on the desired effect, the severity of any condition being treated, the health and age of the user and like considerations.

The term "dispenser", as used herein, means any pump, tube, or container suitable for dispensing oral care compositions.

By "μm" or "microns" as used herein is meant micrometer.

The term "equivalent diameter" of a droplet as used herein means the diameter of a sphere having the same volume as the droplet.

The term "two-dimensional density of droplets" as used herein means the number of droplets of aqueous phase a) that are present in a square centimeter of a two-dimensional plane in the multi-phase oral composition and b) wherein the cross-sectional area of the droplets in the two-dimensional plane are larger than a specified value.

All percentages and ratios used herein after are by weight of total composition (wt %), unless otherwise indicated. All percentages, ratios, and levels of ingredients referred to herein are based on the actual amount of the ingredient, and do not comprise solvents, fillers, or other materials with which the ingredient may be combined as a commercially available product, unless otherwise indicated. For example, a composition that contains 0.2857% of an aqueous solution of 35% hydrogen peroxide $H_2O_2$ and 99.7143% petrolatum would mean this composition contains 0.2857% of an aqueous phase (the aqueous solution of 35% $H_2O_2$) and 99.7143% of a hydrophobic phase (the petrolatum), and 0.099995% of a bleaching agent (the $H_2O_2$ in the aqueous phase). As another example, a composition that contains 0.2857% of an aqueous solution of 35% $H_2O_2$, 89.7143% petrolatum, and 10% silica dispersed in the petrolatum would mean this composition contains 0.2857% of an aqueous phase (the aqueous solution of 35% $H_2O_2$), 99.7143% of a hydrophobic phase (the petrolatum and silica which are both immiscible with the aqueous phase) including the 10% of a filler (the silica), and 0.099995% of a bleaching agent (the $H_2O_2$ in the aqueous phase). This would also mean that this composition has a ratio of the concentration in weight percent of bleaching agent present in the aqueous phase to the concentration in weight percent of bleaching agent present in the overall multi-phase oral composition of 350.02 (namely 35% divided by 0.099995%).

As yet another example, a multi-phase oral composition that contains 0.2857% of an aqueous solution of 35% hydrogen peroxide ($H_2O_2$), 99.6143% petrolatum, and 0.1% cross-linked siloxane particles dispersed in the aqueous phase would mean this multi-phase oral composition contains 0.2857% of an aqueous phase (namely the aqueous solution of 35% $H_2O_2$), 99.7143% of a hydrophobic phase (namely the petrolatum and cross-linked siloxane particles which are both immiscible with the aqueous phase), 0.099995% of a bleaching agent (namely the $H_2O_2$ in the aqueous phase), and 0.1% of a filler (namely the cross-linked siloxane particles). This would mean that this composition has a ratio of the concentration in weight percent of bleaching agent present in the aqueous phase to the concentration in weight percent of bleaching agent present in the overall multi-phase oral composition of 350.02 (namely 35% divided by 0.099995%).

All measurements referred to herein are made at about 23° C. (i.e. room temperature) unless otherwise specified.

"Active and other ingredients" useful herein may be categorized or described herein by their cosmetic and/or therapeutic benefit or their postulated mode of action or function. However, it is to be understood that the active and other ingredients useful herein can, in some instances, provide more than one cosmetic and/or therapeutic benefit or function or operate via more than one mode of action. Therefore, classifications herein are made for the sake of convenience and are not intended to limit an ingredient to the particularly stated function(s) or activities listed.

The term "teeth", as used herein, refers to natural teeth as well as artificial teeth or dental prosthesis and is construed to comprise one tooth or multiple teeth. The term "tooth surface" as used herein, refers to natural tooth surface(s) as well as artificial tooth surface(s) or dental prosthesis surface(s) accordingly.

The term "orally acceptable carrier" comprises one or more compatible solid or liquid excipients or diluents which are suitable for use in the oral cavity. By "compatible," as used herein, is meant that the components of the composition are capable of being commingled without interaction in a manner which would substantially reduce the composition's stability and/or efficacy.

Multi-Phase Oral Compositions

The multi-phase oral compositions as disclosed herein may be water-in-oil emulsions. The multi-phase oral compositions may be micro-emulsions or macro-emulsions.

For water-in-oil emulsions comprising a bleaching agent, it has been surprisingly found that the size of the droplets of the aqueous phase is a factor to decrease oral/topical irritation and/or tooth-sensitivity. Without being bound by theory, if the size of the droplets of the aqueous phase is too large it may lead to large spots on oral/topical/tooth surfaces that are exposed to a high concentration of the bleaching agent, which in turn may lead to oral/topical irritation and/or tooth-sensitivity. In certain embodiments, the number-average equivalent-diameter or volume-average equivalent-diameter of the droplets of aqueous phase may be no more than about 0.001 micron, 0.01 micron, 0.1 micron, 1 micron, 5 microns, 10 microns, 50 microns, 100 microns, 500 microns, or 1000 microns or any other numerical range, which is narrower and which falls within such broader numerical range, as if such narrower numerical ranges were all expressly written herein. In certain embodiments, the number-average equivalent-diameter or volume-average equivalent-diameter of the droplets of aqueous phase may be from about 0.001 micron to about 1000 microns, preferably from about 0.01 micron to about 1000 microns, more preferably from about 0.1 micron to about 100 microns, and most preferably from about 1 to about 100 microns or any other numerical range, which is narrower and which falls within such broader numerical range, as if such narrower numerical ranges were all expressly written herein. Compositions that have a high density of large droplets of aqueous phase may lead to oral/topical irritation and/or tooth-sensitivity. It is worth noting that measuring the number-average equivalent-diameter or volume-average equivalent-diameter of the droplets of aqueous phase requires one to measure the entire distribution of droplets sizes in three dimensions—this may require multiple different techniques that are suited for small, medium and large droplets. In contrast, the procedure specified herein to measure the "two-dimensional density of droplets" can be used to measure only the large droplets and only in two dimensions—this can be done using a light microscope by counting the number of droplets larger than a specified size (at the two-dimensional focal plane), and does not require more complex equipment. In certain embodiments, the "two-dimensional density of droplets" of aqueous phase measured using the procedure specified herein with a cross-sectional area larger than about 1000, 3000, 10000, 20000, or 50000 square microns may be no more than about 0.5, 1, 2, 3, 4, 5, 6, 7, 8, 9, 10, 15, 20, 25, 50, or 100 per square centimeter of the two-dimensional plane, or any other numerical range, which is narrower and which falls within such broader numerical range as if such narrower numerical ranges were all expressly written herein. In certain embodiments, the "two-dimensional density of droplets" of aqueous phase measured using the procedure specified herein with a cross-sectional area larger than about 10000 square microns may be no more than about 25, preferably no more than 10, more preferably no more than 5, and most preferably no more than 1 per square centimeter of the two-dimensional plane or any other numerical range, which is narrower and which falls within such broader numerical range as if such narrower numerical ranges were all expressly written herein.

Figure 8:
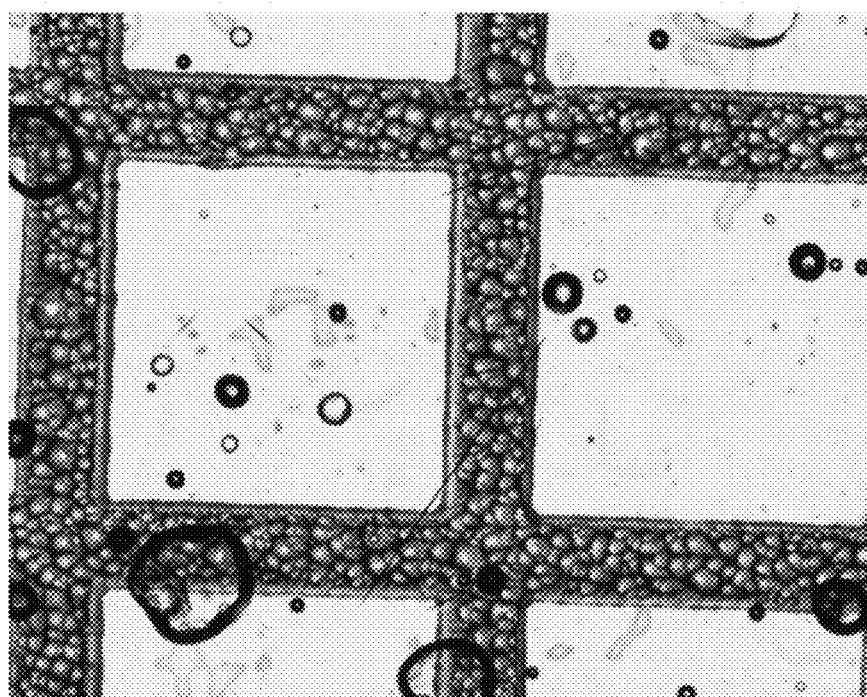
FIG. 8 is a sample photograph illustrating the aqueous phase droplets vs. air-bubbles vs. ink patterns as part of the procedure to measure the two-dimensional density of droplets of aqueous phase of a multiphase oral composition.

Procedure to Measure the Two-Dimensional Density of Droplets of Aqueous Phase of a Multi-Phase Oral Composition 1. Cut one 20×20 mm grid out of an adhesive grid sticker* (supplied by Diversified Biotech Dedham, MA, item number GRID-1000; purchased from VWR, Batavia, IL, catalog number 89032-163) and stick it to the top of a glass microscope slide (VWR Micro Slides, Super Frost Plus, 25×75×1 mm, manufactured by VWR International, Radnor, PA;
   purchased from VWR, Batavia, IL, catalog number 48311-703).
   each grid sticker has two side-by-side 20×20 mm grids, and each cell within each grid measures 1×1 mm.
2. Use a small spatula and place a small sample of the composition in the middle of the adhesive grid sticker stuck to the microscope slide. The amount of sample should be such that after it has been pressed down per step-3, at least 100 cells of the grid are completely covered with the composition and can be measured. Take care to place the sample as a single blob on the adhesive grid sticker—this helps minimize air-entrapment when the coverslip is placed over it.
3. Place a coverslip (VWR Microscope Cover Glasses, 22×22 mm, purchased from VWR, Batavia, IL, catalog number 16004-094) over the sample-composition and press down until the sample-composition is about 100 microns thick. This may be done by placing a second microscope slide over the coverslip and sandwiching a pair of coverslips as spacers on either side of the sample-composition between the two microscope slides and manually pressing down until the sample is about 100 microns thick. Note, to make sure each individual sample is about 100 microns thick, the thickness of each individual grid sticker, coverslip, and microscope slide will need to be measured.
4. Place the microscope slide on a microscope and focus on the sample using light transmitted through the sample. Use a microscope and a magnification level that a) provide a field of view encompassing at least one whole cell of the grid such that all four edges of the cell are visible within the field of view, and b) enable the measurement of the cross-sectional area of droplets of aqueous phase larger than the specified value.
5. Center the field of view on a single cell of the grid. Count the number of droplets of aqueous phase that: a) are visible in the cell (including those that are on the grid lines, but taking care not to double-count these); and b) whose cross-sectional area at the two-dimensional focal plane is larger than the specified value. Take care not to count residual air-bubbles (unlike droplets of aqueous phase, air bubbles may be identified by thick dark walls in the field of view), or features of the ink pattern on the grid sticker (unlike droplets of aqueous phase, features of the ink pattern are crowded together and appear only on the grid lines). FIG. 8 shows a sample image of the droplets of aqueous phase Vs. air-bubbles Vs. features of the ink pattern.
6. Repeat step 5 for each cell that is completely covered by the composition. There should at least 100 cells that are completely covered by the composition per slide.
7. The "two-dimensional density of droplets" with a cross-sectional area larger than a specified value (expressed as number of droplets per square centimeter) for this slide is calculated as: The total number of droplets of aqueous phase whose cross-sectional area at the two-dimensional focal plane is larger than the specified value in all cells measured in this slide DIVIDED by the total area of all cells measured in this slide expressed in square centimeters.
8. Repeat steps-1-7 for a total of at least twelve slides. Average the calculation from step-7 across all the slides measured. This is the final "two-dimensional density of droplets" with a cross-sectional area larger than a specified value (expressed as number of droplets per square centimeter).

For multi-phase oral compositions that comprise peroxide, it has been surprisingly found that the standard deviation of the peroxide concentration of a multi-phase oral composition smeared onto peroxide test strips is a factor to decrease oral/topical irritation and/or tooth-sensitivity during use. Each peroxide test strip has two reaction-zones that change color (driving the RED intensity lower) in areas or spots that are contacted with peroxide. Thus, without being bound by theory, peroxide test strips may conveniently be used as a proxy for oral/topical/tooth surfaces to identify spots of high peroxide concentration that may lead to oral/topical irritation and/or tooth-sensitivity. Furthermore, since contact with peroxide drives the RED intensity lower in the reaction-zones, the mean RED intensity of peroxide test strips smeared with the multi-phase oral composition subtracted from the mean baseline RED intensity of untreated peroxide test strips may conveniently be used as a measure of the mean peroxide concentration. Multi-phase oral compositions that have large spots of high peroxide concentration when the multi-phase oral composition is smeared on peroxide test strips may also have large spots of high peroxide concentration when the multi-phase oral composition is applied to oral/topical/tooth surfaces—this in turn may lead to oral/topical irritation and/or tooth-sensitivity. In contrast, multi-phase oral compositions that have only small spots of high peroxide concentration when the multi-phase oral composition is smeared onto peroxide test strips may also have only small spots of high peroxide concentration when the multi-phase oral composition is applied to oral/topical/tooth surfaces—this in turn may lead to low oral/topical irritation and/or tooth-sensitivity. The spots of peroxide concentration when the multi-phase oral composition is smeared onto peroxide test strips can be quantified by the standard deviation of the peroxide concentration on the test strips measured using the procedure specified herein. Multi-phase oral compositions that have large spots of high peroxide concentration when the multi-phase oral composition is smeared onto peroxide test strips have a high standard deviation of the peroxide concentration on the test strips. In contrast, multi-phase oral compositions that have only small spots of high peroxide concentration when the multi-phase oral composition is smeared onto peroxide test strips have a low standard deviation of the peroxide concentration on the test strips.

Furthermore, multi-phase oral compositions with large droplets may cause large spots of high peroxide concentration when the multi-phase oral composition is smeared onto peroxide test strips—this in turn may lead to a high standard deviation of the peroxide concentration on the test strips. In contrast, multi-phase oral compositions that have little or no large droplets may cause only small spots of high peroxide concentration when the multi-phase oral composition is smeared onto peroxide test strips—this in turn may lead to a low standard deviation of the peroxide concentration on the test strips.

In certain embodiments the standard deviation of the peroxide concentration of a multi-phase oral composition smeared onto peroxide test strips measured using the procedure specified herein may be no more than about 5, 10, 15, 20, 25, 30, 40, 50, or 100 or any other numerical range, which is narrower and which falls within such broader numerical range, as if such narrower numerical ranges were all expressly written herein. In certain embodiments the standard deviation of the peroxide concentration of a multi-phase oral composition smeared onto peroxide test strips measured using the procedure specified herein may be no more than about 50, preferably no more than about 25, more preferably no more than about 10, and most preferably no more than about 5, or any other numerical range, which is narrower and which falls within such broader numerical range, as if such narrower numerical ranges were all expressly written herein.

For multi-phase oral compositions that comprise peroxide, it has surprisingly been found that the mean peroxide concentration of a multi-phase oral composition smeared onto peroxide test strips is a factor to deliver bleaching efficacy. Without being bound by theory, if the mean peroxide concentration of a multi-phase oral composition smeared onto peroxide test strips is low, the mean peroxide concentration delivered to the tooth surface during use may also be low, which could lead to low bleaching effectiveness. In contrast, if the mean peroxide concentration of a multi-phase oral composition smeared onto peroxide test strips is high, the mean peroxide concentration delivered to the tooth surface during use may also be high, which could lead to high bleaching effectiveness. In certain embodiments, the mean peroxide concentration of a multi-phase oral composition smeared onto peroxide test strips measured using the procedure specified herein may be from about 1, 2, 5, 10, 15, 20, 25, 30, 35, 40, 45, 50, 55, 60, 65, 70, 75, 80, 85, 90, 95, 100, 125, 150, 175, 200, or 225 to about 2, 5, 10, 15, 20, 25, 30, 35, 40, 45, 50, 55, 60, 65, 70, 75, 80, 85, 90, 95, 100, 125, 150, 175, 200, or 225 or any other numerical range, which is narrower and which falls within such broader numerical range, as if such narrower numerical ranges were all expressly written herein. In certain embodiments, the mean peroxide concentration of a multi-phase oral composition smeared onto peroxide test strips measured using the procedure specified herein may be from about 1 to about 100, preferably from about 2 to about 75, more preferably from about 5 to about 50, and most preferably from about 10 to about 50 or any other numerical range, which is narrower and which falls within such broader numerical range, as if such narrower numerical ranges were all expressly written herein.

For multi-phase oral compositions that comprise peroxide, it has surprisingly been found that the ratio of the mean peroxide concentration of a multi-phase oral composition smeared onto peroxide test strips to the standard deviation of the peroxide concentration of a multi-phase oral composition smeared onto peroxide test strips is a factor to deliver a high ratio of bleaching efficacy to oral/topical irritation and/or tooth-sensitivity. Without being bound by theory, if the ratio of the mean peroxide concentration of a multi-phase oral composition smeared onto peroxide test strips to the standard deviation of the peroxide concentration of a multi-phase oral composition smeared onto peroxide test strips is high, the composition may deliver high efficacy combined with low oral/topical irritation and/or tooth-sensitivity during use. In contrast, if the ratio of the mean peroxide concentration of a multi-phase oral composition smeared onto peroxide test strips to the standard deviation of the peroxide concentration of a multi-phase oral composition smeared onto peroxide test strips is low, the composition may deliver low efficacy combined with high oral/topical irritation and/or tooth-sensitivity during use. In certain embodiments the ratio of the mean peroxide concentration of a multi-phase oral composition smeared onto peroxide test strips measured using the procedure specified herein to the standard deviation of the peroxide concentration of a multi-phase oral composition smeared onto peroxide test strips measured using the procedure specified herein may be no less than about 0.25, 0.5, 1, 1.5, 2, 2.5, 3, 3.5, 4, 4.5, 5, 6, 7, 8, 9, 10, 15, 20, 25, 50 or any other numerical range, which is narrower and which falls within such broader numerical range, as if such narrower numerical ranges were all expressly written herein. In certain embodiments the ratio of the mean peroxide concentration of a multi-phase oral composition smeared onto peroxide test strips measured using the procedure specified herein to the standard deviation of the peroxide concentration of a multi-phase oral composition smeared onto peroxide test strips measured using the procedure specified herein may be no less than than about 0.5, preferably no less than about 1, more preferably no less than about 2, and most preferably no less than about 3.5, or any other numerical range, which is narrower and which falls within such broader numerical range, as if such narrower numerical ranges were all expressly written herein.

Figure 9:
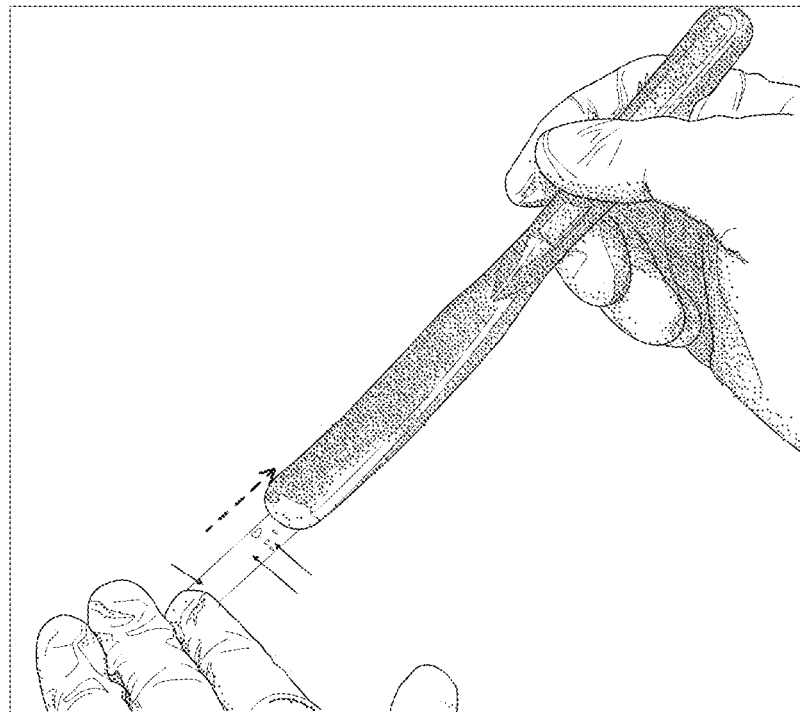
FIG. 9 illustrates the procedure to smear the composition onto the peroxide test strips as part of the procedure to measure the mean and standard deviation of the peroxide concentration of a multi-phase oral composition smeared onto test strips.
Figure 10:
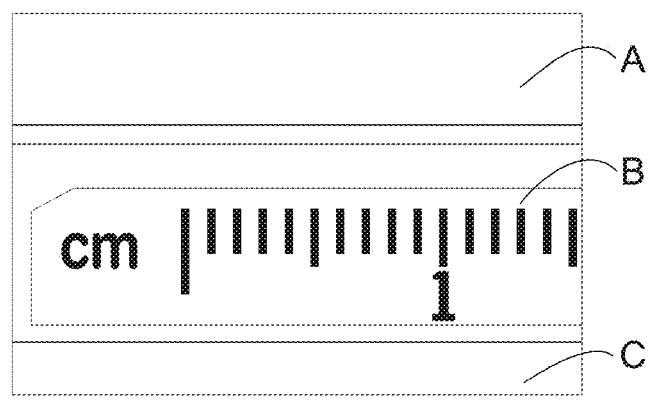
FIG. 10 illustrates a digital image taken using the equipment, system configuration, and procedure specified herein as part of the procedure to measure the mean and standard deviation of the peroxide concentration of a multi-phase oral composition smeared onto test strips.

Method to Measure the Mean and Standard Deviation of the Peroxide Concentration of a Multi-Phase Oral Composition Smeared onto Peroxide Test Strips 1. Weigh 0.60 to 0.80 gram of the composition onto the end of a clean hard rubber spatula (4" long blade, from VWR, Batavia, IL 60510, USA., catalog number 57930-025).
2. Take a fresh peroxide test strip (EMD Millipore Corporation, Billerica, MA, supplier number 1.16974.0001; purchased from VWR, Batavia, IL, catalog number EM1.16974.0001) out of the container, and start a timer.
3. Take a digital image of the peroxide test strip. The equipment and system configuration used to take the digital image of the test strip are specified herein. Sample digital images are shown in FIGS. 10 and 11. Place the peroxide test strip on a fresh paper towel.
4. Hold the spatula and peroxide test strip as shown in FIG. 9. Smear the composition (pre-weighed in step-1) with firm pressure from left to right onto both reaction-zones on the test strip. Repeat the smearing motion a total of three strokes from left to right with the same sample of composition that has already been pre-weighed onto the spatula.
5. Move the peroxide test strip to a clean area of the paper towel. Place a filter paper (Whatman Grade 1 Qualitative Filter Paper Standard Grade, circle, 90 mm, supplier number 1001-090; from VWR, Batavia, IL 60510, USA., catalog number 28450-081) on top of the test strip. Apply finger pressure on top of the filter paper. Pull the peroxide test strip out from under the filter paper (while maintaining finger pressure on the filter paper) in a single stroke such that excess gel is wiped off onto the filter paper and paper towel. Make sure the reaction-zones do not get dislodged from the peroxide test strip.
6. Take a digital image of the peroxide test strip. The equipment and system configuration used to take the digital image of the test strip are specified herein. Sample digital images are shown in FIGS. 10 and 11.
7. Steps 2 to 6 should be completed within 90 seconds on the timer.
8. Repeat steps 1 to 7 for a total of at least eighteen peroxide test strips.
9. Use Adobe Photoshop CS4 with the procedure specified herein to measure the mean and standard deviation of the RED intensities of the strip of Munsell N8 Matte Color sheet attached to the holder that serves as a built-in Munsell N8 reference within each image. The mean RED intensity of the built-in Munsell N8 reference within each image should be from 204 to 212 and the standard deviation should be no more than 3.
10. Use Adobe Photoshop CS4 with the procedure specified herein to measure the mean and standard deviation of the RED intensities of each reaction-zone on all peroxide test strips at BASELINE (before smearing with the composition).
11. Use Adobe Photoshop CS4 with the procedure specified herein to measure the mean and standard deviation of the RED intensities of each reaction-zone on all peroxide test strips AFTER smearing with the composition.
12. The mean peroxide concentration of the composition smeared on peroxide test strips is calculated as follows: First, calculate the mean baseline RED intensity of each reaction-zone from step-10 MINUS the mean RED intensity of the same reaction-zone after smearing with the composition from step-11. Repeat this calculation for all reaction-zones, and average the results across all reaction-zones on all peroxide test strips. This is the mean peroxide concentration of the composition smeared on peroxide test strips.
13. The standard deviation of the peroxide concentration of the composition smeared on peroxide test strips is calculated as: Average the standard deviation of the RED intensities across all reaction-zones on all peroxide test strips AFTER they have been smeared with the composition from step-11. This is the standard deviation of the peroxide concentration of the composition smeared on peroxide test strips.

To validate the equipment, system configuration, and procedure specified herein, the mean and standard deviation of the RED intensities of a Munsell N8 Matte Color sheet (from Munsell Color, Division of X-rite, Grand Rapids, MI, USA) needs to be measured and demonstrated to be from 204 to 212 for the mean and no more than 3 for the standard deviation.

Equipment to Take Digital Images of Peroxide Test Strips
- 1—Digital camera capable of capturing images at 18 million pixels (5184×3456) resolution jpg image and capable of a shutter speed of $1/250^{th}$ of a second (such as Canon 60D camera from Canon USA Inc., Lake Success, NY 11042)
- 1—Memory card
- 1—Lens adapter if needed (such as Canon body to Nikon lens adapter)
- 1—105 mm lens (such as 105 mm Micro Nikkor lens from Nikon USA Inc. Melville, NY 11747)
- 1—52 mm Flash adapter ring
- 1—Macro ring lite with polarization filter attached (such as Canon MR-14EX Macro ring lite with polarization filter attached from Canon USA Inc., Lake Success, NY 11042)
- 1—52 mm Rotating Circular Polarizer on the lens
- 1—Tripod
- 1—Sheet Munsell N8 Matte Color sheet (from Munsell Color, Division of X-rite, Grand Rapids, MI, USA)
- 1—Holder for the peroxide test strips made using DGK Plastic Gray card XL (from DGK Color Tools on Amazon.com) as the background, and a strip of Munsell N8 Matte Color sheet attached to serve as a built-in Munsell N8 reference within each image.
- 1—mm scale mounted to a blank specimen strip System Configuration to Take Digital Images of Peroxide Test Strips
1. The tripod is configured with the tripod mount attached to the underside of the tripod to accommodate macro photography, with the camera pointing down toward the table. The subject plane is 317 mm from the sensor plane.
2. The Nikorr 105 mm lens is attached to the Canon 60D camera body using the Canon to Nikon adapter mount.
3. The rotating polarizer is attached to the 105 mm Micro Nikkor lens.
4. The 52 mm flash adapter ring is attached to the front of the 105 mm lens.
5. The Canon MR-14EX Macro ring lite with polarization filter is attached to the front of the lens to the flash adapter ring.
6. The rotating circular polarizer on the lens is rotated until the maximum gloss/glare is removed and complete cross polarization is achieved.
7. The flash is set to 'manual' mode with the power setting set to ⅛ power.
8. The Canon 60D camera is set to 'manual' mode with the ISO set to 100.
9. The Shutter is set to $1/250^{th}$ of a Second.
10. The aperture is set at f=8 on the 105 mm Micro Nikkor lens.
11. Manual Focus is used on the 105 mm Micro Nikkor lens with the focus to 317 mm distance from the sensor plane to the subject plane.
12. A mounted sheet of calibrated Munsell N8 material is used to achieve White Balance for the images.
13. The camera is set to capture images at the 18 million pixels (5184×3456) resolution jpg image.
14. The total exposure setting for the camera and flash needs to be configured such that a captured image of the Munsell N8 Matte Color sheet has a mean RED intensity of 204 to 212 and a standard deviation of no more than 3 measured using the procedure specified herein.

Procedure in Adobe Photoshop CS4 to Measure the Mean and Standard Deviation of the RED Intensities
1. Open Adobe Photoshop CS4.
2. On the top edge of the screen select "Window", followed by "Histogram". This displays the histogram of the image. In the Histogram window, select "Expanded view" and "Show statistics". This displays the histogram with statistics. Make sure the "Channel" is set to "RED". In Adobe Photoshop CS4, a histogram panel displays the tonal range of an image. It shows how the pixels are distributed by graphing the number of pixels at each of the 256 intensity levels from 0-255 in the region of interest selected. Pixels with the same intensity level are stacked in bars along the vertical axis. The higher the bar the greater number of pixels at that intensity level. The vertical bars toward the right side of the histogram indicate pixels with higher intensities, while bars toward the left side of the histogram indicate pixels with lower intensities.
3. The mean and standard deviation of the RED intensities of the Munsell N8 Matte Color sheet is measured as follows: Open a captured image of the Munsell N8 Matte Color sheet using Adobe CS4. On the left edge of the screen, select the "Rectangular Marquee Tool". On the top edge of the screen, set "Feather" to 0 px, "Style" to Fixed size, "Width" to 5000 px, and "Height" to 3300 px. This defines a rectangle containing 16500000 pixels whose size & shape matches the size & shape of images of the Munsell N8 Matte Color sheet. Select the image of the Munsell N8 Matte Color sheet using the "Rectangular Marquee Tool". Make sure the edges of the rectangle are within the edges of the image of the Munsell N8 Matte Color sheet. Click the circular symbol on the Histogram panel and make sure "Cache Level" reads 1 in the Histogram panel. This measures and displays the mean and standard deviation of the RED intensities the Munsell N8 Matte Color sheet. Record these values.
4. The mean and standard deviation of the RED intensities of the built-in Munsell N8 reference within each image is measured as follows: Open a captured image of the built-in Munsell N8 reference within each image using Adobe CS4. On the left edge of the screen, select the "Rectangular Marquee Tool". On the top edge of the screen, set "Feather" to 0 px, "Style" to Fixed size, "Width" to 5000 px, and "Height" to 800 px. This defines a rectangle containing 4000000 pixels whose size & shape matches the size & shape of the built-in Munsell N8 reference within each image. Select the built-in Munsell N8 reference within each image using the "Rectangular Marquee Tool". Make sure the edges of the rectangle are within the edges of the built-in Munsell N8 reference within each image. Click the circular symbol on the Histogram panel and make sure "Cache Level" reads 1 in the Histogram panel. This measures and displays the mean and standard deviation of the RED intensities of the built-in Munsell N8 reference within each image. Record these values.
5. The mean and standard deviation of the RED intensities of each reaction-zone on the peroxide test strip is measured as follows: Open a captured image of the peroxide test strip using Adobe CS4. On the left edge of the screen, select the "Rectangular Marquee Tool". On the top edge of the screen, set "Feather" to 0 px, "Style" to Fixed size, "Width" to 1300 px, and "Height" to 1750 px. This defines a rectangle containing 2275000 pixels whose size & shape matches the size & shape of images of each reaction-zone on the peroxide test strip. Select one of the two reaction-zones on the peroxide test strip using the "Rectangular Marquee Tool". Make sure the edges of the rectangle are within the edges of the reaction-zone. Click the circular symbol on the Histogram panel and make sure "Cache Level" reads 1 in the Histogram panel. This measures and displays the mean and standard deviation of the RED intensities of one of the two reaction-zones on the peroxide test strip. Record these values.

The components of the aqueous phase and hydrophobic phase are chosen to allow for the release of the bleaching agent located in the aqueous phase readily from the composition.

Without being bound by theory it is believed that when the present invention, which may be in the form of a water in oil emulsion, is brought into contact with a tooth surface, the aqueous phase and the components of the aqueous phase may migrate to the tooth surface. The possible net effect is that the teeth whitening effect is started only after contact with the tooth surface to be treated. That means, the bleaching agent may be covered, protected against environmental influence and thereby stabilized by the hydrophobic phase of the multi-phase oral composition until use and potentially by the hydrophobic phase in form of a film or layer during use. Thereby, the active effect may be applied to the tooth surface and the active agent, e.g. the bleaching agent may be potentially shielded against the oral environment during use.

Thereby the efficacy of a whitening multi-phase oral composition may be enhanced and/or accelerated.

Without further being bound by theory, the present invention may improve the delivery of the whitening agent to the tooth surface and thus the whitening performance due to the partial hydrophobic and partial hydrophilic nature of the composition. Due to the driving force resulting therefrom the bleaching agent present in the aqueous phase may be driven towards the tooth surface. Thereby increased speed of whitening and increased efficacy of the bleaching agent may be achieved, even though surprisingly low total levels of the bleaching agent are used. The present invention, therefore, at a given total overall concentration, such as 0.1%, 1%, or 5%, by weight or below of a bleaching agent, delivers a surprisingly high level of whitening efficacy, may require fewer applications to get the same degree of whitening, or may require a lower gel load (milligrams of gel per unit area) to get the same degree of whitening.

In addition, retention of the multi-phase oral composition on the tooth surfaces may be improved as the hydrophobic phase resists salivary dilution and salivary enzymes which can decompose the peroxide. Even furthermore, the hydrophobic phase does not dehydrate the teeth creating and outward flux of water created by many hydrophilic compositions containing hydrophilic adhesives such as polycarboxylic acid. Since the hydrophobic phase does not dehydrate the teeth it may result in a surprisingly low level of tooth sensitivity even while delivering a surprisingly high level of whitening efficacy.

In addition, the hydrophobic phase may provide further advantages. For example, the hydrophobic phase represents a stable matrix for ingredients which are soluble in the hydrophobic phase. For example, many flavor ingredients usually used in multi-phase oral compositions are soluble in the hydrophobic phase. That means the flavor ingredients may be protected from any influence of the active agent, for example the bleaching agent, in the multi-phase oral composition. In addition, during use of the multi-phase oral composition at the tooth surface at least part of the hydrophobic phase may be located—without being bound by theory-towards the soft oral tissues, such as the mucosa, thereby presenting the ingredients which are present in the hydrophobic phase, such as flavor compounds, to the oral cavity. In addition, the hydrophobic phase may shield the active agent, such as the bleaching agent against any influence from the oral cavity, such as dilution by saliva. The shielding effect may also apply to the tooth surface(s) themselves, wherein the hydrophobic phase may provide greater hydration of the teeth surfaces.

In certain embodiments, multi-phase oral compositions of the present invention may be in the form of a liquid, viscous liquid, gel, semi-solid, solid, particulate, powder, viscoelastic liquid, viscoelastic gel, sol, viscoelastic solid, or any combination thereof.

Aqueous Phase

The present multi-phase oral compositions comprise an aqueous phase.

In certain embodiments, the maximum amount of aqueous phase may be 0.3%, 0.5%, 1%, 2%, 3%, 4%, 5%, 10%, 15%, 20%, 30%, 40%, 50% or 60% by weight of the multi-phase oral composition or any other numerical range, which is narrower and which falls within such broader numerical range, as if such narrower numerical ranges were all expressly written herein.

In certain embodiments, the amount of aqueous phase may be from about 60%, 55%, 50%, 45%, 40%, 35%, 30%, 25%, 20%, 15%, 10%, 5%, 4%, 3%, 2%, 1.5%, 1.4%, 1.3%, 1.2%, 1.1%, 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, 0.01% or 0.002% by weight of the multi-phase oral composition to about 60%, 55%, 50%, 45%, 40%, 35%, 30%, 25%, 20%, 15%, 10%, 5%, 4%, 3%, 2%, 1.5%, 1.4%, 1.3%, 1.2%, 1.1%, 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, 0.01% or 0.002% by weight of the multi-phase oral composition or any other numerical range, which is narrower and which falls within such broader numerical range, as if such narrower numerical ranges were all expressly written herein. In certain embodiments, the amount of aqueous phase may be from about 0.002% to about 5%, from about 0.1% to about 2%, from about 0.1% to about 1%, or from about 0.1% to about 0.5% by weight of the multi-phase oral composition, or any other numerical range, which is narrower and which falls within such broader numerical range, as if such narrower numerical ranges were all expressly written herein. In certain embodiments the amount of the aqueous phase may be less than about 60%, 55%, 50%, 45%, 40%, 35%, 30%, 25%, 20%, 15%, 10%, 5%, 4%, 3%, 2%, 1.5%, 1.4%, 1.3%, 1.2%, 1.1%, 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, or 0.01% by weight of the multi-phase oral composition or any other numerical range, which is narrower and which falls within such broader numerical range, as if such narrower numerical ranges were all expressly written herein. In certain embodiments, the amount of the aqueous phase may be less than about 1.0% or 0.9% by weight of the multi-phase oral composition. In certain embodiments, the aqueous phase may be from about 0.002% to about 5%, preferably from about 0.01% to about 5%, more preferably from about 0.1% to about 5%, and most preferably from about 1% to about 5% by weight of the multi-phase oral composition or any other numerical range, which is narrower and which falls within such broader numerical range, as if such narrower numerical ranges were all expressly written herein.

In certain embodiments, the aqueous phase may be from about 0.002% to about 15%, preferably from about 1% to about 15%, more preferably from about 5% to about 15%, and most preferably from about 5% to about 10% by weight of the multi-phase oral composition or any other numerical range which is narrower and which falls within such broader numerical range, as if such narrower numerical ranges were all expressly written herein.

In certain embodiments, the aqueous phase may be from about 0.9% to about 60%, preferably from about 6% to about 30%, more preferably from about 7% to about 20%, and most preferably from about 10% to about 30% by weight of the multi-phase oral composition or any other numerical range which is narrower and which falls within such broader numerical range, as if such narrower numerical ranges were all expressly written herein.

The aqueous phase may include water, polyalkylene glycols with molecular weights from about 200 to about 20,000, humectants, and mixtures thereof. Humectants generally include edible polyhydric alcohols such as glycerin, sorbitol, xylitol, butylene glycol, polyethylene glycol, and propylene glycol, and mixtures thereof. The aqueous phase may comprise at least about 10% by weight of the aqueous phase water, or at least about 20% by weight of the aqueous phase water.

Bleaching Agent

The present multi-phase oral compositions further comprise a safe and effective amount of a bleaching agent, wherein the level of bleaching agent is based on the available oxygen or chlorine respectively that the molecule is capable of providing to bleach the stain. In certain embodiments, the maximum amount of bleaching agent may be 0.1%, 1%, 5%, 10%, 15% or 20% by weight of the multi-phase oral composition or any other numerical range, which is narrower and which falls within such broader numerical range, as if such narrower numerical ranges were all expressly written herein.

In certain embodiments, the bleaching agent may be from about 0.001%, 0.01%, 0.02%, 0.03%, 0.04%, 0.05%, 0.06%, 0.07%, 0.08%, 0.09%, 0.095% 0.099995%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 15% or 20% to about 0.001%, 0.01%, 0.02%, 0.03%, 0.04%, 0.05%, 0.06%, 0.07%, 0.08%, 0.09%, 0.095% 0.099995%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 15% or 20% by weight of the multi-phase oral composition or any other numerical range, which is narrower and which falls within such broader numerical range, as if such narrower numerical ranges were all expressly written herein.

In certain embodiments the bleaching agent level may be less than 0.09%, 0.095% 0.099995%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, or 10% by weight of the multi-phase oral composition, in some embodiments less than 0.9%, 0.8%, 0.7%, 0.6%, 0.5%, 0.4%, 0.3%, 0.2%, or 0.1%, by weight of the multi-phase oral composition, preferably from about 0.1% to about 0.9%, more preferred from about 0.2% to about 0.8%, more preferred from about 0.3% to about 0.7% by weight of the multi-phase oral composition or any other numerical range, which is narrower and which falls within such broader numerical range, as if such narrower numerical ranges were all expressly written herein. In certain embodiments, the bleaching agent may be from about 0.001% to about 1%, preferably from about 0.01% to about 0.1%, more preferably from about 0.1% to about 1%, and most preferably from about 0.5% to about 1% by weight of the multi-phase oral composition or any other numerical range, which is narrower and which falls within such broader numerical range, as if such narrower numerical ranges were all expressly written herein.

In certain embodiments, the bleaching agent may be from about 0.6% to about 5%, preferably from about 0.6% to about 4%, more preferably from about 1% to about 4%, and most preferably from about 1% to about 3% by weight of the multi-phase oral composition or any other numerical range which is narrower and which falls within such broader numerical range, as if such narrower numerical ranges were all expressly written herein.

In certain embodiments, the bleaching agent may be from about 0.6% to about 10%, preferably from about 0.6% to about 6%, more preferably from about 1% to about 5%, and most preferably from about 1% to about 3% by weight of the multi-phase oral composition or any other numerical range which is narrower and which falls within such broader numerical range, as if such narrower numerical ranges were all expressly written herein.

The level of bleaching agent may be based on the available oxygen or chlorine respectively that the molecule is capable of providing to bleach a stain. In certain embodiments the bleaching agent level is less than about 0.1% by weight of the multi-phase oral composition, in certain embodiments less than about 0.09%, 0.08%, 0.07%, 0.06%, 0.05%, 0.04%, 0.03%, 0.02%, 0.01%, or 0.001% by weight of the multi-phase oral composition, or from about 0.01% to about 0.099995%, from about 0.01% to about 0.095%, or from about 0.05% to about 0.09% by weight of the multi-phase oral composition, or any other numerical range, which is narrower and which falls within such broader numerical range, as if such narrower numerical ranges were all expressly written herein. Surprisingly, the bleaching agent is significantly effective when used even at the low levels in the multi-phase oral compositions as disclosed herein.

In certain embodiments the present multi-phase oral compositions comprise a bleaching agent, wherein the bleaching agent may be present in the aqueous phase from about 2%, 5%, 8.75%, 10%, 15%, 17.5%, 20%, 25%, 30%, 35%, or 45%, to about 50%, 45%, 40%, 35%, 30%, 25%, 20%, 17.5%, 15%, 10%, 8.75%, or 5%, by weight of the aqueous phase or any other numerical range, which is narrower and which falls within such broader numerical range, as if such narrower numerical ranges were all expressly written herein.

In certain embodiments, the bleaching agent present in the aqueous phase may be at least or more than about 17.5%, 20%, 25%, 30%, 35%, 45%, 50%, or 60% by weight of the aqueous phase or any other numerical range, which is narrower and which falls within such broader numerical range, as if such narrower numerical ranges were all expressly written herein.

Ratio of Concentrations of Bleaching Agent

In certain embodiments the multi-phase oral compositions of the present invention deliver a high ratio of the concentration in weight percent of bleaching agent present in the aqueous phase to the concentration in weight percent of bleaching agent present in the overall multi-phase oral composition, as they have a high concentration in weight percent of bleaching agent present in the aqueous phase combined with a relatively low concentration in weight percent of bleaching agent present in the overall multi-phase oral composition. Without being bound by theory, this surprising combination of seemingly contradictory parameters in the present invention delivers the bleaching agent to the tooth surface with a high driving force even when the overall concentration or amount of bleaching agent delivered to the tooth surface is low. Consequently, 1) The high driving force delivers a surprisingly high level of bleaching efficacy and/or bleaching speed, while 2) The low overall concentration or low amount of bleaching agent delivered to the tooth surface may help reduce tooth sensitivity.

The ratio of the concentration in weight percent of bleaching agent present in the aqueous phase to the concentration in weight percent of bleaching agent present in the overall multi-phase oral composition may be from about 67000, 50000, 35000, 20000, 17500, 10000, 5000, 3500, 2000, 1750, 1160, 1000, 875, 700, 580, 500, 430, 400, 380, 350, 200, 175, 111, 110, 105, 100, 90, 80, 70, 60, 50, 40, 30, 20, 15, 10, or 5 to about 67000, 50000, 35000, 20000, 17500, 10000, 5000, 3500, 2000, 1750, 1160, 1000, 875, 700, 580, 500, 430, 400, 380, 350, 200, 175, 111, 110, 105, 100, 90, 80, 70, 60, 50, 40, 30, 20, 15, 10, or 5 or any other numerical range, which is narrower and which falls within such broader numerical range, as if such narrower numerical ranges were all expressly written herein.

In certain embodiments, the present multi-phase oral compositions comprises a bleaching agent, wherein the ratio of the concentration in weight percent of bleaching agent present in the aqueous phase to the concentration in weight percent of bleaching agent present in the overall multi-phase oral composition may be at least or more than about 67000, 50000, 35000, 20000, 17500, 10000, 5000, 3500, 2000, 1750, 1160, 1000, 875, 700, 580, 500, 430, 400, 380, 350, 200, 175, 110, 105, 100, 90, 80, 70, 60, 50, 40, 30, 20, 15, 10, or 5 or any other numerical range, which is narrower and which falls within such broader numerical range, as if such narrower numerical ranges were all expressly written herein.

Suitable bleaching agents include agents that provide bleaching effects, stain bleaching effects, stain removal effects, stain color change effects or any other effect, which change, or brighten tooth color. For example, in certain embodiments bleaching agents comprise a source of peroxide radicals. In addition, bleaching agents may include peroxides, metal chlorites, perborates, percarbonates, peroxyacids, persulfates, compounds that form the preceding compounds in situ, and combinations thereof. Examples of peroxide compounds include hydrogen peroxide, urea peroxide, calcium peroxide, carbamide peroxide, and mixtures thereof. In certain embodiments, the bleaching agent may be hydrogen peroxide ($H_2O_2$). Suitable metal chlorites include calcium chlorite, barium chlorite, magnesium chlorite, lithium chlorite, sodium chlorite, potassium chlorite, and mixtures thereof. Additional bleach agents also include hypochlorite (such as metal hypochlorites) and chlorine dioxide. Persulfates include salts of peroxymonosulfate, peroxydisulfate, and mixtures thereof. The starting bleaching agent material can be an aqueous or solid material.

The bleaching agents of the present invention may be stabilized against degradation due to the shielding effect of the hydrophobic phase. In certain embodiments, after 180 days of storage in the dark at 30° C. following formulation, multi-phase oral compositions of the present invention comprised at least about 10% of the initial amount of hydrogen peroxide they were formulated with. In certain embodiments, at least about 25% of the initial amount of hydrogen peroxide, at least about 50% of the initial amount of hydrogen peroxide, or at least about 75% of the initial amount of hydrogen peroxide may be present after 180 days storage of the composition at 30° C.

Optional Stabilizing Agent for the Bleaching Agent

The multi-phase oral compositions of the present invention may comprise a stabilizing agent for the bleaching agent. The bleaching agent may be further stabilized against degradation by the multi-phase oral composition. Therefore, stabilizing agents may be added to the aqueous phase of the present composition. In particular, if hydrogen peroxide is used stabilizing agents may be added. Suitable stabilizing agents are for example ortho-phosphoric acid, phosphate(s), such as sodium hydrogen phosphate, pyrophosphate(s), organophosphonate(s), Ethylenediaminetetraacetic acid, Ethylenediamine-N,N'-diacetic acid, Ethylenediamine-N,N'-disuccinic acid, potassium stannate, sodium stannate, tin salts, zinc salts, salicylic acid, 1-Hydroxyethylidene-1,1-diphosphonic acid, and combinations thereof. In particular, stabilizers may be used which show additional oral care effects, such as anti-tartar effect, produced by pyrophosphate (s) or organophosphonate(s). In certain embodiments, a stabilizing agent may be present in a multi-phase oral composition of the present invention in an amount from about 0.0000001%, 0.000001%, or 0.00001%, to about 0.00001%, 0.0001%, or 0.01% by weight of the multi-phase oral composition or any other numerical range, which is narrower and which falls within such broader numerical range, as if such narrower numerical ranges were all expressly written herein. In certain embodiments, a stabilizing agent may be present in a multi-phase oral composition of the present invention in an amount from about 0.0001%, or 0.01% to about 0.01%, 0.1% or about 1% by weight of the aqueous phase or any other numerical range, which is narrower and which falls within such broader numerical range, as if such narrower numerical ranges were all expressly written herein.

A stabilizing agent may also include chelants. The chelant may be a copper, iron and/or manganese chelants, or a mixture thereof. Suitable chelants may be selected from: diethylene triamine pentaacetate, diethylene triamine penta (methyl phosphonic acid), ethylene diamine-N'N'-disuccinic acid, ethylene diamine tetraacetate, ethylene diamine tetra (methylene phosphonic acid), hydroxyethane di(methylene phosphonic acid), and any combination thereof. A suitable chelant may be selected from ethylene diamine-N'N'-disuccinic acid (EDDS), hydroxyethane diphosphonic acid (HEDP) or mixtures thereof. The stabilizer may comprise ethylene diamine-N'N'-disuccinic acid or salt thereof. The ethylene diamine-N'N'-disuccinic acid may be in S,S enantiomeric form. The stabilizer may comprise 4,5-dihydroxy-m-benzenedisulfonic acid disodium salt, glutamic acid-N,N-diacetic acid (GLDA) and/or salts thereof, 2-hydroxypyridine-1-oxide, Trilon P™ available from BASF, Ludwigshafen, Germany. Suitable chelants may also be calcium carbonate crystal growth inhibitors. Suitable calcium carbonate crystal growth inhibitors may be selected from the group consisting of: 1-hydroxyethanediphosphonic acid (HEDP) and salts thereof; N,N-dicarboxymethyl-2-aminopentane-1,5-dioic acid and salts thereof; 2-phosphonobutane-1,2,4-tricarboxylic acid and salts thereof; and any combination thereof.

A stabilizer may comprise a calcium carbonate crystal growth inhibitor, such as 1-hydroxyethanediphosphonic acid (HEDP); N,N-dicarboxymethyl-2-aminopentane-1,5-dioic acid; 2-phosphonobutane-1,2,4-tricarboxylic acid; and salts thereof; and any combination thereof.

A stabilizer may comprise a hydroxamate chelant. By 'hydroxamate' we herein mean hydroxamic acid or a corresponding salt, for example coco hydroxamic acid (Axis House RK 853).

Hydrophobic Phase

The present invention comprises a safe and effective amount of a hydrophobic phase. In certain embodiments, the present multi-phase oral compositions comprise a hydrophobic phase, wherein the hydrophobic phase may be at least or more than about 40%, 45%, 50%, 55%, 60%, 65%, 70%, 75%, 80%, 85%, 90%, 95%, 96%, 97%, 98%, 99%, 99.1%, or 99.5% by weight of the multi-phase oral composition or any other numerical range, which is narrower and which falls within such broader numerical range, as if such narrower numerical ranges were all expressly written herein.

In certain embodiments, the hydrophobic phase may be at least about 95%, 96%, 97%, 98%, 99%, 99.1%, or 99.5% by weight of the multi-phase oral composition or any other numerical range, which is narrower and which falls within such broader numerical range, as if such narrower numerical ranges were all expressly written herein.

In certain embodiments, the hydrophobic phase may be in predominant proportion relative to the aqueous phase present in the multi-phase oral composition. As used herein "predominant proportion" means that the percent by weight of the hydrophobic phase of the multi-phase oral composition is in excess relative to the percent by weight of the aqueous phase of the multi-phase oral composition.

The hydrophobic phase may be inert or at least partially inert. The hydrophobic phase may interact, but in certain embodiments does not interact or only minimally interact with the other ingredients, such as for example, flavors or thickeners, in the multi-phase oral composition, including the bleaching agent.

A suitable hydrophobic phase for the compositions as disclosed herein may have an octanol/water partition coefficient (log $P_{ow}$) of greater than about 2, 3, 4, 5, or greater than about 5.5. In certain embodiments, the hydrophobic phase shows a log $P_{ow}$ greater than about 6 or any other numerical range, which is narrower and which falls within such broader numerical range, as if such narrower numerical ranges were all expressly written herein.

Without being bound by theory, the drop melting point of the hydrophobic phase may be a factor to ensure that the composition: 1) is substantive and does not run down the teeth or run out of the delivery carrier during application or during use; and 2) releases an effective amount of the bleaching agent or active agent during use. Specifically, if the drop melting point of the hydrophobic phase is too low, the multi-phase oral composition may not be substantive and run down the teeth or run out of the delivery carrier during application or during use. In contrast, if the drop melting point of the hydrophobic phase is too high, the multi-phase oral composition may not release an effective amount of the bleaching agent or active agent during use. The drop melting point of a suitable hydrophobic phase may be in the range of from about 40° C. to about 80° C., from about 50° to about 65° C., from about 50° C. to about 60° C., or any other numerical range, which is narrower, and which falls within such broader numerical range, as if such narrower numerical ranges were all expressly written herein, as measured according to ASTM method D127-08. In certain embodiments, the drop melting point of the hydrophobic phase may be from about 120 C, 100 C, 90 C, 85 C, 80 C, 75 C, 70 C, 60 C, 50 C, 40 C, or 30 C, to about 100 C, 90 C, 85 C, 80 C, 75 C, 70 C, 60 C, 50 C, 40 C, 30 C, or 25 C, or any other numerical range, which is narrower, and which falls within such broader numerical range, as if such narrower numerical ranges were all expressly written herein, as measured according to ASTM method D127-08.

Without being bound by theory, the cone penetration consistency value of the hydrophobic phase or the multi-phase oral composition may be a factor to ensure that the multi-phase oral composition: 1) is substantive and does not run down the teeth or run out of the delivery carrier during application or during use; and 2) releases an effective amount of the bleaching agent or active agent during use. Specifically, if the cone penetration consistency value of the hydrophobic phase or the multi-phase oral composition is too high, the multi-phase oral composition may not be substantive and run down the teeth or run out of the delivery carrier during application or during use. In contrast, if the cone penetration consistency value of the hydrophobic phase or the multi-phase oral composition is too low, the multi-phase oral composition may not release an effective amount of the bleaching agent or active agent during use. In certain embodiments, the cone penetration consistency value of the hydrophobic phase or multi-phase oral compositions may be in the range of from about 100 to about 300, preferably in the range from about 150 to about 250, and more preferably in the range of from about 170 to about 200 or any other numerical range, which is narrower and which falls within such broader numerical range, as if such narrower numerical ranges were all expressly written herein, as measured according to ASTM method D937-07. In certain embodiments, the cone penetration consistency value of the hydrophobic phase or multi-phase oral composition may be from about 10, 25, 50, 100, 110, 120, 130, 140, 150, 160, 170, 180, 190, 200, 210, 220, 230, 240, 250, 300, 400, or 500, to about 25, 50, 100, 110, 120, 130, 140, 150, 160, 170, 180, 190, 200, 210, 220, 230, 240, 250, 300, 400, or 500, or any other numerical range, which is narrower, and which falls within such broader numerical range, as if such narrower numerical ranges were all expressly written herein as measured according to ASTM method D937-07.

Without being bound by theory, for multi-phase oral compositions that comprise peroxide, the mean residual peroxide concentration of the multi-phase oral composition smeared on teeth may be a factor to ensure that the multi-phase oral composition: 1) is substantive and does not wash away during use; and 2) still releases an effective amount of the bleaching agent during use. Specifically, if the mean residual peroxide concentration of the multi-phase oral composition on a tooth surface is too low, the multi-phase oral composition may not be substantive and wash away during use, or not release an effective amount of the bleaching agent during use. In certain embodiments, the mean residual peroxide concentration of a multi-phase oral composition smeared on teeth measured using the procedure specified herein may be from about 1, 2, 5, 10, 15, 20, 25, 30, 35, 40, 45, 50, 55, 60, 65, 70, 75, 80, 85, 90, 95, 100, 125, 150, 175, 200, or 225 to about 2, 5, 10, 15, 20, 25, 30, 35, 40, 45, 50, 55, 60, 65, 70, 75, 80, 85, 90, 95, 100, 125, 150, 175, 200, or 225 or any other numerical range, which is narrower and which falls within such broader numerical range, as if such narrower numerical ranges were all expressly written herein. In certain embodiments, the mean residual peroxide concentration of a multi-phase oral composition smeared on teeth measured using the procedure specified herein may be from about 1 to about 200, preferably from about 10 to about 200, more preferably from about 50 to about 200, and most preferably from about 100 to about 200, or any other numerical range, which is narrower and which falls within such broader numerical range, as if such narrower numerical ranges were all expressly written herein.

Procedure to Measure the Mean Residual Peroxide Concentration of a Composition Smeared on Teeth
1. Cut a circular disc (7.5 to 7.8 mm diameter×1.2 to 1.3 mm thickness) out of the front surface of a human incisor tooth. Leave the front surface intact but flatten the back surface that has been cut out of tooth using sand paper. Soak the tooth-disc in 15 to 20 ml of water that meets USP specification in a glass vial for at least 24 hours. Take the tooth-disc out of the water and place it on a fresh paper towel with the front surface facing upward.
2. Weigh 290 to 310 grams of water that meets USP specifications into a cylindrical plastic container with a screw-top lid 82 to 107 mm in diameter×106 to 108 mm height ("Max 200 Long Cup Translucent", item number 501 220t from Flacktek, Landrum, SC). Pre-heat the water in the container with the lid screwed on tight in a convection oven with air temperature at 33 C to 35 C for at least 12 hours.
3. Weigh 0.04 to 0.06 gram of the composition onto the tip of a disposable lip gloss applicator ("Flocked Doe Foot Lip Gloss Applicator" made of Nylon and Polystyrene, purchased from Qosmedix Inc., Ronkonkoma, NY, catalog number 74111).
4. Smear the composition onto the front surface of the wet tooth-disc by first rolling the tip of the lip gloss applicator loaded with the composition on the front surface of the tooth-disc to transfer the composition onto the tooth-disc and then fanning out toward the circular edge.
5. Pick up the tooth-disc with a tweezer. Make sure the tweezer touches only the circular edge of the tooth-disc and not the surface of the tooth-disc smeared with the composition. Tilt the plastic container and gently place the tooth-disc in the water on the cylindrical wall of the container where the cylindrical wall and flat bottom meet. Make sure the treated surface of the tooth-disc is facing upward away from the cylindrical wall of the container.

6. Place the cylindrical container on a roller mixer (model number TSRT9 by Techne purchased from VWR, Batavia, IL, catalog number 89132-186; or item number 04750-30 from Cole-Parmer Inc., Vernon Hills, IL). Turn on the roller mixer—this gently rotates the container at 12 to 14 RPM. The tooth-disc should continue to remain immersed in the water and the treated surface should continue to face away from the rotating cylindrical wall. This rotating motion causes the water to flow gently over the tooth-disc similar to the gentle movement of saliva and other liquids over teeth in the mouth. This is illustrated in FIG. 12.

7. After 58 to 62 minutes shut off the roller mixer, take a fresh peroxide test strip (supplied by EMD Millipore Corporation, Billerica, MA, supplier number 1.16974.0001; purchased from VWR, Batavia, IL, catalog number EM1.16974.0001) out of the container, and start a timer.

8. Take a digital image of the peroxide test strip. The equipment and system configuration used to take the digital image of the test strip are specified herein. A sample digital image is shown in FIG. 13.

9. Remove the tooth-disc from the water using a tweezer. As before, make sure the tweezer touches only the circular edge of the tooth-disc and not the surface of the tooth-disc smeared with the composition. Place the tooth-disc on a gloved finger-tip. Make sure the surface of the tooth-disc smeared with the composition is facing upward away from the gloved finger-tip.

10. Place the peroxide test strip against the tooth-disc such that one of the reaction-zones contacts the surface of the tooth-disc with the residual composition. Pinch the peroxide test strip against the tooth-disc between thumb and forefinger and apply firm finger pressure between thumb and forefinger for 2 to 3 seconds.

11. Move the peroxide test strip to a clean area of a paper towel. Place a filter paper (Whatman Grade 1 Qualitative Filter Paper Standard Grade, circle, 90 mm, supplier number 1001-090; purchased from VWR, Batavia, IL, catalog number 28450-081) on top of the test strip. Apply finger pressure on top of the filter paper. Pull the peroxide test strip out from under the filter paper (while maintaining finger pressure on the filter paper) in a single stroke such that excess gel is wiped off onto the filter paper and paper towel. Make sure the reaction-zones do not get dislodged from the peroxide test strip.

12. Take a digital image of the peroxide test strip. The equipment and system configuration used to take the digital image of the test strip are specified herein. A sample digital image is shown in FIG. 13.

13. Steps 7 to 12 must be completed within 3 minutes on the timer.

14. Repeat steps 1 to 13 for a minimum of twelve teeth.

15. Use Adobe Photoshop CS4 with the procedure specified herein to measure the mean and standard deviation of the RED intensities of the strip of Munsell N8 Matte Color sheet attached to the holder that serves as a built-in Munsell N8 reference within each image. The mean RED intensity of the built-in Munsell N8 reference within each image should be from 204 to 212 and the standard deviation should be no more than 3.

16. Use Adobe Photoshop CS4 with the procedure specified herein to measure the mean of the RED intensities of the reaction-zone on all peroxide test strips at BASELINE (before pressing against the tooth-disc).

17. Use Adobe Photoshop CS4 with the procedure specified herein to measure the mean of the RED intensities of same the reaction-zone on all peroxide test strips AFTER pressing against the tooth-disc.

18. The mean residual peroxide concentration of a composition smeared on teeth is calculated as follows: First, calculate the mean baseline RED intensity of each reaction-zone from step-16 MINUS the mean RED intensity of the same reaction-zone after pressing with the residual composition on the tooth-disc from step-17. Repeat this calculation for all reaction-zones pressed against the tooth-disc, and average the results. This is the mean residual peroxide concentration of a composition smeared on teeth.

In certain embodiments, the density of the hydrophobic phase used in the multi-phase oral compositions of the present invention is in the range of from about 0.8 g/cm3 to about 1.0 g/cm3, from about 0.85 g/cm3 to about 0.95 g/cm3, or about 0.9 g/cm3, or any other numerical range, which is narrower, and which falls within such broader numerical range, as if such narrower numerical ranges were all expressly written herein.

In certain embodiments, the hydrophobic phase may be a non-toxic oil, such as non-toxic edible oil. In certain embodiments, the hydrophobic phase may include non-toxic edible oils, saturated or unsaturated fatty alcohols, aliphatic hydrocarbons, long chain triglycerides, fatty esters, and mixtures thereof. In certain embodiments, the hydrophobic phase may also comprise silicones, polysiloxanes, and mixtures thereof. In certain embodiments, the hydrophobic phase may be selected from mineral oil, petrolatum and mixtures thereof, more preferred petrolatum, e.g. white petrolatum, is used as the hydrophobic phase of the present composition. Examples of petrolatum include Snow White Pet—C from Calumet Specialty Products (Indianapolis, IN), G-2191 from Sonneborn (Parsippany, NJ), G-2218 from Sonneborn, G-1958 from Sonneborn, G-2180 from Sonneborn, Snow White V28 EP from Sonneborn, and Snow White V30 from Sonneborn, and mixtures thereof.

In certain embodiments, the aliphatic hydrocarbons may contain from about 10, 12, 14, or 16 to about 16, 18, 20, 22, 24, 26, 28, 30, 36, 40 carbon atoms such as decane, 2 ethyldecane, tetradecane, isotetradecane, hexadecane, cicosane, and mixtures thereof. In certain embodiments, long chain triglycerides may include vegetable oils, fish oils, animal fats, hydrogenated vegetable oils, partially hydrogenated vegetable oils, semi-synthetic triglycerides, synthetic triglycerides, and mixtures thereof. In certain embodiments, fractionated, refined or purified oils of these types can also be used. In certain embodients, examples of long chain triglyceride-containing oils include almond oil; babassu oil; borage oil; black currant seed oil; canola oil; castor oil; coconut oil; corn oil; cottonseed oil; emu oil; evening primrose oil; flax seed oil; grapeseed oil; groundnut oil; mustard seed oil; olive oil; palm oil; palm kernel oil; peanut oil; rapeseed oil; safflower oil; sesame oil; shark liver oil; soybean oil; sunflower oil; hydrogenated castor oil; hydrogenated coconut oil; hydrogenated palm oil; hydrogenated soybean oil; hydrogenated vegetable oil; a mixture of hydrogenated cottonseed oil and hydrogenated castor oil; partially hydrogenated soybean oil; a mixture of partially hydrogenated soybean oil and partially hydrogenated cottonseed oil; glyceryl trioleate; glyceryl trilinoleate; glyceryl trilinolenate; a Ω3-polyunsaturated fatty acid triglyceride containing oil; and mixtures thereof. The long chain triglyceride containing oils may be in particular, selected from the group consisting of corn oil, olive oil, palm oil, peanut oil, safflower oil, sesame oil, soybean oil, castor oil, linseed oil, rape oil, rice bran oil, coconut oil, hydrogenated castor oil; partially hydrogenated soybean oil; glyceryl trioleate; glyceryl trilinoleate; a Ω3-polyunsaturated fatty acid triglyceride containing oil; and mixtures thereof.

In certain embodiments, suitable saturated or unsaturated fatty alcohols have from about 6 to about 20 carbon atoms, cetearyl alcohol, lauryl alcohol, and mixtures thereof. For example, Lipowax (Cetearyl Alcohol and Ceteareth-20) are supplied and manufactured by Lipo Chemical.

General information on silicones including silicone fluids, gums and resins, as well as the manufacture of silicones, can be found in Encyclopedia of Polymer Science and Engineering, Volume 15, Second Edition, pp 204-308, John Wiley & Sons Inc. 1989 and Chemistry and Technology of Silicones, Walter Noll, Academic Press Inc, (Harcourt Brue Javanovich, Publishers, New York), 1968, pp 282-287 and 409-426.

The multi-phase oral composition as disclosed herein may comprise additional ingredients which can be added optionally and which will be described below in further detail.

The multi-phase oral compositions of the present invention may comprise an emulsifier. Surprisingly, in certain embodiments, a multi-phase oral composition may be formed even when no emulsifier is used. Without being bound by a theory it is believed that the low amount of aqueous phase, combined with the rheological properties, flow properties, drop melting point, and/or cone penetration consistency of the hydrophobic phase, and/or the process of preparation of the composition may help to disperse the aqueous phase into the hydrophobic phase and keep it dispersed without the use of an emulsifying agent. Thus, the present whitening multi-phase oral compositions are preferably substantially free of ingredients that may compromise the efficacy, usage experience, concentration of actives or bleaching agents at the tooth surface over time, active or bleaching efficiency, or compatibility between ingredients, for example an emulsifier. "Substantially free of an emulsifier" as understood herein means that the composition comprises less than 0.001% by weight of an emulsifier. More preferred the present whitening multi-phase oral compositions are free of an emulsifier, i.e. do not comprise any emulsifier In certain embodiments, the multi-phase oral compositions may comprise from about 0.001% to 30% of an emulsifier. Any emulsifier may be used as long as the emulsifier chosen is non-toxic to a user. In certain embodiments, an emulsifier (or a combination of emulsifiers) favors the formation of a multi-phase oral composition. In certain embodiments, the present multi-phase oral compositions may comprise from about 0 to about 0.1%, from about 0.1 to about 5%, from about 0.1 to about 3%, or from about 0.5% to about 1.5% by weight of the multi-phase oral composition, of emulsifier.

Classes of surfactants useful as emulsifiers include nonionic, anionic, cationic, amphoteric, synthetic emulsifying agents, and mixtures thereof. Many suitable nonionic and amphoteric surfactants are disclosed by U.S. Pat. Nos. 3,988,433; 4,051,234, and many suitable nonionic surfactants are also disclosed by U.S. Pat. No. 3,959,458.

In certain embodiments, since multi-phase oral compositions are favored with more lipophilic emulsifiers, the emulsifier may have an HLB value of from about 1 to about 10, an HLB value of from about 3 to about 8, an HLB value from about 4 to about 7, or an HLB from about 4 to about 6. Either a single emulsifier may be used or a combination of emulsifiers may be used. In certain embodiments, the emulsifier may be a blend of two or more emulsifiers, such as a blend of two or more nonionic emulsifiers. In this regard an emulsifier that tends to form a multi-phase oral composition and an emulsifier that forms an oil in water emulsion may be blended to achieve the requisite HLB for a multi-phase oral composition (HLB values are algebraically additive).

Other emulsifiers, also useful herein include natural emulsifying agents, such as acacia, gelatin, lecithin and cholesterol; finely dispersed solids, such as colloidal clays, bentonite, veegum (magnesium aluminum silicate; and synthetic emulsifying agents, such as salts of fatty acids, sulfates such as sorbitan trioleate, sorbitan tristearate, sucrose distearate, propylene glycol monostearate, glycerol monostearate, propylene glycol monolaurate, sorbitan monostearate, sorbitan monolaurate, polyoxyethylene-4-lauryl ether, sodium lauryl sulfate, sulfonates such as dioctyl sosium sulfosuccinate, glyceryl esters, polyoxyethylene glycol esters and ethers, diethylene glycol monostearate, PEG 200 distearate, and sorbitan fatty acid esters, such as sorbitan monopalmitate, and their polyoxyethylene derivatives, polyoxyethylene glycol esters such as the monostearate, Polysorbate 80 (ethoxylated sorbitan monooleate) (supplied by Spectrum, etc.); and mixtures thereof.

An emulsifier may be a surfactant that is non reactive with a bleaching agent. For example, surfactants that are non-reactive with a bleaching agent have no hydroxy groups, are free of nitrogen groups and linkages, are essentially free of metals such as Zn, etc.

The emulsifier may be a non-ionic surfactant. Nonionic surfactants include polyoxyethylene sorbitan fatty acid esters, such as, materials sold under the trademark Tween. The number following the 'polyoxyethylene' part in the following section refers to the total number of oxyethylene —($CH_2CH_2O$)— groups found in the molecule. The number following the 'polysorbate' part is related to the type of fatty acid associated with the polyoxyethylene sorbitan part of the molecule. Monolaurate is indicated by 20, monopalmitate is indicated by 40, monostearate by 60, and monooleate by 80. Examples of such materials are polyoxyethylene (20) sorbitan monolaurate (Tween 20), polyoxyethylene (20) sorbitan monopalmitate (Tween 40), polyoxyethylene (20) sorbitan monostearate (Tween 60), polyoxyethylene (4) sorbitan monostearate (Tween 61), polyoxyethylene (20) sorbitan tristearate (Tween 65), polyoxyethylene (20) sorbitan monooleate (Tween 80), polyoxyethylene (5) sorbitan monooleate (Tween 81), and polyoxyethlene (20) sorbitan trioleate (Tween 85), and mixtures thereof. Polyoxyethylene fatty acid esters are also suitable and examples include those materials sold under the trademark Myrj such as polyoxyethylene (8) stearate (Myrj 45) and polyoxyethylene (40) stearate (Myrj 52), and mixtures thereof. Further nonionics include, polyoxyethylene polyoxypropylene block polymers, such as poloxamers and Pluronics.

Another suitable class of non-ionic surfactants for optional use in the present invention are polyoxyethylene fatty ethers, such as, the materials sold under the trademark Brij. Examples of such materials are polyoxyethylene (4) lauryl ether (Brij 30), polyoxyethylene (23) lauryl ether (Brij 35), polyoxyethylene (2) cetyl ether (Brij 52), polyoxyethylene (10) cetyl ether (Brij 56), polyoxyethylene (20) cetyl ether (Brij 58), polyoxyethylene (2) stearyl ether (Brij 72), polyoxyethylene (10) stearyl ether (Brij 76), polyoxyethylene (20) stearyl ether (Brij 78), polyoxyethylne (2) oleyl ether (Brij 93), polyoxyethylene (10) oleyl ether, and polyoxyethylene (20) oleyl ether (Brij 99), and mixtures thereof.

A portion of a non-ionic surfactant may be substituted with a lipophilic surfactant, such as, sorbitan fatty acid esters such as the materials sold under the trademark Arlacel. Suitable lipophilic surfactants include sorbitan monolaurate (Arlacel 20), sorbitan monopalmitate (Arlacel 40), sorbitan monostearate (Aracel 60), sorbitan monooleate (Arlacel 80), sorbitan sesquioleate (Arlacel 83), and sorbitan trioleate (Arlacel 85), and mixtures thereof. Typically, from about 2% to about 90% of the level of the nonionic surfactant may be substituted by a lipophilic surfactant, or from about 25% to about 50%.

In certain embodiments, the emulsifier may be Aerosol OT (sodium dioctyl sulfosuccinate) manufactured by Cytec.

In addition, in certain embodiments, the multi-phase oral compositions may be also substantially free of ingredients that may compromise the efficacy, usage experience, concentration of actives or bleaching agents at the tooth surface over time, active or bleaching efficiency, or compatibility between ingredients, for example acids and/or alcohols. In certain embodiments, multi-phase oral compositions may comprise less than 0.001% by weight of the composition, of acids and/or alcohols, preferably multi-phase oral compositions do not comprise acids and/or alcohols. Without being bound by a theory it is believed that the decrease in surface tension produced by alcohol may decrease the retention time of the aqueous phase at the tooth surface, thereby decreasing the efficacy of the oral care actives. The presence of acids might contradict with the actives and/or may produce negative side effects as the tooth surface such as hypersensitivity etc. Thus, in certain embodiments, the present multi-phase oral compositions are preferably free of acids, free of alcohols, or free of a mixture thereof. In certain embodiments, the hydrophobic phase of the multi-phase oral composition may be substantially free of ingredients that may compromise the efficacy, usage experience, concentration of actives or bleaching agent at the tooth surface over time, active or bleaching efficiency, or compatibility between ingredients, for example bleaching agent. In certain embodiments, a multi-phase oral composition may be substantially free of ingredients that may compromise the efficacy, usage experience, concentration of actives or bleaching agent at the tooth surface over time, active or bleaching efficiency, or compatibility between ingredients, for example fumed silica, polyorganosiloxanes, copolymer condensation products of silicone resins and polydiorganosiloxanes, solid ingredients, or combinations thereof. In certain embodiments, the multi-phase oral composition may be substantially free of fumed silica since it may decrease the stability of the bleaching agent, especially if the bleaching agent is in a liquid form or dissolved in a liquid.

Additional Ingredients of the Multi-Phase Oral Composition
Thickening Agents, Viscosity Modifiers, or Particulate Fillers The multi-phase oral compositions herein may comprise a safe and effective amount of a thickening agent, viscosity modifier or particulate fillers. A thickening agent may further provide acceptable rheology of the composition. The viscosity modifier may further function to inhibit settling and separation of components or control settling in a manner that facilitates re-dispersion and may control flow properties of the composition. In addition, a thickening agent or viscosity modifier may facilitate use of the present compositions with suitable applications devices, such as strips, films or dental trays by increasing the retention onto the surfaces of the application devices. The thickening agent, as described herein, may also serve as an adhesive.

When present a thickening agent, viscosity modifier, or particulate filler may be present at a level of from about 0.01% to about 99%, from about 0.1% to about 50%, from about 1% to about 25%, or from about 1% to about 10%, by weight of the multi-phase oral composition.

Suitable thickening agents, viscosity modifiers, or particulate fillers that can be used herein include organo modified clays, silicas, synthetic polymers such as crosslinked siloxanes, cellulose derivatives (e.g. methylcellulose, carboxymethylcellulose, hydroxyethylcellulose, hydroxypropylcellulose, hydroxy-propylmethylcellulose, etc.), carbomer polymers (e.g. crosslinked polyacrylic acid copolymer or homopolymer and copolymers of acrylic acid cross linked with a polyalkenyl polyether), natural and synthetic gums, karaya gum, guar gum, gelatin, algin, sodium alginate, tragacanth, chitosan, polyethylene oxide, acrylamide polymers, polyacrylic acid, polyvinyl alcohol, polyamines, polyquarternary compounds, ethylene oxide polymers, polyvinylpyrrolidone, cationic polyacrylamide polymers, waxes (which includes paraffin wax and microcrystalline waxes), polyethylene, fumed silica, polymethacrylates, olefin copolymers, hydrogenated styrene-diene copolymers, styrene polyesters, rubber, polyvinylchloride, nylon, fluorocarbon, polyurethane prepolymer, polyethylene, polystyrene, alkylated polystyrene, polypropylene, cellulosic resins, acrylic resins, elastomers, poly(n-butyl vinyl ether), poly(styrene-co-maleic anhydride), poly(alkyl fumarate co-vinyl acetate), poly(t-butyl styrene), and mixtures thereof.

Examples of polyethylene include A-C 1702 or A-C 6702 made by Honeywell Corp. (Morristown, NJ), with a penetration value of about 98.5 and about 90.0, respectively, under ASTM D-1321; polyethylene Performalene series from Baker Hughes; this includes polyethylene Performalene 400 from Baker Hughes Inc. (Houston, TX). Examples of microcrystalline wax include the Multiwax series from Sonneborn (Parsippany, NJ), Crompton (Witco); these include Multiwax 835, Multiwax 440, Multiwax 180, and mixtures thereof.

Examples of polymethacyrlates include, for example, polyacrylate-co-methacrylate, polymethacrylate-co-styrene, or combinations thereof. Examples of elastomers include, for instance, hydrogenated styrene-co-butadiene, hydrogenated styrene-co-isoprene, ethylene-ethylene-propylene polymer, ethylene-propylene polymer, styrene-ethylene-ethylene-propylene-styrene polymer or combinations thereof. An example of a rubber includes hydrogenated polyisoprene. Other examples of viscosity modifiers can be found in "Chemistry and Technology of Lubricants," Chapman and Hall ($2^{nd}$ Ed. 1997).

Suitable carbomers comprises the class of homopolymers of acrylic acid crosslinked with an alkyl ether of pentaerythritol or an alkyl ether of sucrose. Carbomers are commercially available from B.F. Goodrich as the Carbopol® series, such as Carbopol 934, 940, 941, 956, and mixtures thereof. Homopolymers of polyacrylic acid are described, for example, in U.S. Pat. No. 2,798,053. Other examples of homopolymers which are useful include Ultrez 10, ETD 2050, and 974P polymers, which are available from The B.F. Goodrich Company (Greenville, SC). Such polymers are homopolymers of unsaturated, polymerizable carboxylic monomers such as acrylic acid, methacrylic acid, maleic acid, itaconic acid, maleic anhydride, and the like.

Optional Additional Oral Care Active Agents

The composition of the present invention may comprise a safe and effective amount of an additional oral care active agent, such as any material that is generally considered safe for use in the oral cavity and that provides changes to the overall appearance or health of the oral cavity. Suitable additional oral care actives include one or more anticalculus agent(s), fluoride ion source, antimicrobial agent(s), dentinal desensitizing agent(s), anesthetic agent(s), antifungal agent(s), anti-inflammatory agent(s), selective H-2 antagonist(s), anticaries agent(s), nutrient(s), erythritol, probiotics, and mixtures thereof. The additional oral care active agent may contain an active at a level where upon directed use the benefit sought by the wearer is promoted without detriment to the oral surface to which it is applied. Examples of the oral conditions these actives address include, but, are not limited to, appearance and structural changes to teeth, stain removal, plaque removal, tartar removal, cavity prevention and treatment, inflamed and/or bleeding gums, mucosal wounds, lesions, ulcers, aphthous ulcers, cold sores, tooth abscesses, and the elimination of mouth malodor resulting from the conditions above and other causes, such as microbial proliferation. In certain embodiments, the level of the additional oral care active that may be used in the multi-phase oral compositions may be from about 0.01% to about 50%, from about 0.1% to about 20%, from about 0.5% to about 10%, or from about 1% to about 7%, by weight of the multi-phase oral composition or any other numerical range, which is narrower, and which falls within such broader numerical range, as if such narrower numerical ranges were all expressly written herein.

In certain embodiments, the additional oral care active agent may be a healing agent that promotes or enhances the healing or regenerative process. In certain embodiments, such healing agents may comprise hyaluronic acid or salts, glucosamine or salts, allantoin, curcumin, D panthenol, niacinamide, ellagic acid, flavanoids (including fisetin, querctin, luteolin, apigenin), vitamin E, ubiquinone, or mixtures thereof.

In certain embodiments, the additional oral care active agent may be one or more probiotics selected from *Lactobacillus reuteri* ATCC 55730; *Lactobacillus salivarius* strain TI12711 (LS 1); *Lactobacillus paracasei* ADP-1; *Streptococcus salivarius* K12; *Bifidobacterium* DN-173 010; Filtrate of *L. paracasei* strain (pro-t-action™); *S. Oralis* KJ3, *S. rattus* JH145, *S. uberis* KJ2; *Lactobacillus, reuteri* Prodentis; *Lactobacillus salivarius* LS1; *Lactobacillus paracasei*; *Lactobacillus paracasei* ADP1; *Streptococcus salivarius* M18, K12 or BLIS K12 and BLIS M18; *Bacillus amyloliquefaciens*; *Bacillus clausii*; *Bacillus coagulans*; *Bacillus subtilis*; *Bacillus subtilis*: E-300; *Bifidobacterium animalis*; *Bifidobacterium* B6; *Bifidobacterium bifidum*; *Bifidobacterium breve* (Bb-03); *Bifidobacterium* DN-173 010; *Bifidobacterium* GBI 30 6068; *Bifidobacterium infantis*; *Bifidobacterium Lactis*; *Bifidobacterium lactis* Bb-12; *Bifidobacterium longum*; *Bifidobacterium thermophilum*; *Enterococcus faecalis*; *Enterococcus Faccium*; *Enterococcus Faccium* NCIMB 10415; *Enterococcus* LAB SF 68; *Lactobacilli reuteri* ATCC 55730 and ATCC PTA 5289; *Lactobacilli reuteri* ATCC 55730 and ATCC PTA 5289 (10:1); *Lactobacillus Acidophilus*; *Lactobacillus acidophilus* ATCC 4356 and *Bifidobacterium bifidum* ATCC 29521; *Lactobacillus acidophilus*; *Bifidobacterium longum*; *Bifidobacterium bifidum*; *Bifidobacterium lactis*; *Lactobacillus brevis*; *Lactobacillus casei* (subsp. *Casi*); *Lactobacillus casei* Shirota; *Lactobacillus confusus*; *Lactobacillus crispatus* YIT 12319; *Lactobacillus curvatus*; *Lactobacillus delbrueckii* Ssp. *Bulgaricus* PXN 39; *Lactobacillus fermentum*; *Lactobacillus fermentum* YIT 12320; *Lactobacillus* Gasseri; *Lactobacillus* gasseri YIT 12321; *Lactobacillus Helveticus*; *Lactobacillus johnsonii*; *Lactobacillus kimchii*; *Lactobacillus lactis* LIA; *Lactobacillus paracasei* (Lpc37); *Lactobacillus paracasei* GMNL-33; *Lactobacillus pentosus*; *Lactobacillus plantarum*; *Lactobacillus plantarum*; *Lactobacillus protectus*; *Lactobacillus reuteri*; *Lactobacillus reuteri* ATCC 55730; *Lactobacillus reuteri* SD2112 (ATCC55730); *Lactobacillus rhamnosus* (GG); *Lactobacillus rhamnosus* GG; *Lactobacillus rhamnosus* GG; *L. rhamnosus* LC705; *Propionibacterium freudenreichii* ssp; *shermanii* JS; *Lactobacillus rhamnosus* L8020; *Lactobacillus rhamnosus* LB21; *Lactobacillus Salivarius*; *Lactobacillus salivarius* WB21; *Lactobacillus sporogenes*; *Lactococcus lactis* Ssp Diacetylactis; *Lactococcus lactis* Ssp. *Lactis*; *Pediococcus acidilactici*; *Pediococcus pentosaceus*; *Saccharomyces boulardii*; *Saccharomyces cerevisiae*; *Strep. uberis* KJ2sm; *Strep. oralis* KJ3sm; trep. *rattus* JH145; *Streptococcus mitis* YIT 12322; *Streptococcus oralis* KJ3; *Streptococcus rattus* JH145; *Streptococcus salivarius* (BLIS K12 or BLIS M18); *Streptococcus salivarius* K12; *Streptococcus thermophilus*; *Streptococcus uberis* KJ2; *Thermus* thermophiles; *Weissella cibaria* CMS2; *Weissella cibaria* CMS3; and *Weissella cibaria* CMU.

Probiotics can be used in the multi-phase oral compositions of the present invention to promote positive oral health effects, such as reduce caries and plaque, promote gum health, improve breath, and promote whitening. In certain embodiments, the efficacy of probiotics in the multi-phase oral compositions can be determined by measuring one or more of the following: reduction of the levels of salivary *mutans* streptococci; reduction of gingival crevicular fluid; reduction of periodontal pathogens (*C. rectus* and *P. gingivitis*) in subgingival plaque; decreased counts of yeast; decreased prevalence of oral *candida*; reduction of oral volatile sulfur compound (VSC) levels; and reduction of TNF-$\alpha$ and IL-8 production. Without being limited to theory it is believed that one or more of the above positive oral health effects may be achieved through the production of bacterial toxins, which remove or reduce certain types of bacteria in the oral cavity; further one or more of the above positive oral health effects may be achieved through bacterial production of one or more enzymes that inhibit the production of or dissolves/loosens biofilms or sticky deposits that can lead to oral health problems.

As the present multi-phase oral composition is directed to bleaching the tooth surface and removing or decreasing the stain attached thereto, in certain embodiments a safe and effective amount may be added of at least one anticalculus agent to the compositions as disclosed herein. In certain amounts, said amount may be from about 0.01% to about 40%, from about 0.1% to about 25%, from about 4.5% to about 20%, or from about 5% to about 15%, by weight of the multi-phase oral composition or any other numerical range, which is narrower, and which falls within such broader numerical range, as if such narrower numerical ranges were all expressly written herein. The anticalculus agent may also be compatible with the other components of the multi-phase oral composition, in particular the whitening agent. The anticalculus agent may be selected from the group consisting of polyphosphates and salts thereof; polyamino propane sulfonic acid (AMPS) and salts thereof; polyolefin sulfonates and salts thereof; polyvinyl phosphates and salts thereof; polyolefin phosphates and salts thereof; diphosphonates and salts thereof; phosphonoalkane carboxylic acid and salts thereof; polyphosphonates and salts thereof; polyvinyl phosphonates and salts thereof; polyolefin phosphonates and salts thereof; polypeptides; and mixtures thereof, wherein the mentioned salts are usually alkali metal salts. In certain embodiments anticalculus agents used in the present multi-phase oral composition also show a stabilizing effect to the bleaching agents, such as pyrophosphates, polyphosphates, polyphophonates and mixtures thereof.

For example, the anticalculus agent may be a polyphosphate. A polyphosphate is generally understood to comprise two or more phosphate molecules arranged primarily in a linear configuration, although some cyclic derivatives may be present. Linear polyphosphates correspond to $(X\ PO_3)_n$ where n is about 2 to about 125, wherein preferably n is greater than 4, and X is for example sodium, potassium, etc. For $(X\ PO_3)_n$ when n is at least 3 the polyphosphates are glassy in character. Counter-ions for these phosphates may be the alkali metal, alkaline earth metal, ammonium, $C_2$-$C_6$ alkanolammonium and salt mixtures. Polyphosphates are generally employed as their wholly or partially neutralized water soluble alkali metal salts such as potassium, sodium, ammonium salts, and mixtures thereof. The inorganic polyphosphate salts include alkali metal (e.g. sodium) tripolyphosphate, tetrapolyphosphate, dialkyl metal (e.g. disodium) diacid, trialkyl metal (e.g. trisodium) monoacid, potassium hydrogen phosphate, sodium hydrogen phosphate, and alkali metal (e.g. sodium) hexametaphosphate, and mixtures thereof. Polyphosphates larger than tetrapolyphosphate usually occur as amorphous glassy materials, such as those manufactured by FMC Corporation which are commercially known as Sodaphos (n≈6), Hexaphos (n≈13), Glass H (n≈21), and mixtures thereof. If present, the present compositions will typically comprise from about 0.5% to about 20%, in particular from about 4% to about 15%, more particular from about 6% to about 12%, by weight of the composition of polyphosphate.

The pyrophosphate salts useful in the present compositions include, alkali metal pyrophosphates, di-, tri-, and mono-potassium or sodium pyrophosphates, dialkali metal pyrophosphate salts, tetraalkali metal pyrophosphate salts, and mixtures thereof. For example, the pyrophosphate salt is selected from the group consisting of trisodium pyrophosphate, disodium dihydrogen pyrophosphate ($Na_2H_2P_2O_7$), dipotassium pyrophosphate, tetrasodium pyrophosphate ($Na_4P_2O_7$), tetrapotassium pyrophosphate ($K_4P_2O_7$), and mixtures thereof, wherein tetrasodium pyrophosphate is preferred. Tetrasodium pyrophosphate may be the anhydrous salt form or the decahydrate form, or any other species stable in solid form in the present compositions. The salt is in its solid particle form, which may be its crystalline and/or amorphous state, with the particle size of the salt preferably being small enough to be aesthetically acceptable and readily soluble during use. The level of pyrophosphate salt in the present compositions may be from about 1.5% to about 15%, in particular from about 2% to about 10%, and more particular from about 3% to about 8%, by weight of the composition.

The phosphate sources, including but are not limited to, polyphosphates and pyrophosphates, are described in more detail in Kirk & Othmer, *Encyclopedia of Chemical Technology*, Fourth Edition, Volume 18, Wiley-Interscience Publishers (1996), pages 685-707, incorporated herein by reference in its entirety, including all references incorporated into Kirk & Othmer.

Polyolefin phosphonates include those wherein the olefin group contains 2 or more carbon atoms. Polyvinylphosphonates include polyvinylphosphonic acid. Diphosphonates and salts thereof include azocycloalkane-2,2-diphosphonic acids and salts thereof, ions of azocycloalkane-2,2-diphosphonic acids and salts thereof (such as those which the alkane moiety has five, six or seven carbon atoms, in which the nitrogen atom is unsubstituted or carries a lower alkyl substitutent, e.g. methyl), azacyclohexane-2,2-diphosphonic acid, azacyclopentane-2,2-diphosphonic acid, N-methyl-azacyclopentane-2,3-diphosphonic acid, EHDP (ethanehydroxy-1,1,-diphosphonic acid), AHP (azacycloheptane-2,2-diphosphonic acid, a.k.a. 1-azocycloheptylidene-2,2-diphosphonic acid), ethane-1-amino-1,1-diphosphonate, dichloromethane-diphosphonate, etc. Phosphonoalkane carboxylic acid or their alkali metal salts include PPTA (phosphonopropane tricarboxylic acid), PBTA (phosphonobutane-1,2,4-tricarboxylic acid), each as acid or alkali metal salts.

In addition, antimicrobial antiplaque agents may also be present in the present compositions. Such agents may include, but are not limited to, triclosan, 5-chloro-2-(2,4-dichlorophenoxy)-phenol, as described in The Merck Index, 11th ed. (1989), pp. 1529 (entry no. 9573) in U.S. Pat. No. 3,506,720, and in European Patent Application No. 0,251,591; chlorhexidine (Merck Index, no. 2090), alexidine (Merck Index, no. 222; hexetidine (Merck Index, no. 4624); sanguinarine (Merck Index, no. 8320); benzalkonium chloride (Merck Index, no. 1066); salicylanilide (Merck Index, no. 8299); domiphen bromide (Merck Index, no. 3411); cetylpyridinium chloride (CPC) (Merck Index, no. 2024; tetradecylpyridinium chloride (TPC); N-tetradecyl-4-ethylpyridinium chloride (TDEPC); octenidine; delmopinol, octapinol, and other piperidino derivatives; In addition there may be effective antimicrobial amounts of essential oils and combinations thereof for example citral, geranial, and combinations of menthol, eucalyptol, thymol and methyl salicylate; antimicrobial metals and salts thereof for example those providing zinc ions, stannous ions, copper ions, and/or mixtures thereof; bisbiguanides, or phenolics; antibiotics such as augmentin, amoxicillin, tetracycline, doxycycline, minocycline, and metronidazole; and analogs and salts of the above antimicrobial antiplaque agents and/or anti-fungals such as those for the treatment of *Candida albicans*. If present, these agents generally are present in a safe and effective amount for example from about 0.1% to about 5% by weight of the present compositions.

In addition, the present composition may comprise a safe and effective amount of an anticaries agent, and mixtures thereof. The anticaries agent may be selected from the group consisting of xylitol, fluoride ion source providing free fluoride ions, and mixtures thereof. In certain embodiments, a fluoride ion source may be selected from the group consisting of sodium fluoride, stannous fluoride, indium fluoride, organic fluorides such as amine fluorides, and sodium monofluorophosphate, wherein sodium fluoride is preferred. Preferably the instant compositions provide from about 50 ppm to 10,000 ppm, more preferably from about 100 to 3000 ppm, of fluoride ions in the compositions that contact dental surfaces when used with the composition as disclosed herein.

In addition, coolants, desensitizing agents and numbing agents can be used as optional ingredients in compositions of the present invention, in particular at a level of from about 0.001% to about 10%, more particular from about 0.1% to about 1%, by weight of the composition. Coolants, desensitizing agents and numbing agents may decrease potential negative perceptions, such as tingling, burning etc. Coolant can be any of a wide variety of materials. Included among such materials are carboxamides, menthol, ketals, diols, and mixtures thereof. Optional coolants in the present compositions may be the paramenthan carboxyamide agents such as N-ethyl-p-menthan-3-carboxamide (known as "WS-3"), N,2,3-trimethyl-2-isopropylbutanamide (known as "WS-23"), menthol, 3-1-menthoxypropane-1,2-diol (known as TK-10), menthone glycerol acetal (known as MGA) menthyl lactate (known as Frescolat®), and mixtures thereof. The terms menthol and menthyl as used herein include dextro- and levorotatory isomers of these compounds and racemic mixtures thereof. Desensitizing or Anti-pain agent may include, but are not limited to, strontium chloride, potassium nitrate, natural herbs such as gall nut, Asarum, Cubebin, Galanga, scutellaria, Liangmianzhen, Baizhi, etc. Suitable numbing agents include benzocaine, lidocaine, clove bud oil, and ethanol.

In addition, anti-inflammatory agents may be present in the multi-phase oral compositions as disclosed herein. Such agents may include, but are not limited to, non-steroidal anti-inflammatory agents such as aspirin, ketorolac, flurbiprofen, ibuprofen, naproxen, indomethacin, aspirin, ketoprofen, piroxicam and meclofenamic acid, COX-2 inhibitors such as valdecoxib, celecoxib and rofecoxib, and mixtures thereof. If present, the anti-inflammatory agents generally comprise from about 0.001% to about 5% by weight of the compositions.

In addition, nutrients, such as minerals, may improve the teeth and the tooth surface and thus can be included with the compositions as disclosed herein. Suitable minerals are e.g. calcium, phosphorus, fluoride, zinc, manganese, potassium and mixtures thereof. These minerals are e.g disclosed in Drug Facts and Comparisons (loose leaf drug information service), Wolters Kluer Company, St. Louis, Mo., ©1997, pp 10-17.

In addition, the compositions as disclosed herein may optionally comprise a safe and effective amount of a flavoring agent. Suitable flavoring agents include oil of wintergreen, oil of peppermint, oil of spearmint, clove bud oil, menthol, anethole, methyl salicylate, cucalyptol, 1-menthyl acetate, sage, eugenol, parsley oil, oxanone, alpha-irisone, marjoram, lemon, orange, propenyl guaethol, cinnamon, vanillin, thymol, linalool, cinnamaldehyde glycerol acetal (known as CGA), and mixtures thereof. If present the flavoring agents are generally used at levels of from about 0.01% to about 30%, in particular from about 1% to about 20%, more particular from about 1.5% to about 15%, by weight of the composition.

In addition, the present compositions may optionally comprise sweetening agents including sucralose, sucrose, glucose, saccharin, dextrose, levulose, lactose, mannitol, sorbitol, fructose, maltose, xylitol, saccharin salts, thaumatin, aspartame, D-tryptophan, dihydrochalcones, acesulfame and cyclamate salts, especially sodium cyclamate and sodium saccharin, and mixtures thereof. If present, the composition contains from about 0.1% to about 10% of these agents, in particular from about 0.1% to about 1%, by weight of the composition.

In addition, dyes, pigments, colorants, and mixtures thereof may optionally be included in the present composition to give the compositions herein colored appearance. An advantage of adding pigments and/or colorants to the compositions herein is that it will allow the user to see if the composition covers their teeth evenly and completely, since coverage is easier to see with a colored composition. In addition, the colorant may provide color similar to the color of bleached teeth. Colorants useful herein are stable with the bleach agent and are those recognized as safe. The levels of dye, pigments and colorants that are optionally used herein are in the range of about 0.05% to about 20%, in particular from about 0.10% to about 15% and more particular from about 0.25% to about 5% by weight of the composition.

Bleaching Efficacy

In certain embodiments, the bleaching efficacy of the present invention, as measured per the clinical protocol, as disclosed herein and calculated as $-\Box b^*$ may be at least about, 0.25, 0.5, 1, 1.5. 2, 2.5, 3, 4, 5, 6, 7, 8, 9 or 10 or any other numerical range, which is narrower and which falls within such broader numerical range, as if such narrower numerical ranges were all expressly written herein.

In certain embodiments, the bleaching efficacy of the present invention, as measured per the clinical protocol as disclosed herein, and calculated as $-\Box b^*$ may be at least about 0.25, preferably at least about 0.5, more preferred at least about 1.0, even more preferred at least about 1.5, even more preferred at least about 2, even more preferred at least about 2.5, even more preferred at least about 3, even more preferred at least about 3.5, and even more preferred at least about 4, or any other numerical range, which is narrower and which falls within such broader numerical range, as if such narrower numerical ranges were all expressly written herein. Generally, a change in yellowness, as measured per the clinical protocol as disclosed herein, and calculated as $-\Box b^*$ of at least 0.25 is noticeable.

It has been found that the present invention delivers a surprisingly high ratio of bleaching efficacy of the present invention, as measured per the clinical protocol as disclosed herein, and calculated as $-\Delta b^*$ to the weight percent of bleaching agent present in the overall multi-phase oral composition.

In certain embodiments, the ratio of bleaching efficacy of the present invention, as measured per the clinical protocol as disclosed herein, and calculated as $-\Box b^*$ to the weight percent of bleaching agent present in the overall multi-phase oral composition may be at least about, 0.25, 0.5, 1, 1.5. 2, 2.5, 5, 10, or 15 or any other numerical range, which is narrower and which falls within such broader numerical range, as if such narrower numerical ranges were all expressly written herein.

In certain embodiments, the bleaching efficacy of the present invention, as measured per the clinical protocol, as disclosed herein and calculated as $-\Box b^*$ may be at least about 10%, at least about 100%, at least about 1000%, or at least about 10,000% more than the bleaching efficacy of a comparative oral care composition in the form of an aqueous solution or aqueous gel. The comparative oral care composition comprises the same bleaching agent at the same overall concentration dissolved into the aqueous solution or aqueous gel.

It has been found that the present invention delivers: 1) a surprisingly high ratio of bleaching efficacy, as measured per the clinical protocol as disclosed herein, and calculated as $-\Delta b^*$ to the fraction of participants who reported oral irritation or were observed to have oral irritation that was possibly or probably attributed to the composition tested; 2) a surprisingly high ratio of bleaching efficacy of the present invention, as measured per the clinical protocol as disclosed herein, and calculated as $-\Delta b^*$ treatments to the fraction of participants who reported tooth sensitivity that was possibly or probably attributed to the composition; or 3) a surprisingly high ratio of bleaching efficacy of the present invention, as measured per the clinical protocol as disclosed herein, and calculated as $-\Delta b^*$ to the fraction of participants who reported tooth sensitivity or reported oral irritation or were observed to have oral irritation that was possibly or probably attributed to the composition.

In certain embodiments, the ratio of bleaching efficacy of the present invention, as measured per the clinical protocol as disclosed herein, and calculated as −□b* to the fraction of participants who report tooth sensitivity that is possibly or probably attributed to the present invention may be at least about 6, 7, 8, 9, 10, 15, 20, 25, 50, or 100 or any other numerical range, which is narrower and which falls within such broader numerical range, as if such narrower numerical ranges were all expressly written herein.

In certain embodiments, the ratio of bleaching efficacy of the present invention, as measured per the clinical protocol as disclosed herein, and calculated as −□b* to the fraction of participants who report tooth sensitivity that is possibly or probably attributed to the present invention may be at least about 6, preferably at least about 7, more preferred at least about 8, even more preferred at least about 9, even more preferred at least about 10, even more preferred at least about 15, even more preferred at least about 20, even more preferred at least about 25, and even more preferred at least about 50, or any other numerical range, which is narrower and which falls within such broader numerical range, as if such narrower numerical ranges were all expressly written herein.

In certain embodiments, the ratio of bleaching efficacy of the present invention, as measured per the clinical protocol as disclosed herein, and calculated as −□b* to the fraction of participants who report oral irritation or are observed to have oral irritation that is possibly or probably attributed to the present invention may be at least about 6, 7, 8, 9, 10, 15, 20, 25, 50, or 100 or any other numerical range, which is narrower and which falls within such broader numerical range, as if such narrower numerical ranges were all expressly written herein.

In certain embodiments, the ratio of bleaching efficacy of the present invention, as measured per the clinical protocol as disclosed herein, and calculated as −□b* to the fraction of participants who report oral irritation or are observed to have oral irritation that is possibly or probably attributed to the present invention may be at least about 6, preferably at least about 7, more preferred at least about 8, even more preferred at least about 9, even more preferred at least about 10, even more preferred at least about 15, even more preferred at least about 20, even more preferred at least about 25, and even more preferred at least about 50, or any other numerical range, which is narrower and which falls within such broader numerical range, as if such narrower numerical ranges were all expressly written herein.

In certain embodiments, the ratio of bleaching efficacy of the present invention, as measured per the clinical protocol as disclosed herein, and calculated as −□b* to the fraction of participants who report tooth sensitivity or report oral irritation or are observed to have oral irritation that is possibly or probably attributed to the present invention may be at least about 6, 7, 8, 9, 10, 15, 20, 25, 50, or 100 or any other numerical range, which is narrower and which falls within such broader numerical range, as if such narrower numerical ranges were all expressly written herein.

In certain embodiments, the ratio of bleaching efficacy of the present invention, as measured per the clinical protocol as disclosed herein, and calculated as −□b* to the fraction of participants who report tooth sensitivity or report oral irritation or are observed to have oral irritation that is possibly or probably attributed to the present invention may be at least about 6, preferably at least about 7, more preferred at least about 8, even more preferred at least about 9, even more preferred at least about 10, even more preferred at least about 15, even more preferred at least about 20, even more preferred at least about 25, and even more preferred at least about 50, or any other numerical range, which is narrower and which falls within such broader numerical range, as if such narrower numerical ranges were all expressly written herein.

Clinical Protocol

The bleaching efficacies of the multi-phase oral compositions are measured using the following clinical protocol. Per treatment group, 17 to 25 participants are recruited to complete the clinical study when testing compositions with less than about 1% bleaching agent, and 8 to 25 participants when testing compositions with at least about 1% bleaching agent. Recruited participants must have four natural maxillary incisors with all measurable facial sites. The mean baseline L* of the group of participants must be from 71 to 76, and the mean baseline b* of the group of participants must be from 13 to 18. In addition, participants with malocclusion on maxillary anterior teeth, severe or atypical intrinsic staining, such as that caused by tetracycline, fluorosis or hypo-calcification, dental crowns or restorations on the facial surfaces of maxillary anterior teeth, self-reported medical history of melanoma, current smoking or tobacco use, light-sensitivity or a pigmentation skin disorder, self-reported tooth sensitivity, or previous tooth whitening using a professional treatment, over-the-counter kit, or investigational product, are excluded from the study. Participants are provided with take-home kits with Crest Cavity Protection toothpaste and Oral-B Indicator soft manual toothbrush (both from Procter & Gamble, Cincinnati, OH, USA) to be used twice a day in the customary manner.

The participants use a toothbrush ("Anchor 41 tuft white toothbrush" from Team Technologies, Inc. Morristown, TN, USA) to brush their teeth with water for 30 seconds prior to being treated with the multi-phase oral composition. The maxillary anterior teeth of each participant are treated with the multi-phase oral composition for 60 minutes once daily using a strip of polyethylene as a delivery carrier. The polyethylene strips are 66 mm×15 mm in size and 0.0178 mm thick. From 0.6 g to 0.8 g of the multi-phase oral composition is applied across each strip of polyethylene prior to applying to the maxillary anterior teeth.

Figure 6:
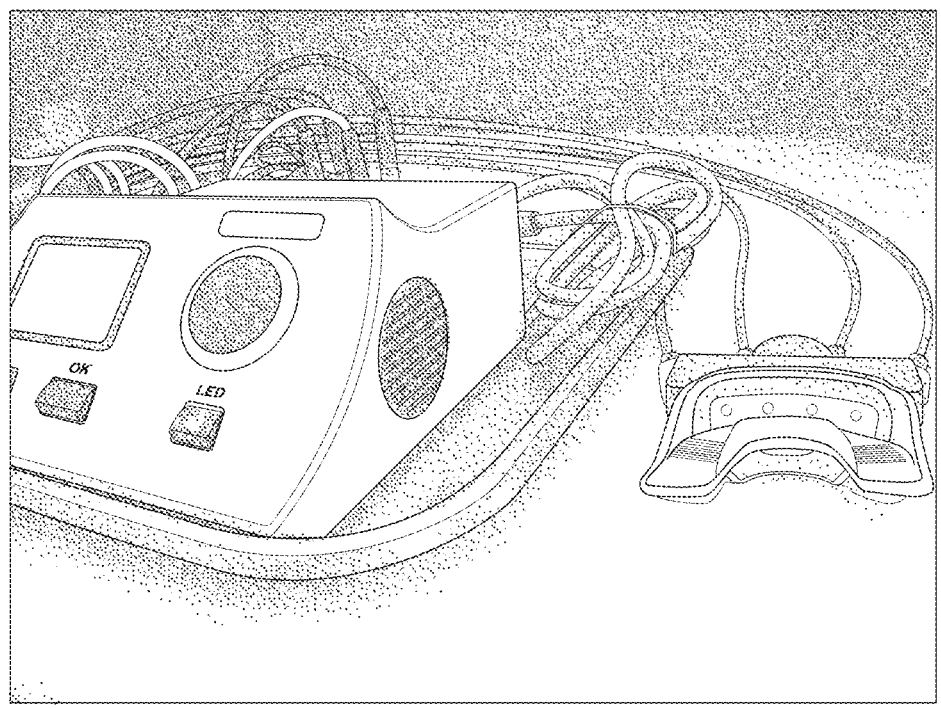
FIG. 6 shows a device for delivering electromagnetic radiation with a peak intensity wavelength of about 455 nm to a transparent mouthpiece to help position the electromagnetic radiation reproducibly toward the tooth surface; according to certain embodiments of the present invention.

If the multi-phase oral composition is used with electromagnetic radiation:
1) After 50 minutes of treatment with the multi-phase multi-phase oral composition on the strip, the electromagnetic radiation is applied toward the facial surfaces of the maxillary anterior teeth for 10 minutes,
2) The electromagnetic radiation is directed toward the maxillary anterior teeth through the strip and through the multi-phase multi-phase oral composition,
3) The strip needs to allow at least about 90% of the electromagnetic radiation from 400 nm to 500 nm to pass through, and
4) The electromagnetic radiation is delivered via four fiber-optic cables (model number M71L01 from Thorlabs, Newton, NJ, USA) connected to four high power LEDs with a peak intensity wavelength of 455 nm (model number M455F1 from Thorlabs, Newton, NJ, USA) as shown in FIG. 6. The four LEDs are run at 1000 mA each using an LED Driver and Hub (model numbers DC4104 and DC4100-HUB from Thorlabs, Newton, NJ, USA). The exit ends of the four fiber-optic cables are mounted behind a transparent mouthpiece to help position the electromagnetic radiation reproducibly against the outer surface of the strip. The exit ends of the four fiber-optic cables are about 7 mm away from the exit surface of the mouthpiece with the electromagnetic radiation passing through the transparent mouthpiece. The bite-shelf of the mouthpiece is offset such that the transparent window through which the electromagnetic radiation passes toward the maxillary anterior teeth is 7.4 mm high. Also, the transparent window through which the electromagnetic radiation passes toward the maxillary anterior teeth is 40 mm long measured linearly from end to end (not including the curvature). The exit ends of the fiber-optic cables are positioned & angled such that the cones of electromagnetic radiation exiting from the fiber-optic cables are centered within the transparent window through which the electromagnetic radiation passes toward the maxillary anterior teeth as shown in FIG. 6. Also, the exit ends of the four fiber-optic cables are spaced such that the cones of electromagnetic radiation are spaced across the length of the transparent window through which the electromagnetic radiation passes toward the maxillary anterior teeth as shown in FIG. 6. The intensity of the electromagnetic radiation from 400 nm to 500 nm measured at the central axis of each cone of electromagnetic radiation exiting at the exit surface of the transparent window through which the electromagnetic radiation passes toward the maxillary anterior teeth needs to be from about 175 mW/cm$^2$ to about 225 mW/cm$^2$ as measured by the method disclosed herein.

Once 60 minutes of the treatment with the multi-phase oral composition is completed, the strip is removed. This treatment is applied once daily for a minimum of 7 days for compositions with less than about 1% bleaching agent, and a minimum of 3 days for compositions with at least about 1% bleaching agent.

The change in tooth color due to the treatment with the multi-phase oral composition is measured using the procedure described below the day after the 7$^{th}$ treatment for compositions with less than about 1% bleaching agent and after the 3$^{rd}$ treatment for compositions with at least about 1% bleaching agent.

Tooth color is measured using a digital camera having a lens equipped with a polarizer filter (Camera model no. CANON EOS 70D from Canon Inc., Melville, NY with NIKON 55 mm micro-NIKKOR lens with adapter). The light system is provided by Dedo lights (model number DLH2) equipped with 150 watt, 24V bulbs model number (Xenophot model number HL X64640), positioned about 30 cm apart (measured from the center of the external circular surface of one of the glass lens through which the light exits to the other) and aimed at a 45 degree angle, such that the light paths intersect at the vertical plane of the chin rest about 36 cm in front of the focal plane of the camera. Each light has a polarizing filter (Lee 201 filter), and a cutoff filter (Rosco 7 mil Thermashield filter from Rosco, Stamford, CT, USA).

At the intersection of the light paths, a fixed chin rest is mounted for reproducible repositioning in the light field. The camera is placed between the two lights such that its focal plane is about 36 cm from the vertical plane of the chin rest. Prior to beginning the measurement of tooth color, color standards are imaged to establish calibration set-points. A Munsell N8 grey standard is imaged first. The white balance of the camera is adjusted, such that the RGB values of grey are 200. Color standards are imaged to get standard RGB values of the color chips. The color standards and grey standard are listed below (from Munsell Color, Division of X-rite, Grand Rapids, MI, USA). Each color standard is labeled with the Munsell nomenclature. To create a grid of color standards they can be arranged in the following manner. This enables multiple color standards to be contained in a single image captured of the grid of color standards.

Color Standard Grid 1

| 7.5R 6 8 | 2.5R 6 10 | 10YR 6.5 3 | POLARIZATION CHECK | 5R 7 8 | N 3.5 0 |
|---|---|---|---|---|---|
| 7.5RP 6 6 | 10R 5 8 | 5YR 7 3 | 2.5Y 8.5 2 | 2.2YR 6.47 4.1 | 7.5YR 7 4 |
| 5YR 8 2 | N 8 0 | 10R 7 4 | N 8 0 | 5YR 7.5 2.5 | 2.5Y 8 4 |
| 5YR 7 3.5 | 5YR 7 2.5 | 5YR 5 2 | 5YR 7.5 2 | N 6.5 0 | N 9.5 0 |

Color Standard Grid 2

| 5YR 7.5 3.5 | 2.5Y 6 4 | 10YR 7.5 3.5 | 2.5R 7 8 | 7.5R 7 8 | 10YR 7.5 2 |
|---|---|---|---|---|---|
| 10YR 7.5 2.5 | N 5 0 | 2.5R 6 8 | 10YR 7 2 | 5R 7 4 | 10YR 7 2.5 |
| N 6.5 0 | 7.5RP 6 8 | 7.5R 8 4 | 5Y 8 1 | 7.5YR 8 2 | 2.2YR 6.47 4.1 |
| N 5 0 | 2.5Y 8 4 | 10YR 7 3 | N 9.5 0 | 10RP 7 4 | 2.5Y 7 2 |

Color Standard Grid 3

| 5R 6 10 | N 8.5 0 | 10YR 6.5 3.5 | 10RP 6 10 | N 8 0 | 7.5YR 7 3 |
|---|---|---|---|---|---|
| 2.5Y 3.5 0 | 10YR 7 3.5 | 5Y 8.5 1 | 5YR 8 2.5 | 5YR 7.5 3 | 5R 5 6 |
| 10YR 7.5 3 | 5YR 6.5 3.5 | 2.5YR 5 4 | 2.5Y 8 2 | 10YR 8 2 | 2.5Y 7 2 |
| 2.5R 6 6 | 5R 7 6 | 10YR 8 2.5 | 10R 5 6 | N 6.5 0 | 7.5YR 8 3 |

For baseline tooth color, participants use a toothbrush ("Anchor 41 tuft white toothbrush" from Team Technologies, Inc. Morristown, TN, USA) to brush their teeth with water to remove debris from their teeth. Each participant then uses check retractors (from Washington Scientific Camera Company, Sumner, WA, USA; treated with at frosted matte finish at A&B Deburring Company, Cincinnati, OH, USA) to pull the cheeks back and allow the facial surfaces of their teeth to be illuminated. Each participant is instructed to bite their teeth together such that the incisal edges of the maxillary incisors contact the incisal edges of the mandibular incisors. The participants are then positioned on the chin rest at the intersection of the light paths in the center of the camera view and the tooth images are captured. After all participants are imaged, the images are processed using image analysis software (Optimas manufactured by Media Cybernetics, Inc. of Silver Spring, MD). The central four incisors are isolated and the average RGB values of the teeth are extracted.

After the participants have used a whitening product, but prior to capturing participant's tooth images, the system is set to the baseline configuration and calibrated as previously discussed. After calibration, each participant is imaged a second time using the same procedure as before making sure the participant is in the same physical position as the pre-treatment image including orientation of the teeth. The images are processed using the image analysis software to obtain the average RGB values of the central four maxillary incisors. The RGB values of all of the images are then mapped into CIE L*'a*b* color space using the RGB values and the L*a*b* values of the color chips on the color standard. The L*a*b* values of the color chips on the color standard are measured using a Photo Research SpectraScan PR650 from Photo Research Inc., LA using the same lighting conditions described for capturing digital images of the facial dentition. The PR650 is positioned the same distance from the color standards as the camera. Each chip is individually measured for L*a*b* after calibration according to the manufacturer's instructions. The RGB values are then transformed into L*a*b* values using regression equations such as:

$$L^*=25.16+12.02^*(R/100)+11.75^*(G/100)-2.75^*(B/100)+1.95^*(G/100)^3$$

$$a^*=-2.65+59.22^*(R/100)-50.52^*(G/100)+0.20^*(B/100)-29.87^*(R/100)^2+20.73^*(G/100)^2+8.14^*(R/100)^3-9.17(G/100)^3+3.64^*[(B/100)^2]^*[R/100]$$

$$b^*=-0.70+37.04^*(R/100)+12.65^*(G/100)-53.81^*(B/100)-18.14^*(R/100)^2+23.16^*(G/100)^*(B/100)+4.70^*(R/100)^3-6.45^*(B/100)^3$$

The $R^2$ for L*, a*, and b* should be >0.95. Each study should have its own equations.

These equations are generally valid transformations in the area of tooth color (60<L*<95, 0<a*<14, 6<b*<25). The data from each participant's set of images is then used to calculate product whitening performance in terms of changes in L*, a* and b*—a standard method used for assessing whitening benefits. When evaluating compositions with less than about 1% bleaching agent: Changes in L* is defined as $\Delta L^*=L^*_{day\ after\ 7\ treatments}-L^*_{baseline}$ where a positive change indicates improvement in brightness; Changes in a* (red-green balance) is defined as $\Delta a^*=a^*_{day\ after\ 7\ treatments}-a^*_{baseline}$ where a negative change indicates teeth which are less red; Changes in b* (yellow-blue balance) is defined as $\Delta b^*=b^*_{day\ after\ 7\ treatments}-b^*_{baseline}$ where a negative change indicates teeth are becoming less yellow. When evaluating compositions with at least about 1% bleaching agent: Changes in L* is defined as $\Delta L^*=L^*_{after\ 3\ treatments}-L^*_{baseline}$ where a positive change indicates improvement in brightness; Changes in a* (red-green balance) is defined as $\Delta a^*=a^*_{after\ 3\ treatments}-a^*_{baseline}$ where a negative change indicates teeth which are less red; Changes in b* (yellow-blue balance) is defined as $\Delta b^*=b^*_{after\ 3\ treatments}-b^*_{baseline}$ where a negative change indicates teeth are becoming less yellow. $-\Delta b^*$ is used as the primary measure of bleaching efficacy. The overall color change is calculated by the equation $\Delta E=(\Delta L^{*2}+\Delta a^{*2}+\Delta b^{*2})^{1/2}$.

To validate the above clinical protocol, the bleaching efficacy (calculated as $-\Delta b^*$) of Example-IA (delivered on a strip and used with electromagnetic radiation as disclosed herein) needs to be measured the day after the $7^{th}$ treatment and demonstrated to be >0.5.

After using the whitening products, color changes in CIE Lab color space can be calculated for each participant based on the equations given.

To validate the above clinical protocol, the bleaching efficacy (calculated as $-\Delta b^*$) of Example-IA (delivered on a strip and used with electromagnetic radiation as disclosed herein) needs to be measured the day after the 7th treatment and demonstrated to be >0.5.

Optional Application Systems

In addition, the present invention may further relate to a delivery system for delivering the present compositions to the tooth surface. For example, in certain embodiments the compositions of the present invention may deliver whitening benefits to the oral cavity by being directly applied to the teeth without using a delivery carrier system. In addition, in certain embodiments the present invention may include a delivery system comprising the present compositions in combination with a delivery carrier. For example, the delivery system may comprise a first layer of a carrier material and a second layer comprising a multi-phase oral composition described herein, whereby the bleaching agent is releasably located within the present composition. A suitable first layer may comprise a delivery carrier including a strip of material, a dental tray, a sponge material, and mixtures thereof. In certain embodiments, the delivery carrier may be a strip of material, such as a permanently deformable strip. Suitable strips of material or permanently deformable strips are for example disclosed in U.S. Pat. Nos. 6,136,297; 6,096,328; 5,894,017; 5,891,453; and 5,879,691; and in U.S. Pat. Nos. 5,989,569 and 6,045,811; and in patent application US 2014/0178443 A1.

The delivery carrier may be attached to the teeth via an attachment means that is part of the delivery carrier, for example the delivery carrier may be of sufficient size that, once applied the delivery carrier overlaps with the oral soft tissues rendering more of the teeth surface available for bleaching. The delivery carrier may also be attached to the oral cavity by physical interference or mechanical interlocking between the delivery carrier and the oral surfaces including the teeth.

The delivery carrier maybe transparent or translucent to electromagnetic radiation with wavelengths from about 200 nm to about 1700 nm. In certain embodiments, the delivery carrier allows from about 10%, 20%, or 30% to about 40%, 50%, 60%, 70%, 80%, 90%, or 100% of electromagnetic radiation from about 400 nm to about 500 nm to pass through.

Where the delivery carrier is a strip of material, the second layer composition may be coated on the strip, or be applied by the user to the strip, or be applied by the user to the teeth and then the strip may be placed over the coated teeth. The amount of composition applied to the strip or teeth may depend upon the size and capacity of the strip, concentration of the active and the desired benefit; for example from about 0.0001, 0.001 or 0.01 grams to about 0.01, 0.1, 1, or 5 grams may be used or any other numerical range, which is narrower and which falls within such broader numerical range, as if such narrower numerical ranges were all expressly written herein, of composition, in particular from about 0.001 g to about 0.5 g or from about 0.1 g to about 0.4 g of multi-phase oral composition may be used. In addition, from about 0.0001, 0.001 or 0.01 grams to about 0.01, 0.1, 0.5, or 1 grams composition per square centimeter of material (g/cm$^2$) may be used or any other numerical range, which is narrower and which falls within such broader numerical range, as if such narrower numerical ranges were all expressly written herein; in certain embodiments less than about 0.2 g/cm$^2$, from about 0.0001 g/cm$^2$ to about 0.1 g/cm$^2$, or from about 0.01 g/cm$^2$ to about 0.04 g/cm$^2$. In addition, or alternatively, from about 1 microgram to about 5000 micrograms bleaching agent per square centimeter of material (microgram/cm$^2$), preferably from about 10 micrograms/cm$^2$ to about 500 micrograms/cm$^2$, and more preferably from about 50 micrograms/cm$^2$ to about 100 micrograms/cm$^2$ bleaching agent per square centimeter of material may be used.

Figure 1:
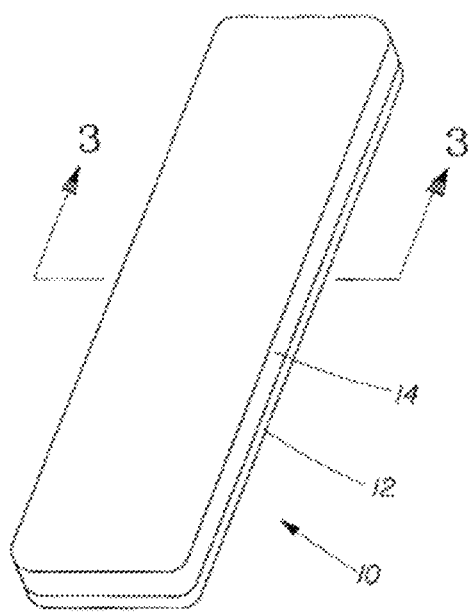
FIG. 1 is a perspective view of a delivery system 10 comprising a strip of material 12 having rounded corners upon which in a second layer 14 the present compositions are coated.
Figure 2:
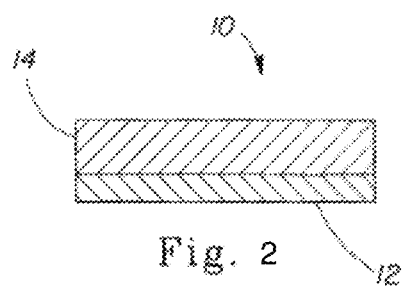
FIG. 2 is a cross-sectional view, taken along section line 3-3 of FIG. 1, showing an example of the strip.

Referring now to the drawings, and more particularly to FIG. 1, there is shown an embodiment of a suitable delivery system 10, representing a delivery system for delivering bleach actives provided by a multi-phase oral composition as disclosed herein to the teeth and the oral cavity. Delivery system 10 comprises a material in strip form 12 of material which is substantially flat, and may have rounded corners. Onto said strip 12 a second layer 14 comprising the present multi-phase oral composition is releasably applied. The second layer 14 may be homogenous and may be uniformly and ly coated onto strip 12, as shown in the cross-sectional view of FIG. 2. In addition, the second layer 14 comprising the present compositions may be a coating only along a longitudinal axis of a portion of strip of material 12 or may be applied as stripes, spots, and/or other patterns. However, in certain embodiments the second layer 14 may be a laminate or separated layers of components, an amorphous mixture of components, separate stripes or spots or other patterns of different components, or a combination of these structures, including a coating of the second layer 14 along a longitudinal axis of a portion of the strip of material 12.

In certain embodiments, the second layer 14 may contain or is itself an active, such as a composition, compound, or mixture capable of influencing or effecting a desired change in appearance or structure of the surface it contacts. As discussed previously, example actives include: hydrogen peroxide, carbamide peroxide, sodium fluoride, sodium monofluorophosphate, pyrophosphate, chlorhexidine, polyphosphate, triclosan, and enzymes. Examples of appearance and structural changes include, but are not necessarily limited to: whitening, stain bleaching, stain removal, remineralization to form fluorapatite, plaque removal, and tartar removal.

In addition, the second layer 14 composition may comprise adhesive means in order to stably attach the delivery system 10 to the tooth surface. In certain embodiments, the composition as disclosed herein may provide the intended stickiness and adhesiveness by its own, for example by choosing a hydrophobic phase which already provides adhesive properties by adding adhesive material to the compositions of the present invention, or both. In certain embodiments, if added, an adhesive may provide additional properties, such as thickening/rheology modifying properties.

Figure 3:
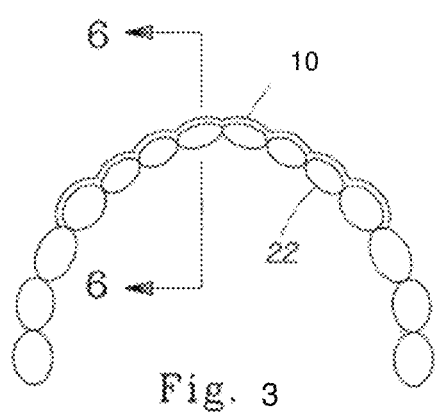
FIG. 3 is a cross-sectional plan view, showing the delivery system 10 attached to the teeth 22 by means of the second layer 14 composition located between the teeth 22 and the strip of material 12.
Figure 4:
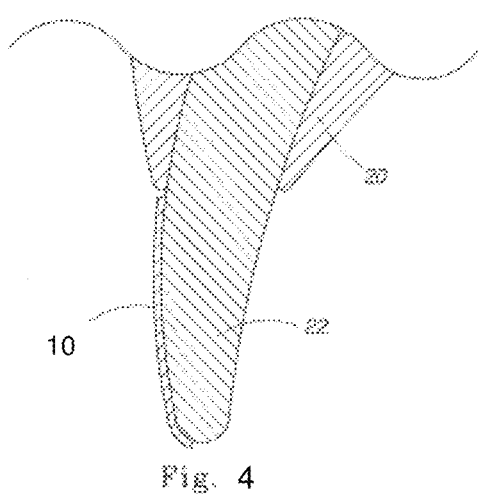
FIG. 4 is a cross-sectional elevation view of a tooth, taken along section line 6-6 of FIG. 3, showing the delivery system 10 adhesively attached to the teeth 22.

FIGS. 3 and 4 show a delivery system 10 of the present invention applied to the tooth surface of a plurality of adjacent teeth. Embedded in adjacent soft tissue 20 is a plurality of adjacent teeth 22. Adjacent soft tissue 20 herein defined as soft tissue surfaces surrounding the tooth structure including: papilla, marginal gingival, gingival sulculus, inter dental gingival, and gingival gum structure on lingual and buccal surfaces up to and including muco-gingival junction on the pallet.

In both FIGS. 3 and 4, delivery system 10 represents a strip 12 and second layer 14 comprising the present composition, wherein the second layer 14 is located on the side of strip of material 12 facing teeth 22. Composition of second layer 14 may be pre-applied to strip of material 12, or may be applied to strip of material 12 by the user prior to application to the teeth. Alternatively, the composition of second layer 14 may be applied directly to teeth 22 by the user and then covered by a strip 12. In any case, strip of material 12 may have a thickness and flexural stiffness such that it can conform to the contoured surfaces of teeth 22 and to adjacent soft tissue 20. Thus, the strip of material 12 may have sufficient flexibility to form to the contours of the oral surface, the surface being a plurality of adjacent teeth 22. The strip 12 may also readily conformable to tooth surfaces and to the interstitial tooth spaces without permanent deformation when the delivery system 10 is applied. The delivery system 10 can be applied without significant pressure.

The first layer 12 of the delivery system 10 may be comprised of a strip of material. Such first layer materials are described in more detail in U.S. Pat. Nos. 6,136,297; 6,096,328; 5,894,017; 5,891,453; and 5,879,691; and in U.S. Pat. Nos. 5,989,569 and 6,045,811; and in patent application US 2014/0178443 A1. The strip 12 serves as a protective barrier for the bleaching agent in the second layer 14. It prevents leaching or erosion of the second layer 14 by for example, the wearer's tongue, lips, and saliva. This allows the active agent in the second layer 14 to act upon the tooth surfaces 22 of the oral cavity for the intended period of time, for example from several minutes to several hours.

The following description of strip of material may apply to the delivery systems 10 with the strip layer 12 as shown in FIGS. 1 to 4 or any form of strips. The strip of material may comprise polymers, natural and synthetic woven materials, non-woven material, foil, paper, rubber and combinations thereof. The strip of material may be a single layer of material or a laminate of more than one layer. Regardless of the number of layers, the strip of material may be substantially water insoluble. The strip material may also be water impermeable. Suitable strip material may be any type of polymer or combination of polymers that meet the required flexural rigidity and are compatible with oral care substances. Suitable polymers include, but are not limited to, polyethylene, ethylvinylacetate, polyesters, ethylvinyl alcohol and combinations thereof. Examples of polyesters include Mylar® and fluoroplastics such as Teflon®, both manufactured by Dupont. In certain embodiments, the material used as strip of material is polyethylene. The strip of material may be less than about 1 mm (millimeter) thick, less than about 0.05 mm thick, or from about 0.001 to about 0.03 mm thick. A polyethylene strip of material may be less than about 0.1 mm thick or from about 0.005 to about 0.02 mm thick.

In certain embodiments, the present invention may comprise a dissolvable film, which can be adhered to the oral cavity thereby releasing an active, the dissolvable film comprising water-soluble polymers, one or more polyalcohols, and one or more actives. In addition to one or more actives, a dissolvable film may contain a combination of certain plasticizers or surfactants, colorants, sweetening agents, flavors, flavor enhancers, or other excipients commonly used to modify the taste of formulations intended for application to the oral cavity. The resulting dissolvable film is characterized by an instant wettability which causes the dissolvable film to soften soon after application to the mucosal tissue, thus preventing the user from experiencing any prolonged adverse feeling in the mouth, and a tensile strength suitable for normal coating, cutting, slitting, and packaging operations.

The dissolvable film may comprise a water-soluble polymer or a combination of water-soluble polymers, one or more plasticizers or surfactants, one or more polyalcohols, and an active.

The polymers used for the dissolvable film include polymers which are hydrophilic and/or water-dispersible. Examples of polymers that can be used include polymers that are water-soluble cellulose-derivatives, such as hydroxypropylmethyl cellulose, hydroxyethyl cellulose, or hydroxypropyl cellulose, either alone, or mixtures thereof. Other optional polymers, without limiting the invention, include polyvinyl pyrrolidone, carboxymethyl cellulose, polyvinyl alcohol, sodium alginate, polyethylene glycol, natural gums like xanthane gum, tragacantha, guar gum, acacia gum, arabic gum, water-dispersible polyacrylates like polyacrylic acid, methylmethacrylate copolymer, carboxyvinyl copolymers. The concentration of the water-soluble polymer in the final film can very between 20 and 75% (w/w), or between 50 and 75% (w/w).

The surfactants that may be used for the dissolvable film may be one or more nonionic surfactants. When a combination of surfactants is used, the first component may be a polyoxyethylene sorbitan fatty acid ester or a ALPHA-hydro-OMEGA-hydroxypoly (oxyethylene)poly(oxypropylene)poly(oxyethylene) block copolymer, while the second component may be a polyoxyethylene alkyl ether or a polyoxyethylene castor oil derivative. In certain embodiments, the HLB value of the polyoxyethylene sorbitan fatty acid ester should be between 10 and 20, whereby a range of 13 to 17 may also be used. The ALPHA-hydro-OMEGA-hydroxypoly(oxyethylene)poly(oxypropylene) poly(oxyethylene) block copolymer may contain at least about 35 oxypropylene-units, and in certain embodiments not less than about 50 oxypropylene-units.

The polyoxyethylene alkyl ether may an HLB value between 10 and 20, and in certain embodiments an HLB value of not less than 15 may be used. The polyoxyethylene castor oil derivative may have an HLB value of 14-16.

In order to achieve the desired instant wettability, the ratio between the first and second component of the binary surfactant mixture may be kept within 1:10 and 1:1, or between 1:5 and 1:3.

The total concentration of surfactants in the dissolvable film depends on the properties of the other ingredients, but usually may be between 0.1 and 5% (w/w).

The polyalcohol can be used to achieve a desired level of softness of the dissolvable film. Examples of polyalcohols include glycerol, polyethylene glycol, propylene glycol, glycerol monoesters with fatty acids or other pharmaceutically used polyalcohols. The concentration of the polyalcohol in the dry film usually ranges between 0.1 and 5% (w/w).

The shape of the strip of material may be any shape or size that covers the desired oral surface. For example, in certain embodiments the strip of material may have rounded corners to avoid irritation of the soft tissue of the oral cavity. "Rounded corners," as used herein means not having any sharp angles or points, for example one or more angles of 135° or less. The length of the strip of material may be from about 2 cm (centimeter) to about 12 cm, or from about 4 cm to about 9 cm. The width of the strip of material may also depend on the oral surface area to be covered. The width of the strip of material may be from about 0.5 cm to about 4 cm or from about 1 cm to about 2 cm. The strip or material may be worn as a patch on one or several teeth to treat a localized condition.

The strip of material may contain shallow pockets. When the multi-phase oral composition is coated on a strip of material, bleach agents and/or oral care actives, fill shallow pockets to provide reservoirs of additional bleach agents and/or oral care actives. Additionally the shallow pockets help to provide texture to the delivery system. The strip of material may have an array of shallow pockets. Generally the shallow pockets are approximately 0.4 mm across and about 0.1 mm deep. When shallow pockets are included in the strip of material and multi-phase oral compositions herein are applied to it in various thicknesses, the overall thickness of the delivery system is less than about 1 mm, in particular the overall thickness is less than about 0.5 mm.

Flexural stiffness is a material property that is a function of a combination of strip of material thickness, width and material modulus of elasticity. The test described below is a method for measuring the rigidity of films, such as polyolefin film and sheeting. It determines the resistance to flexure of a sample by using a strain gauge affixed to the end of a horizontal beam. The opposite end of the beam presses across a strip of the sample to force a portion of the strip into a vertical groove in a horizontal platform upon which the sample rests. A microammeter wired to the strain gauge is calibrated in terms of deflection force. The rigidity of the sample is read directly from the microammeter and expressed as grams per centimeter of the sample strip width. In certain embodiments, a strip of material which is suitable to be used as delivery carrier of the compositions as disclosed herein may show a flexural stiffness of less than about 5 grams/cm as measured on a Handle-O-Meter, model #211-300, available from Thawing-Albert Instrument Company of Philadelphia, PA as per test method ASTM D2923-95. The strip may have a flexural stiffness less than about 3 grams/cm, less than about 2 grams/cm or a flexural stiffness from about 0.1 to about 1 grams/cm. Generally, the flexural stiffness of the strip of material may be substantially constant and does not change during normal use. For example, the strip of material does not need to be hydrated for the strip to achieve the low flexural stiffness in the above-specified ranges. This relatively low stiffness enables the strip of material to cover the contours of the oral surface with very little force being exerted. That is, conformity to the contours of the oral surface of the wearer's mouth is maintained because there is little residual force within the strip of material to cause it to return to its shape just prior to its application to the oral surface, i.e. substantially flat. For example, in certain embodiments a strip of material's flexibility enables it to contact soft tissue over an extended period of time without irritation; such that a strip of material does not require pressure for retention against the oral surface.

The delivery systems as used herein may comprise an adhesion means, such that they are capable of adhesion to oral surfaces, especially the teeth. This adhesion means may be provided by the present compositions herein or the adhesion means may be provided independently of the compositions herein (for example the adhesion means is a separate phase from the compositions herein where the compositions may also have an adhesive means). In certain embodiments, the strip of material may be held in place on the oral surface by adhesive attachment provided by the present composition. The viscosity and general tackiness of the multi-phase oral composition to dry surfaces may cause the strip to be adhesively attached to the oral surface without substantial slippage from the frictional forces created by the lips, teeth, tongue, and other oral surfaces rubbing against the strip of material while talking drinking, etc. However, this adhesion to the oral surface may be low enough to allow the strip of material to be easily removed by the wearer by simply peeling off the strip of material using one's finger. The delivery system may be easily removable from the oral surfaces without the use of an instrument, a chemical solvent or agent or excess friction.

In addition, in certain embodiments the strip of material may be held in place on the oral surface by adhesive means and attachment provided by the delivery carrier itself. For example, the strip of material can extend, attach, and adhere to the oral soft tissue. In addition, in certain embodiments an adhesive can be applied to that portion of the strip of material that will attach the delivery systems to the oral soft tissue. The delivery carrier may also be attached to the oral cavity by physical interference or mechanical inter-locking between the delivery carrier and the oral surfaces including the teeth. In addition, the strip of material may be held in place by an adhesion means that is independent of the composition of the present inventions herein, as disclosed in WO 03/015656.

Suitable adhesion means are known to the skilled person. When the adhesive means, if present, is provided by an adhesive, the adhesive may be any adhesive which may be used to adhere materials to the tooth surface or to a surface of the oral cavity surfaces. Suitable adhesives include, but are not limited to, skin, gum and muco adhesives, and should be able to withstand the moisture, chemicals and enzymes of the oral environment for long enough for the oral care actives and/or bleach to take effect, but may be soluble and/or biodegradable thereafter. Suitable adhesives may for example comprise water soluble polymers, hydrophobic and/or non-water soluble polymers, pressure and moisture sensitive adhesives, e.g. dry adhesives which become tacky upon contact with the mouth environment, e.g. under the influence of moisture, chemicals or enzymes etc. in the mouth. Suitable adhesives include natural gums, synthetic resins, natural or synthetic rubbers, those gums and polymers listed above under "Thickening Agents", and various other tacky substances of the kind used in known adhesive tapes, those known from U.S. Pat. No. 2,835,628.

The delivery carrier, such as a strip, as shown for example in FIGS. 1 to 4, may be formed by several of the film making processes known in the art. For example, a strip of polyethylene is made by a blown process or a cast process. Other processes including extrusion or processes that do not affect the flexural rigidity of the strip of material are also feasible. In addition, the present compositions forming a second layer onto the strip may be incorporated onto the strip during the processing of the strip and/or the present composition may be a laminate layer on the strip. The second layer attached to the strip of such a delivery system as disclosed above comprises a safe and effective amount of the present composition described herein.

In addition, the delivery system may comprise an optional release liner. Such a release liner may be formed from any material which exhibits less affinity for the second layer composition than the second layer composition exhibits for itself and for the first layer strip of material. The release liner may comprise a rigid sheet of material such as polyethylene, paper, polyester, or other material, which is then coated with a nonstick type material. The release liner may be cut to substantially the same size and shape as the strip of material or the release liner may be cut larger than the strip of material to provide a readily accessible means for separating the material from the strip. The release liner may be formed from a brittle material that cracks when the strip is flexed or from multiple pieces of material or a scored piece of material. Alternatively, the release liner may be in two overlapping pieces such as a typical adhesive bandage design. A description of materials suitable as release agents is found in Kirk-Othmer, Encyclopedia of Chemical Technology, Fourth Edition, Volume 21, pp. 207-218, incorporated herein by reference.

In certain embodiments, the delivery carrier may be a permanently deformable strip of material having a yield point and thickness such that the strip of material substantially conforms to a shape of a tooth via permanent deformation under a pressure less than about 250,000 Pascals as it has been found that wearers will press a strip onto each tooth using one fingertip having about one square centimeter surface area. They typically apply force at each tooth for one second or less with a typical application pressure ranging from about 100,000 Pascals to about 250,000 Pascals.

In certain embodiments, a strip of material has viscoelastic properties which enable it to creep as well as bend in order to conform across several teeth and around the arch of the wearer's mouth. It is important that the necessary permanent deformation occurs under minimum normal force being applied by the wearer.

The multi-phase oral composition may also be applied to the tooth surface and may be covered with the deformable strip before or after it has been shaped. In addition, or alternatively, the multi-phase oral composition may be applied to the deformable strip as pre-coating and may be applied together with the strip to the tooth surface before or after the deformable strip has been shaped, wherein the strip is applied such that when the delivery system is placed on a surface of the tooth, the multi-phase oral composition contacts the tooth surface providing an active onto the tooth surface. In addition or alternatively, the deformable strip of material may be applied to the teeth with a force sufficient to shape the delivery carrier such that it at least partially conforms to the shape of the teeth, then the shaped strip of material may be removed from the tooth surface, the oral care composition may be applied to the shaped strip of material, and the shaped strip of material may be re-applied to the tooth surface such that it at least partially conforms to a shape of the tooth and contacts the oral care composition against the tooth surface. If the deformable strip is applied together with the multi-phase oral composition to the tooth surface the multi-phase oral composition may also comprise adhesive agents to hold the delivery system in place for a sufficient time to allow the active of the multi-phase oral composition to act upon the surface. The multi-phase oral composition, if used together with a deformable strip, may have an extrusion resistance sufficient to withstand a normal force applied to shape the deformable strip of material so that the substance is not substantially extruded from between the deformable strip of material and the surface during manual shaping of the deformable strip of material. By "substantially extruded from" is meant that at least 50% or more of the multi-phase oral composition is extruded from between the deformable strip of material and the tooth and adjoining soft tissue surfaces.

The deformable strip of material may be made of a permanently deformable material, such as wax, putty, tin or foil, as a single layer or a combination of layers or materials, such as a laminate. In certain embodiments, the deformable strip may be wax, such as #165 sheet wax formulated and manufactured by Freeman Mfg. & Supply Co. of Cleveland, Ohio. This particular wax readily conforms to the shape of a tooth under a pressure of about 133,000 Pascal which is the pressure generated when the wearer applies a normal force of about 3 pounds (1.36 kg) over an area of about one square centimeter. The deformable strip of material may have a nominal film thickness of about 0.8 mm, wherein the deformable strip may be substantially flat and rectangular in shape with rounded corners. The deformable strip of material may have a length sufficient to cover a plurality of adjacent teeth while conforming to the curvature of the wearer's mouth and gaps between the adjacent teeth. If the deformable strip of material includes the multi-phase oral composition coated thereon, the multi-phase oral composition may have an overall thickness less than about 1.5 mm. Deformable strips as disclosed herein may also be used as the material for the strip of material 12 shown in FIGS. 1 to 4. Thus, general features of a strip of material as described above for example with respect to FIGS. 1 to 4 may also apply to the deformable strip of material. In addition, a release liner and/or shallow pockets may also be combined with a deformable strip of material.

Figure 5:
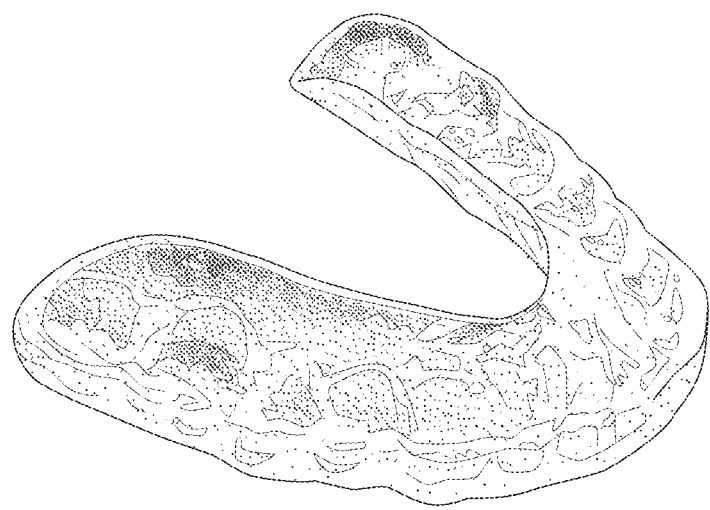
FIG. 5 shows a dental tray 30 suitable to be used with the composition of the present invention.

Alternatively, the present compositions may be used in combination with a delivery carrier including a dental tray and/or foam material. Dental trays are well known in the whitening art and an example dental tray 30 is shown in FIG. 5. The general process for preparing dental trays 30 is known in the art. Dentists have traditionally utilized three types of dental appliances for bleaching teeth.

The first type is a rigid appliance which is fitted precisely to the patient's dental arches. For example, an alginate impression which registers all teeth surfaces plus gingival margin is made and a cast is promptly made of the impression. If reservoirs are desired they are prepared by building a layer of rigid material on the cast on specific teeth surfaces to be treated. A dental tray is then vacuum formed from the modified cast using conventional techniques. Once formed, the tray is preferably trimmed barely shy of the gingival margin on both buccal and lingual surfaces. Enough tray material should be left to assure that all of the tooth will be covered to within about ¼ to about ⅓ mm of the gingival border upon finishing and beveling the tray periphery. One can scallop up and around interdental papilla so that the finished tray does not cover them. All tray edges are preferably smoothed so that the lip and tongue will not feel an edge prominence. The resulting tray, provides a perfect fit of the patient's teeth optionally with reservoirs or spaces located where the rigid material was placed on the cast. Dental trays may comprise of soft transparent vinyl material having a preformed thickness from about 0.1 cm to about 0.15 cm. Soft material is more comfortable for the patient to wear. Harder material (or thicker plastic) may also be used to construct the tray.

A second type of rigid custom dental appliance is an "oversized" rigid custom dental appliance. The fabrication of rigid, custom dental appliances entails fabricating cast models of the patient's dental arch impressions, and heating and vacuum-forming a thermoplastic sheet to correspond to the cast models of a patient's dental arches. Thermoplastic films are sold in rigid or semi rigid sheets, and are available in various sizes and thickness. The dental laboratory fabrication technique for the oversized rigid dental appliance involves augmenting the facial surfaces of the teeth on the cast models with materials such as die spacer or light cured acrylics. Next, thermoplastic sheeting is heated and subsequently vacuum formed around the augmented cast models of the dental arch. The net effect of this method results in an "oversized" rigid custom dental appliance.

A third type of rigid custom dental appliance, used with less frequency, is a rigid bilaminated custom dental appliance fabricated from laminations of materials, ranging from soft porous foams to rigid, non-porous films. The non-porous, rigid thermoplastic shells of these bilaminated dental appliances encase and support an internal layer of soft porous foam.

A fourth type of dental tray replaces rigid custom dental appliances with disposable U-shaped soft foam trays, which may be individually packaged, and which may be saturated with a pre-measured quantity of the composition of the present invention. The soft foam material is generally an open celled plastic material. Such a device is commercially available from Cadco Dental Products in Oxnard, Calif. under the tradename VitalWhite™. These soft foam trays may comprise a backing material (e.g. a closed cell plastic backing material) to minimize the elution of the bleaching agent from the device, into the oral cavity to minimize ingestion by the patient and/or irritation of the oral cavity tissues. Alternatively, the soft foam tray is encased by a nonporous flexible polymer or the open cell foam is attached to the frontal inner wall of the dental appliance and/or the open cell foam is attached to the rear inner wall of the dental appliance. Those of ordinary skill in the art will readily recognize and appreciate, that the present compositions must be thick enough not to simply run out between the open cell structure of the foam and must be thin enough to slowly pass through the open cell foam over time. In other words, the open cell foam material has an internal structural spacing sized relative to the viscosity of the compositions to absorb and allow the composition to pass there through.

An example of a closed cell material is a closed-cell polyolefin foam sold by the Voltek division of Sekisui America Corporation of Lawrence, Mass. under the tradename Volora which is from 1/32" to ⅛" in thickness. A closed cell material may also comprise of a flexible polymeric material. An example of an opened cell material is an open-celled polyethylene foam sold by the Sentinel Foam Products division of Packaging Industries Group, Inc. of Hyannis, Mass. under the tradename Opcell which is from 1/16" to ⅜" in thickness. Other open cell foam useful herein include hydrophilic open foam materials such as hydrogel polymers (e.g Medicell™ foam available from Hydromer, Inc. Branchburg, J.J.). Open cell foam may also be hydrophilic open foam material imbibed with agents to impart high absorption of fluids, such as polyurethane or polyvinylpyrrolidone chemically imbibed with various agents.

Preparation of the Present Multi-Phase Oral Compositions

Principally, preparation of emulsions is well known in the art and any suitable manufacturing process can be used to make the multi-phase oral composition, which may be in the form of an emulsion; see for example, *Remmingtion: the Science and Practice of Pharmacy,* 19$^{th}$ ed., Vol. II, Chapters 20, 80, 86, etc. Generally, the components are separated into those that are oil-soluble and those that are water-soluble. These are dissolved in their respective solvents by heating if necessary. The two phases are then mixed and the product is stirred and cooled. After combining the phases, the present multi-phase oral compositions, may be agitated or sheared by various methods, including shaking, intermittent shaking, high shear mixing, or by using high speed mixers, blenders, colloid mills, homogenizers, or ultrasonic techniques. Various test methods are available to confirm the type of multi-phase oral compositions were prepared. These test methods include the dilution test, conductivity test, microscopy, and the dye-solubility test methods. Further description of test methods are disclosed in *Remington: The Science and Practice of Pharmacy,* 19$^{th}$ ed., volume 1, 1995, pp. 282-283.

In certain embodiments, multi-phase oral compositions, as disclosed herein may be made as follows: dissolve the bleach active in the aqueous phase; then combine the aqueous phase and the hydrophobic phase in a mixing vessel and mix well with any means known within the art, for example, a Speed-mixer (from Flacktek Inc., Landrum, SC) may be used to make multi-phase oral compositions of the present invention. The mixing procedure of the Speed-Mixer™ series is based on the double rotation of the mixing cup using a dual asymmetric centrifugal mixing. This combination of centrifugal forces acting on different levels enables very rapid mixing of the entire cup. Optionally the composition may be heated, if necessary to facilitate solving of the bleaching active or the mixing. Continue mixing the composition until uniform. When the active is included in solid particulate form, the addition of an optional viscosity modifier, such as silica, may be appropriate to keep the particulate dispersed and suspended within the composition. Flavorants or sweeteners may also be added to one of the phases of the composition, as desired. Thereafter the composition may be added to the delivery carrier, as desired.

Multi-Phase Oral Composition Formulation Examples

The following non-limiting Formulation examples further describe embodiments within the scope of the present invention. Many variations of these examples are possible without departing from the scope of the invention.

Formulation Examples I

Formulation Examples I can be made using any suitable procedure disclosed above and formulated with a 35% aqueous solution of hydrogen peroxide. These examples illustrate compositions that can be made with 1) the concentration of $H_2O_2$ in the overall composition ranging from 0.001% to 0.0875%, and 2) the ratio of the concentration in weight percent of $H_2O_2$ present in the aqueous phase to the concentration in weight percent of $H_2O_2$ present in the overall composition ranging from 400 to 34483.

| Formulation Examples I | A (Wt %) | B (Wt %) | C (Wt %) | D (Wt %) | E (Wt %) | F (Wt %) | G (Wt %) |
|---|---|---|---|---|---|---|---|
| 35% aqueous solution $H_2O_2$[15] | 0.25 | 0.20 | 0.15 | 0.10 | 0.05 | 0.0286 | 0.0029 |
| Petrolatum[16] | 99.75 | 99.80 | 99.85 | 99.90 | 99.95 | 99.9714 | 99.9971 |
| total | 100.00 | 100.00 | 100.00 | 100.00 | 100.00 | 100.00 | 100.00 |
| % $H_2O_2$ in total oral compos. | 0.0875 | 0.07 | 0.0525 | 0.035 | 0.0175 | 0.01 | 0.001015 |
| RATIO* | 400 | 500 | 667 | 1000 | 2000 | 3500 | 34483 |

*RATIO of the concentration in weight percent of $H_2O_2$ present in the aqueous phase to the concentration in weight percent of $H_2O_2$ present in the overall composition
[15]ultra Cosmetic Grade from Solvay, Houston, Texas
[16]G-2191 Grade from Sonneborn, LLC., Parsippany, NJ Formulation Examples II Formulation Examples II can be made using any suitable procedure disclosed above and formulated with a 50% aqueous solution of hydrogen peroxide. These examples illustrate compositions that can be made with 1) the concentration of $H_2O_2$ in the overall composition ranging from 0.0015% to 0.1%, and 2) the ratio of the concentration in weight percent of $H_2O_2$ present in the aqueous phase to the concentration in weight percent of $H_2O_2$ present in the overall composition ranging from 500 to 34483.

| Formulation Examples II | A (Wt %) | B (Wt %) | C (Wt %) | D (Wt %) | E (Wt %) | F (Wt %) |
|---|---|---|---|---|---|---|
| 50% aqueous sol. $H_2O_2$ | 0.20 | 0.15 | 0.10 | 0.05 | 0.0286 | 0.0029 |
| Petrolatum[17] | 99.8 | 99.85 | 99.90 | 99.95 | 99.9714 | 99.9971 |
| total | 100.0 | 100.0 | 100.0 | 100.0 | 100.0 | 100.0 |
| % $H_2O_2$ in total compos. | 0.10 | 0.075 | 0.05 | 0.025 | 0.0143 | 0.00145 |
| RATIO* | 500 | 667 | 1000 | 2000 | 3500 | 34483 |

*RATIO of the concentration in weight percent of $H_2O_2$ present in the aqueous phase to the concentration in weight percent of $H_2O_2$ present in the overall composition
[17]G-2191 Grade from Sonneborn, LLC., Parsippany, NJ Formulation Examples III Formulation Examples III can be made using any suitable procedure disclosed above and formulated with a 17.5% aqueous solution of hydrogen peroxide. These examples illustrate compositions that can be made with 1) the concentration of $H_2O_2$ in the overall composition ranging from 0.0088% to 0.0875%, and 2) the ratio of the concentration in weight percent of $H_2O_2$ present in the aqueous phase to the concentration in weight percent of $H_2O_2$ present in the overall composition ranging from 200 to 2000.

| Formulation Examples II | A (Wt %) | B (Wt %) | C (Wt %) | D (Wt %) | E (Wt %) | F (Wt %) |
|---|---|---|---|---|---|---|
| 17.5% aqueous sol. $H_2O_2$[18] | 0.5 | 0.4 | 0.3 | 0.2 | 0.1 | 0.05 |
| Petrolatum[19] | 99.5 | 99.6 | 99.7 | 99.8 | 99.9 | 99.95 |
| total | 100.0 | 100.0 | 100.0 | 100.0 | 100.0 | 100.0 |
| % $H_2O_2$ in total compos. | 0.0875 | 0.07 | 0.0525 | 0.035 | 0.0175 | 0.0088 |
| RATIO* | 200 | 250 | 333 | 500 | 1000 | 2000 |

*RATIO of the concentration in weight percent of $H_2O_2$ present in the aqueous phase to the concentration in weight percent of $H_2O_2$ present in the overall composition
[18]ultra Cosmetic Grade from Solvay (Houston, Texas) diluted with water
[19]G-2191 Grade from Sonneborn, LLC., Parsippany, NJ Formulation Examples IV Formulation Examples IV can be made using any suitable procedure disclosed above and formulated with a 8.75% aqueous solution of hydrogen peroxide. These examples illustrate compositions that can be made with 1) the concentration of $H_2O_2$ in the overall composition ranging from 0.0044% to 0.099995%; and 2) the ratio of the concentration in weight percent of $H_2O_2$ present in the aqueous phase to the concentration in weight percent of $H_2O_2$ present in the overall composition ranging from 87.5 to 2000.

| Formulation Examples IV | A (Wt %) | B (Wt %) | C (Wt %) | D (Wt %) | E (Wt %) | F (Wt %) | G (Wt %) | H (Wt %) |
|---|---|---|---|---|---|---|---|---|
| 8.75% aqueous sol. $H_2O_2$[20] | 1.1428 | 1.0 | 0.8 | 0.6 | 0.4 | 0.2 | 0.1 | 0.05 |
| Petrolatum[21] | 98.8572 | 99.0 | 99.2 | 99.4 | 99.6 | 99.8 | 99.9 | 99.95 |
| total | 100.0 | 100.0 | 100.0 | 100.0 | 100.0 | 100.0 | 100.0 | 100.0 |
| % $H_2O_2$ in total compos. | 0.099995 | 0.0875 | 0.07 | 0.0525 | 0.035 | 0.0175 | 0.0088 | 0.0044 |
| RATIO* | 87.50 | 100 | 125 | 167 | 250 | 500 | 1000 | 2000 |

*RATIO of the concentration in weight percent of $H_2O_2$ present in the aqueous phase to the concentration in weight percent of $H_2O_2$ present in the overall composition
[20]ultra Cosmetic Grade from Solvay (Houston, Texas) diluted with water
[21]G-2191 Grade from Sonneborn, LLC., Parsippany, NJ Formulation Examples V Formulation Examples V can be made using any suitable procedure disclosed above and formulated with a 35% aqueous solution of hydrogen peroxide. These examples illustrate compositions that can be made with 1) various hydrophobic phases; and 2) various fillers.

| Formulation Examples V | A (Wt %) | B (Wt %) | C (Wt %) | D (Wt %) | E (Wt %) | F (Wt %) |
|---|---|---|---|---|---|---|
| 35% aqueous sol. $H_2O_2$[22] | 0.2857 | 0.2857 | 0.2857 | 0.2857 | 0.2857 | 0.2857 |
| Petrolatum[23] | 49.7143 | 79.7143 | 89.7143 | 99.6143 | | |
| Mineral oil[24] | | | | 69.7143 | 39.7143 | |
| Polyethylene[25] | | | | 20.00 | | |
| Microcrystalline Wax[26] | | | | | | 50.00 |
| Polyethylene particles[27] | 50.0000 | | | | | |
| Silica particles | | 20.0000 | | | | |
| Cross-linked siloxane particles[28] | | | 10.0000 | 0.1000 | 10.0000 | 10.0000 |
| total | 100.0000 | 100.0000 | 100.0000 | 100.0000 | 100.0000 | 100.0000 |
| % Aqueous phase | 0.2857 | 0.2857 | 0.2857 | 0.2857 | 0.2857 | 0.2857 |
| % Hydrophobic phase | 99.7143 | 99.7143 | 99.7143 | 99.7143 | 99.7143 | 99.7143 |
| % Filler | 50.0000 | 20.0000 | 10.0000 | 0.1000 | 10.0000 | 10.0000 |

| Formulation Examples V | A (Wt %) | B (Wt %) | C (Wt %) | D (Wt %) | E (Wt %) | F (Wt %) |
|---|---|---|---|---|---|---|
| % $H_2O_2$ in total compos. | 0.099995 | 0.099995 | 0.099995 | 0.099995 | 0.099995 | 0.099995 |
| RATIO* | 350.02 | 350.02 | 350.02 | 350.02 | 350.02 | 350.02 |

*RATIO of the concentration in weight percent of $H_2O_2$ present in the aqueous phase to the concentration in weight percent of $H_2O_2$ present in the overall composition
[22]ultra Cosmetic Grade from Solvay, Houston, Texas
[23]G-2191 Grade from Sonnebom LLC., Parsippany, NJ
[24]Kaydol grade from Sonnebom LLC., Parsippany, NJ
[25]400 Grade from Baker-Hughes, Houston, TX dissolved into the mineral oil at 95 C.
[26]W835 Grade from Sonnebom LLC., Parsippany, NJ dissolved into the mineral oil at 95° C.
[27]400 Grade from Baker-Hughes, Houston, TX, added into the multi-phase oral composition below its melt point such that it is present as particulate filler
[28]Tospearl from Momentive Inc. added into the multi-phase oral composition such that it is present as particulate filler

FORMULATION COMPARATIVE EXAMPLES

Formulation Comparative Examples I

Formulation Comparative Examples I can be made using any suitable procedure disclosed above or in EP 1 696 866 B1. These examples illustrate compositions that 1) have $H_2O_2$ levels much higher than 0.1% of the overall composition, and 2) have ratios of the concentration in weight percent of $H_2O_2$ present in the aqueous phase to the concentration in weight percent of $H_2O_2$ present in the overall composition lower than ranges preferred according to the present invention.

| Formulation Comparative Examples I | | | | |
|---|---|---|---|---|
| | A (Wt %) | B (Wt %) | C (Wt %) | D (Wt %) |
| 35% aqueous sol. $H_2O_2$ [29] | 17.00 | 1.43 | 17.00 | 17.00 |
| Mineral oil[30] | 77.90 | 93.33 | 73.90 | |
| Aerosol OT[31] | 1.00 | 1.00 | 1.00 | |
| Polysorbate 80[32] | | | | 1.00 |
| Silica | | | 4.00 | |
| Water | 4.10 | 4.24 | 4.10 | 4.10 |
| EDTA | | | | 0.03 |
| Olive Oil | | | | 77.88 |
| total | 100.0000 | 100.0000 | 100.0000 | 100.0000 |
| % $H_2O_2$ in total compos. | 5.95 | 0.50 | 5.95 | 5.05 |
| RATIO* | 4.74 | 17.64 | 4.74 | 4.52 |

*RATIO of the concentration in weight percent of $H_2O_2$ present in the aqueous phase to the concentration in weight percent of $H_2O_2$ present in the overall composition
[29]ultra Cosmetic Grade from Solvay, Houston, Texas
[30]Kaydol grade from Sonnebom LLC., Parsippany, NJ
[31]sodium dioctyl sulfosuccinate, from Cytec Industries Inc. NJ.
[32]ethoxylated sorbitan monooleate, from Spectrum Chemical MfG group
[33] from Calumet Lubricants
[34]Cetearyl Alcohol and Ceteareth-20, from Lipo Chemical.

Formulation Comparative Examples II

Formulation Comparative Examples II can be made using any suitable procedure disclosed above or in EP 1 696 866 B1. These examples illustrate compositions that 1) have $H_2O_2$ levels much higher than 0.1% of the overall composition, and 2) have ratios of the concentration in weight percent of $H_2O_2$ present in the aqueous phase to the concentration in weight percent of $H_2O_2$ present in the overall composition lower than ranges preferred according to the present invention.

| Formulation Comparative Examples II | | | | |
|---|---|---|---|---|
| | A (Wt %) | B (Wt %) | C (Wt %) | D (Wt %) |
| 35% aqueous sol. $H_2O_2$ [35] | 17.00 | 6.00 | 17.00 | 17.00 |
| Mineral oil[36] | 74.00 | 83.00 | 63.00 | |
| Aerosol OT[37] | 1.00 | 1.00 | 1.00 | |
| Polysorbate 80[38] | | | | 1.00 |
| Silica | | | 4.00 | |
| Water | 8.00 | 10.00 | 15.00 | 10.00 |
| EDTA | | | | 0.03 |
| Olive Oil | | | | 71.98 |
| total | 100.0000 | 100.0000 | 100.0000 | 100.0000 |
| % $H_2O_2$ in total compos. | 5.95 | 2.10 | 5.95 | 5.95 |
| RATIO* | 4.00 | 6.25 | 3.13 | 3.57 |

*RATIO of the concentration in weight percent of $H_2O_2$ present in the aqueous phase to the concentration in weight percent of $H_2O_2$ present in the overall composition
[35] ultra Cosmetic Grade from Solvay, Houston, Texas
[36]Kaydol grade from Sonnebom LLC., Parsippany, NJ
[37]sodium dioctyl sulfosuccinate, from Cytec Industries Inc. NJ.
[38]ethoxylated sorbitan monooleate, from Spectrum Chemical MfG group The ratio of the concentration in weight percent of bleaching agent present in the aqueous phase to the concentration in weight percent of bleaching agent present in the overall composition of the Formulation comparative examples I and II range from a minimum of 3.13 to a maximum of 17.64, while the ratio ranges from about 50 to about 34483 in examples I, II, and III, and Formulation examples I, II, III, IV, and V above. Specifically, the ratio of the concentration in weight percent of bleaching agent present in the aqueous phase to the concentration in weight percent of bleaching agent present in the overall composition of the Formulation comparative examples I and II has a maximum value of 17.64 while the ratio for examples I, II, and III, and Formulation examples I, II, III, IV, and V above has a minimum of about 50.

Methods of Using the Compositions and/or Delivery Systems

The present invention can be applied to the teeth of a consumer in the dental office by a dental professional, or can be used at home by the consumer. Generally, the recommended treatment period is, a sufficient period of time to achieve whitening.

In practicing the present invention, the user applies the composition herein that contains the bleaching agent to obtain the desired effect, such as, whitening, to one or more teeth. The composition can be applied with a paint-on device, a syringe or unit dose syringe, squeezable tube, a brush, a pen or brush tip applicator, a doe's foot applicator, swab, lip gloss applicator, strip that is removed after application, tray that is removed after application, or the like, or even with the fingers. The composition can also be combined with a delivery carrier, such as a strip of material, a dental tray, or a sponge material, and thereafter applied to the teeth. In certain embodiments, the compositions or delivery systems herein are almost unnoticeable when applied to the teeth. After a desired period of time has elapsed, any residual composition may be easily removed by wiping, brushing or rinsing the oral surface.

In general, it is not necessary to prepare the teeth before applying the present composition. For example, the user may choose to brush the teeth or rinse the mouth before applying the compositions of the present invention, but the surfaces of the oral cavity are neither required to be clean, nor to be dried nor to be excessively wet with saliva or water before the application. However, it is believed that adhesion to the tooth enamel surfaces will be improved if the teeth are dry prior to application.

Dental tray appliances may be used as follows. The patient or dental professional dispenses the present composition into a soft or rigid dental appliance and then the participant places the appliance over the participant's dental arch (or fits the device around his or her teeth to keep the tray in position). Generally, the recommended treatment period is a sufficient period of time to achieve whitening as disclosed above. At the end of the treatment period, the dental appliance is removed, cleaned with water to remove any remaining composition, and then stored until the next application.

The above-described compositions and delivery systems may be combined in a kit which comprises: 1. present composition and 2. instructions for use; or which comprises: 1. present composition, 2. instructions for use, and optionally 3. a delivery carrier. In addition, if the tooth shall be radiated by electromagnetic radiation, the kit may further comprise an electromagnetic radiation source of the appropriate wavelength and instruction for use, so that the kit can be used by consumers in a convenient manner.

Optional Electromagnetic Radiation Treatment

Figure 7:
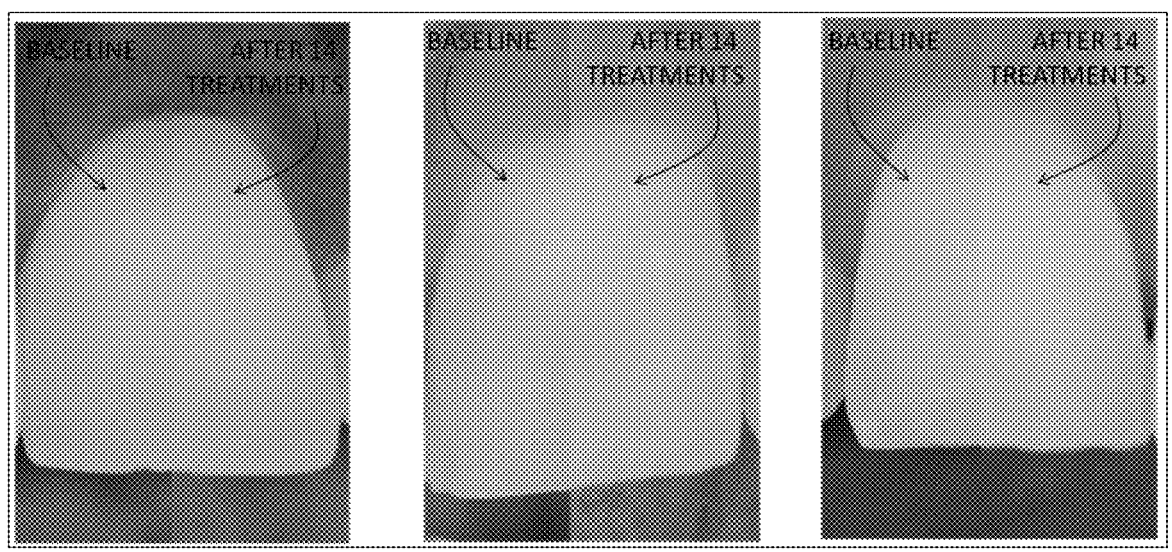
FIG. 7 shows the bleaching efficacy on a natural tooth surface after 14 treatments using a composition of the present invention (Example-IA delivered on a strip and used with Electromagnetic radiation having a peak intensity wavelength of 455 nm).

The multi-phase oral composition as disclosed herein may be used to whiten teeth and/or removing stain from tooth surfaces. In addition, the bleaching efficacy may be further increased by directing electromagnetic radiation of a suitable wavelength toward at least one tooth. A device suitable to provide such electromagnetic radiation is shown in FIG. 7. A suitable wavelength may be every wavelength, which corresponds to a maximum absorption band of the tooth and/or the tooth stain to be bleached. For example, the multi-phase oral composition may be radiated with an electromagnetic radiation with one or more wavelengths in the range of from about 200 nm to about 1200 nm. The electromagnetic radiation may be directed toward at least one tooth. In addition, more than one tooth may be irradiated. In particular, the electromagnetic radiation may have a peak intensity at a wavelength in the range of from about 400, 405, 410, 415, 420, 425, 430, 435, 440, or 445, 446 nm to about 450, 455, 460, 465, 470, 475, 480, 481, 485, 490, 495, or 500 nm or any other numerical range, which is narrower and which falls within such broader numerical range, as if such narrower numerical ranges were all expressly written herein. In certain embodiments, the electromagnetic radiation has a peak intensity at a wavelength in the range of from about 425 nm to about 475 nm, from about 445 nm to about 465 nm, or wherein the peak intensity wavelength of the electromagnetic radiation is similar to the wavelength at which the stain absorbs the most electromagnetic radiation. Electromagnetic radiation may be directed toward at least one tooth for partial or whole wearing time of the composition; or after the composition has been removed from the tooth. Electromagnetic radiation may be applied at least for a sufficient period of time for whitening, e.g. for at least about 1 minute, for at least about 5 minutes, or for at least about 10 min. The electromagnetic radiation may be applied using the procedure disclosed in US 2013/0295525. Preferably the multi-phase oral composition as disclosed herein is applied to at least one tooth and maintained on the at least one tooth for a first period of time; after the first period of time electromagnetic radiation is directed toward the at least one tooth for a second period of time, wherein the first period of time has a duration greater than 50%, preferably 80% of a total duration of the first and second periods of time; and finally, the multi-phase oral composition is removed from the at least one tooth.

Suitable Sources of Electromagnetic Radiation Include the Source Described Herein in the Section Titled "Clinical Protocol".

The multi-phase oral compositions as disclosed herein may be transparent or translucent to electromagnetic radiation with wavelengths from about 400 nm to about 500 nm. In certain embodiments, the multi-phase oral compositions as disclosed herein when applied in a thickness of from about 0.0001, 0.001, or 0.01 cm to about 0.01, 0.1, or 0.5 cm thick allow from about 10%, 20%, or 30% to about 40%, 50%, 60%, 70%, 80%, 90%, or 100% of electromagnetic radiation from about 400 nm to about 500 nm to pass through, as measured by a spectrophotometer. In certain embodiments, when a multi-phase oral composition is applied in a thickness of about 0.1 cm, from about 80% to about 100% of electromagnetic radiation from about 400 nm to about 500 nm passes through, as measured by a spectrophotometer. The multi-phase oral compositions, as disclosed herein, may when applied in an amount from about 0.0001, 0.001, or 0.01 grams to about 0.01, 0.1, 1, or 5 grams, on a delivery carrier or tray with a surface area from about 5 $cm^2$ to about 20 $cm^2$, allow from about 10%, 20%, or 30% to about 40%, 50%, 60%, 70%, 80%, 90%, or 100% of electromagnetic radiation from about 400 nm to about 500 nm to pass through.

The electromagnetic radiation impinging on the surface of the tooth or outer surface of the carrier, which may be a strip, in the wavelength range from about 400 to about 500 nm may range in intensity from about 5, 10, 25, 50, 75, or 100 $mW/cm^2$ to about 500, 250, 225, 205, 200, 175, 150, 125, 100, 75, 50, 25, 10, or 5 $mW/cm^2$ or any other numerical range, which is narrower and which falls within such broader numerical range, as if such narrower numerical ranges were all expressly written herein.

Procedure to Measure Intensity of Electromagnetic Radiation

The intensity of the electromagnetic radiation can be measured using a spectrometer (USB 2000+ from Ocean Optics) connected to a UV-VIS 200 micron fiber-optic cable with a cosine corrector at the tip (OP 200-2-UV-VIS from Ocean Optics). The spectrometer is connected to a computer running the spectrometer software (Oceanview 1.3.4 from Ocean Optics). The tip of the fiber-optic cable is held pointing toward the light source at the location where the light intensity is to be measured. The photons collected at the detector surface are guided via the fiber-optic cable to the charge-coupled device in the spectrometer (CCD). The CCD counts photons arriving to the CCD during a pre-determined time period at each wavelength from 200 nm to 1100 nm, and uses a software algorithm to convert these photon counts to spectral irradiance ($mW/cm^2/nm$). The spectral irradiance is integrated from 200 nm to 1100 nm by the software to yield the Absolute Irradiance (mW/cm$^2$), which is the intensity of electromagnetic radiation from 200 nm to 1100 nm. The spectral irradiance is integrated from 400 nm to 500 nm by the software to yield the Absolute Irradiance (mW/cm$^2$), which is the intensity of electromagnetic radiation from 400 nm to 500 nm.

For consumer convenience, the multi-phase oral composition as disclosed herein may be provided as a Kit comprising the bleaching composition as disclosed herein, a delivery carrier for easier application, an electromagnetic radiation source emitting electromagnetic radiation in a suitable wavelength, and instructions for use.

The compositions of this invention are useful for both human and other animals (e.g. pets, zoo, or domestic animals) applications.

EXAMPLES

The following non-limiting examples further describe preferred embodiments within the scope of the present invention. Many variations of these examples are possible without departing from the scope of the invention. All examples were performed at room temperature (RT) and atmospheric pressure unless stated otherwise.

These multi-phase oral compositions were made as described previously or below.

Specifically, 500 gram batches of Example-I-A and B, Example-II-A, B, and C, Comparative Example-I, and Example-III A, B, C, and D were made by weighing the aqueous solution of hydrogen peroxide ($H_2O_2$) and petrolatum into a Speedmixer container ("Max 300 Long Cup Translucent", item number 501 218t from Flacktek Inc., Landrum, SC), and mixing in a Speedmixer at 800 RPM for 5 seconds, 1200 RPM for 5 seconds, and 1950 RPM for 2 minutes. The walls of the container were then scraped down with a plastic spatula, and the contents were mixed a second time at 800 RPM for 5 seconds, 1200 RPM for 5 seconds, and 1950 RPM for 2 minutes. The walls of the container were then scraped down with a plastic spatula, and the contents were mixed a third time at 800 RPM for 5 seconds, 1200 RPM for 5 seconds, and 1950 RPM for 2 minutes.

Also, a 500 gram batch of Example-III E was made by first weighing the polyethylene and mineral oil into a Speedmixer container ("Max 300 Long Cup Translucent", item number 501 218t from Flacktek Inc., Landrum, SC), heating it in an oven set at 95° C. for about 3 hours, mixing with a spatula for about 30 seconds, followed by mixing in a Speedmixer at 800 RPM for 5 seconds, 1200 RPM for 5 seconds, and 1950 RPM for 2 minutes, and cooling overnight at room temperature. Next, the aqueous solution of $H_2O_2$ was added and mixed in a Speedmixer at 800 RPM for 5 seconds, 1200 RPM for 5 seconds, and 1950 RPM for 2 minutes. The walls of the container were then scraped down with a plastic spatula, and the contents were mixed a second time at 800 RPM for 5 seconds, 1200 RPM for 5 seconds, and 1950 RPM for 2 minutes. The walls of the container were then scraped down with a plastic spatula, and the contents were mixed a third time at 800 RPM for 5 seconds, 1200 RPM for 5 seconds, and 1950 RPM for 2 minutes.

Also, a 500 gram batch of Example-III F was made by first weighing the microcrystalline wax and mineral oil into a Speedmixer container ("Max 300 Long Cup Translucent", item number 501 218t from Flacktek Inc., Landrum, SC), heating it in an oven set at 95° C. for about 3 hours, mixing with a spatula for about 30 seconds, followed by mixing in a Speedmixer at 800 RPM for 30 seconds, and cooling overnight at room temperature. Next, the aqueous solution of $H_2O_2$ was added and mixed in a Speedmixer at 800 RPM for 5 seconds, 1200 RPM for 5 seconds, and 1950 RPM for 2 minutes. The walls of the container were then scraped down with a plastic spatula, and the contents were mixed a second time at 800 RPM for 5 seconds, 1200 RPM for 5 seconds, and 1950 RPM for 2 minutes. The walls of the container were then scraped down with a plastic spatula, and the contents were mixed a third time at 800 RPM for 5 seconds, 1200 RPM for 5 seconds, and 1950 RPM for 2 minutes.

Also, a batch of Example IV-A was made as follows: 242.6 g Petrolatum and 7.2 g of 35% aqueous Hydrogen Peroxide were added into a Max 300 Long Speedmixer container (Flacktek Inc., Landrum, SC) and mixed in a SpeedMixer DAC 400 FVZ (Flacktek Inc., Landrum, SC) for 30 seconds at 1600 rev/min. The mixture was transferred to an empty 12.8 oz Caulk Cartridge (McMaster Carr, Robbinsville, NJ) and stored in a refrigerator until the measured product temperature was 9° ° C. The Caulk Cartridge was inserted into a Pneumatic Caulk Gun (McMaster Carr, Robbinsville, NJ), and connected to the inlet of a Microfluidizer model M-110Y (Microfluidics, Westwood, MA 02090). The outlet piping of the Microfluidizer was arranged such that the product passed through only a F20Y Interaction Chamber and several cm of piping before and after. The inlet pressure to the Microfludizer was adjusted to 42 psig, and the inlet pressure to the Caulk Cartridge was adjusted to 94 psig. The final product was collected in a plastic container.

Also, a batch of Example IV-B was made as follows: 228.8 g Petrolatum and 21.6 g of 35% aqueous Hydrogen Peroxide were added into a Max 300 Long Speedmixer container (Flacktek Inc., Landrum, SC) and mixed in a SpeedMixer DAC 400 FVZ (Flacktek Inc., Landrum, SC) for 30 seconds at 1600 rev/min. The mixture was transferred to an empty 12.8 oz Caulk Cartridge (McMaster Carr, Robbinsville, NJ) and stored in a refrigerator until the measured product temperature was 8° C. The Caulk Cartridge was inserted into a Pneumatic Caulk Gun (McMaster Carr, Robbinsville, NJ), and connected to the inlet of a Microfluidizer model M-110Y (Microfluidics, Westwood, MA 02090). The outlet piping of the Microfluidizer was arranged such that the product passed through only a F20Y Interaction Chamber and several cm of piping before and after. The inlet pressure to the Microfludizer was adjusted to 42 psig, and the inlet pressure to the Caulk Cartridge was adjusted to 94 psig. The final product was collected in a plastic container.

Example I

Multi-Phase Oral Composition of Example I-A and B were Made Using the Procedure Described Above and Formulated with a 35% Aqueous Solution of Hydrogen Peroxide.

The following parameters were measured on Example-I-B using the procedures specified herein: a) two-dimensional density of droplets of aqueous phase of the multi-phase oral composition with a cross-sectional area larger than 10000 square microns per square centimeter of the two-dimensional plane; b) Standard deviation of the peroxide concentration of the multi-phase oral composition smeared on peroxide test strips; c) Mean peroxide concentration of the multi-phase oral composition smeared onto peroxide test strips.

|  | Example I | |
|---|---|---|
|  | A (Wt %) | B (Wt %) |
| 35% aqueous solution $H_2O_2$[1] | 0.2857 | 2.857 |
| Petrolatum[2] | 99.7143 | 97.143 |
| total | 100.00 | 100.00 |
| % $H_2O_2$ in total oral compos. | 0.099995 | 0.99995 |
| RATIO* | 350.02 | 35.002 |
| Two-dimensional density of droplets of aqueous phase with a cross-sectional area larger than 10000 square microns per square centimeter of the two-dimensional plane measured using the procedure specified herein |  | 10.3 |
| Standard deviation of the peroxide concentration of the multi-phase oral composition smeared on peroxide test strips measured using the procedure specified herein |  | 50.17 |
| Mean peroxide concentration of the multi-phase oral composition smeared onto peroxide test strips measured using the procedure specified herein |  | 47.55 |
| Ratio of the mean peroxide concentration of the multi-phase oral composition smeared onto peroxide test strips measured using the procedure specified herein to the standard deviation of the peroxide concentration of the multi-phase oral composition smeared on peroxide test strips measured using the procedure specified herein |  | 0.95 |

*RATIO of the concentration in weight percent of $H_2O_2$ present in the aqueous phase to the concentration in weight percent of $H_2O_2$ present in the overall composition
[1] ultra Cosmetic Grade from Solvay, Houston, Texas
[2] G-2191 Grade from Sonneborn, LLC., Parsippany, NJ

Example II

Multi-phase oral composition of Example II-A was made using the procedure described above and formulated with a 17.5% aqueous solution of hydrogen peroxide. Multi-phase oral compositions of Example II-B, and C were made using the procedure described above and formulated with a 5% aqueous solution of hydrogen peroxide.

|  | Example II | | |
|---|---|---|---|
|  | A (Wt %) | B (Wt %) | C (Wt %) |
| 17.5% aqueous sol. $H_2O_2$[3] | 0.5714 | 0.0000 | 0.0000 |
| 5% aqueous sol. $H_2O_2$[3] | 0.0000 | 1.0000 | 2.0000 |
| Petrolatum[4] | 99.4286 | 99.0000 | 98.0000 |
| total | 100.0 | 100.0 | 100.0 |
| % $H_2O_2$ in total compos. | 0.099995 | 0.0500 | 0.1000 |
| RATIO* | 175.01 | 100.00 | 50.00 |

*RATIO of the concentration in weight percent of $H_2O_2$ present in the aqueous phase to the concentration in weight percent of $H_2O_2$ present in the overall composition
[3] ultra Cosmetic Grade from Solvay (Houston, Texas) diluted with water
[4] G-2191 Grade from Sonneborn, LLC., Parsippany, NJ

Example III

Multi-phase oral compositions of Examples III were made using the procedure described above and formulated with 1) a 35% aqueous solution of hydrogen peroxide of different chemical grades as well as 2) different materials used as the hydrophobic phase.

| Example III | A (Wt %) | B (Wt %) | C (Wt %) | D (Wt %) | E (Wt %) | F (Wt %) |
|---|---|---|---|---|---|---|
| 35% aqueous sol. $H_2O_2$[5] | 0.2857 |  |  | 0.2857 | 0.2857 | 0.2857 |
| 35% aqueous sol. $H_2O_2$[6] |  | 0.2857 |  |  |  |  |
| 35% aqueous sol. $H_2O_2$[7] |  |  | 0.2857 |  |  |  |
| Petrolatum[8] |  | 99.7143 | 99.7143 |  |  |  |
| Petrolatum[9] | 99.7143 |  |  |  |  |  |
| Petrolatum[10] |  |  |  | 99.7143 |  |  |
| Mineral oil[11] |  |  |  |  | 79.7143 | 49.7143 |
| Polyethylene[12] |  |  |  |  |  | 20.00 |

-continued

| Example III | A (Wt %) | B (Wt %) | C (Wt %) | D (Wt %) | E (Wt %) | F (Wt %) |
|---|---|---|---|---|---|---|
| Microcrystalline Wax[13] | | | | | | 50.00 |
| total | 100.0 | 100.0 | 100.0 | 100.0 | 100.0 | 100.0 |
| % $H_2O_2$ in total compos. | 0.099995 | 0.099995 | 0.099995 | 0.099995 | 0.099995 | 0.099995 |
| RATIO* | 350.02 | 350.02 | 350.02 | 350.02 | 350.02 | 350.02 |

*RATIO of the concentration in weight percent of $H_2O_2$ present in the aqueous phase to the concentration in weight percent of $H_2O_2$ present in the overall composition
[5]ultra Cosmetic Grade from Solvay, Houston, Texas
[6]Technical Grade from Solvay, Houston, Texas
[7] Technical grade from Solvay Stabilized with added Stabilizers
[8]G-2191 Grade from Sonneborn, LLC., Parsippany, NJ
[9]G-1958 Grade from Sonneborn, LLC., Parsippany, NJ
[10]G-2218 Grade from Sonneborn, LLC., Parsippany, NJ
[11]Kaydol grade from Sonneborn, LLC., Parsippany, NJ
[12]400 Grade from Baker-Hughes, Houston, TX, dissolved into the mineral oil at about 95 C.
[13]W835 Grade from Sonneborn, LLC., Parsippany, NJ, dissolved into the mineral oil at about 95° C.

Example IV

Multi-phase oral compositions of Example IV-A, and B were made using the procedure described above and formulated with a 35% aqueous solution of hydrogen peroxide. The following parameters were measured on Examples IV-A, and IV-B using the procedures specified herein: a) two-dimensional density of droplets of aqueous phase of the multiphase oral composition with a cross-sectional area larger than 10000 square microns per square centimeter of the two-dimensional plane; b) Standard deviation of the peroxide concentration of the multi-phase oral composition smeared on peroxide test strips; c) Mean peroxide concentration of the multi-phase oral composition smeared onto peroxide test strips.

COMPARATIVE EXAMPLES

All examples were performed at room temperature (RT) and atmospheric pressure unless stated otherwise.

Comparative Example I

Comparative Example I was made using the procedure described above and formulated with no bleaching agent.

| Comparative Example I | (Wt %) |
|---|---|
| Petrolatum[14] | 100.0000 |
| total | 100.0000 |

| | Example IV | |
|---|---|---|
| | A (Wt %) | B (Wt %) |
| 35% aqueous solution $H_2O_2$[14] | 2.857 | 8.571 |
| Petrolatum[15] | 99.7143 | 91.429 |
| total | 100.00 | 100.00 |
| % $H_2O_2$ in total oral compos. | 0.99995 | 2.99985 |
| RATIO* | 35.02 | 11.67 |
| "Two-dimensional density of droplets" of aqueous phase with a cross-sectional area larger than 10000 square microns per square centimeter of the two-dimensional plane measured using the procedure specified herein | 0.1 | 2.95 |
| Standard deviation of the peroxide concentration of the multi-phase oral composition smeared onto peroxide test strips measured using the procedure specified herein | 5.15 | 12.39 |
| Mean peroxide concentration of the multi-phase oral composition smeared onto peroxide test strips measured using the procedure specified herein | 14.87 | 49.22 |
| Ratio of the mean peroxide concentration of the multi-phase oral composition smeared onto peroxide test strips measured using the procedure specified herein to the standard deviation of the peroxide concentration of the multi-phase oral composition smeared on peroxide test strips measured using the procedure specified herein | 2.89 | 3.97 |

*RATIO of the concentration in weight percent of $H_2O_2$ present in the aqueous phase to the concentration in weight percent of $H_2O_2$ present in the overall composition
[14]ultra Cosmetic Grade from Solvay, Houston, Texas
[15]G-2218 Grade from Sonneborn, LLC., Parsippany, NJ -continued

| Comparative Example I | (Wt %) |
|---|---|
| % $H_2O_2$ in total oral compos. | 0.0000 |

[14]G-2191 Grade from Sonneborn, LLC., Parsippany, NJ

Bleaching Efficacy of Example-IA Versus Comparative Example-I

The bleaching efficacy of Example-IA and Comparative Example-I were measured per the clinical protocol disclosed herein. Specifically, this was a randomized, single-center, two-treatment, parallel group, clinical study conducted on 39 adults who had never had a professional, over-the-counter or investigational tooth bleaching treatment. All participants were at least 18 years old, had all four measurable maxillary incisors, and had no self-reported tooth sensitivity. Participants were randomized to study treatments based on L* and b* color values and age. Participants were assigned to one of two treatment groups:

Example-IA (22 participants, mean L* of 74.1 and mean b* of 15.6) or

Comparative Example-I (17 participants, mean L* of 74.2 and mean b* of 15.2)

The maxillary anterior teeth of the participants were treated with the multi-phase oral composition they were assigned for 60 minutes once daily using a strip of polyethylene as a delivery carrier. The polyethylene strips were 66 mm×15 mm in size and 0.0178 mm thick. 0.6 grams to 0.8 grams of the multi-phase oral compositions were applied across each strip of polyethylene prior to applying to the maxillary anterior teeth.

Distribution of the assigned maxillary strips and all applications were supervised by a clinical site staff. For each treatment, participants wore a strip with the multi-phase oral composition they were assigned for a total of 60 minutes. After 50 minutes of each strip wear, a trained hygienist applied electromagnetic radiation toward the facial surfaces of the maxillary anterior teeth for 10 minutes. The electromagnetic radiation was directed toward the teeth through the strip and through the multi-phase oral composition. The electromagnetic radiation was delivered using the source of electromagnetic radiation described herein in the section titled "Clinical Protocol". The intensity of the electromagnetic radiation from 400 nm to 500 nm measured at the central axis of each cone of electromagnetic radiation exiting at the exit surface of the transparent window through which the electromagnetic radiation passes toward the maxillary anterior teeth was measured to be from about 175 mW/cm² to about 225 mW/cm² as measured by the procedure disclosed herein.

Digital Images were Collected at Baseline, and the Day after the $3^{rd}$, $7^{th}$, $10^{th}$, and $14^{th}$ Treatments.

The group using Example-IA demonstrated a statistically significant (p<0.0001), incremental reduction in yellowness (−Δb*) at all tested time-points relative to Baseline; in addition, increase in lightness (ΔL*) was observed in this group the day after seven, ten, and fourteen treatments (p<0.001).

The group using comparative Example-I did not differ from Baseline values after three, seven, and ten applications, and showed a small statistically significant (p=0.0007) decrease in yellowness (−Δb*) after fourteen treatments; no changes in lightness (ΔL*) were detected.

Furthermore, the group on Example-IA demonstrated a larger decrease in yellowness −Δb*) compared to the group on comparative Example-I at all tested time-points.

Table I shows the results in detail:

| Mean change in yellowness from baseline (Δb*) | Example-IA (0.099995% $H_2O_2$ delivered on a strip and used with an electromagnetic radiation source described herein in the section titled "Clinical Protocol") | Comparative Example-I (0% $H_2O_2$ delivered on same strip and used with same electromagnetic radiation source described herein in the section titled "Clinical Protocol") | % Improvement delivered by Example-IA over Comparative Example-I under same conditions |
|---|---|---|---|
| After 3 treatments (Day 4) | −0.607 | 0.073 | >800% |
| After 7 treatments (Day 8) | −1.45 | 0.005 | >800% |
| After 10 treatments (Day 11) | −1.70 | −0.191 | >800% |
| After 14 treatments (Day 15) | −1.95 | −0.408 | >400% |

These results clearly demonstrate the surprisingly high efficacy of Example-IA (delivered on a strip and used with electromagnetic radiation as disclosed herein) even though it has less than 0.1% $H_2O_2$.

The ratio of bleaching efficacy of Example-IA (delivered on a strip and used with electromagnetic radiation as disclosed herein), as measured per the clinical protocol as disclosed herein, and calculated as −Δb* to the weight percent of bleaching agent present in the overall multi-phase oral composition was 6.07, 14.5, 17.0, and 19.5 after 3, 7, 10, and 14 treatments respectively.

These results also clearly demonstrate the surprisingly high efficacy of Example-IA (delivered on a strip and used with electromagnetic radiation as disclosed herein) relative to the comparative Example-I (delivered on same strip and used with the same electromagnetic radiation source).

FIG. 7 shows images of example teeth treated with the bleaching multi-phase oral composition of Example IA. RGB images were converted to black-and-white images. Images were taken before and after 14 treatments with multi-phase oral composition of Example IA. Three teeth were shown, wherein the left side of the tooth shows its baseline visual appearance and the right side of the tooth shows its visual appearance after 14 treatments. It can be clearly seen that the treatment with Example IA multi-phase oral composition visibly whitens the tooth surface. All three teeth appear whiter on the right side compared to the left side.

It is also surprising that none of the study participants reported tooth-sensitivity despite experiencing the high efficacy of Example-IA (delivered on a strip and used with an electromagnetic radiation source as disclosed herein).

Comparative Example II

Comparative example II is a commercially available Crest Whitestrips tooth whitening strip product with 5.25% $H_2O_2$ (from Procter & Gamble, Cincinnati, OH, USA). This is an aqueous gel containing 5.25% hydrogen peroxide ($H_2O_2$); and since it is an aqueous gel, the ratio of the concentration in weight percent of $H_2O_2$ present in the aqueous phase to the concentration in weight percent of H2O2 present in the overall composition is 1.

Bleaching Efficacy of Comparative Example II (Aqueous Gel with 5.25% $H_2O_2$)

The bleaching efficacy of a second comparative composition (Comparative Example II—Crest Whitestrips tooth whitening strip product with 5.25% H2O2) containing a final concentration of 5.25% $H_2O_2$ in an aqueous gel measured in a clinical study. Specifically, the study for Comparative Example II was a controlled, single-center clinical trial. The target population was adult participants with no previous history of tooth whitening. Participants were treated with the above comparative aqueous gel with 5.25% $H_2O_2$ (Comparative Example II) delivered on a strip of polyethylene. The group (20 participants, mean L* of 72.8 and mean b* of 16.4) wore the strip for 60 minutes once daily for 14 days.

Digital images were obtained at Baseline, and the day after the 7th and 14th treatments. The results of the group who wore the comparative Example II (aqueous gel with 5.25% $H_2O_2$) delivered on a strip for 60 minutes (same length of time as Example-IA in the clinical described previously) are shown in the table below.

Table II shows the results in detail:

| Mean change in yellowness from baseline (Δb*) | Example-IA (composition of invention containing about 0.1% H2O2) (delivered on a strip for 60 minutes, and used with an electromagnetic radiation source described herein in the section titled "Clinical Protocol") | Comparative Example II (aqueous gel containing about 5.25% H2O2) (delivered on a strip for 60 minutes) |
|---|---|---|
| After 7 treatments (Day 8) | −1.45 | −0.985 |
| After 14 treatments (Day 15) | −1.95 | −1.43 |

After 7 treatments, the comparative Example II (aqueous gel with 5.25% $H_2O_2$, delivered on a strip for 60 minutes) produced a mean change in yellowness of −0.985 while Example-IA (also delivered on a strip, and used with an electromagnetic radiation source) delivered a mean change in yellowness of −1.45 even though it had approximately 5250% lower concentration of $H_2O_2$ vs. the aqueous gel (0.1% $H_2O_2$ Vs. 5.25% $H_2O_2$) used in Comparative Example II. Similarly after 14 treatments, the comparative Example II produced a mean change in yellowness of −1.43 while Example-IA delivered a mean change in yellowness of −1.95 even though it had approximately 5250% lower concentration of $H_2O_2$ Vs. the aqueous gel (0.1% $H_2O_2$ vs. 5.25% $H_2O_2$). It is worth noting from Table 1, that Comparative Example I which had the same electromagnetic radiation source disclosed herein but with 0.0% $H_2O_2$ delivered a mean change in yellowness of only 0.005 and −0.408 after 7 and 14 treatments respectively. These results also clearly demonstrate the surprisingly high efficacy of Example-IA (delivered on a strip and used with an electromagnetic radiation source as disclosed herein) even though it has approximately 5250% lower concentration of $H_2O_2$ Vs. the comparative aqueous gel (0.1% $H_2O_2$ Vs. 5.25% $H_2O_2$) used in Comparative Example II.

Also, it is worth noting that the ratio of the concentration in weight percent of bleaching agent present in the aqueous phase to the concentration in weight percent of bleaching agent present in the overall composition of the comparative example II is 1, while example IA has a ratio of 350.02.

The ratio of bleaching efficacy of Comparative Example II, calculated as −Δb* to the weight percent of bleaching agent present in the overall multi-phase oral composition was 0.19 and 0.27, after 7 and 14 treatments respectively. This is lower than the ratio of bleaching efficacy of Example-IA (delivered on a strip and used with an electromagnetic radiation source as disclosed herein), calculated as −Δb* to the weight percent of bleaching agent present in the overall multi-phase oral composition which was measured to be 14.5 and 19.5, after 7 and 14 treatments respectively.

Bleaching Efficacy of Example-IB

The bleaching efficacy of Example-IB was measured per the clinical protocol disclosed herein. Specifically, this was a single-center, single-treatment clinical study with 8 adults who had never had a professional, over-the-counter or investigational tooth bleaching treatment. All participants were at least 18 years old, had all four measurable maxillary incisors, and had no self-reported tooth sensitivity. Participants were assigned to the following treatment group:

Example-IB (8 participants, mean L* of 73.248 and mean b* of 16.368)

The maxillary anterior teeth of the participants were treated with the multi-phase oral composition Example-IB for 60 minutes once daily using a strip of polyethylene as a delivery carrier for three days. The polyethylene strips were 66 mm×15 mm in size and 0.0178 mm thick. 0.6 grams to 0.8 grams of the multi-phase oral composition was applied across each strip of polyethylene prior to applying to the maxillary anterior teeth.

Distribution of the maxillary strips and all applications were performed by a clinical site staff. Participants wore a strip with the multi-phase oral composition for a total of 60 minutes per treatment for three days. After 50 minutes of each strip wear, a trained hygienist applied electromagnetic radiation toward the facial surfaces of the maxillary anterior teeth for 10 minutes. The electromagnetic radiation was directed toward the teeth through the strip and through the multi-phase oral composition. The electromagnetic radiation was delivered using the source of electromagnetic radiation described herein in the section titled "Clinical Protocol". The intensity of the electromagnetic radiation from 400 nm to 500 nm measured at the central axis of each cone of electromagnetic radiation exiting at the exit surface of the transparent window through which the electromagnetic radiation passes toward the maxillary anterior teeth was measured to be from about 175 mW/cm$^2$ to about 225 mW/cm$^2$, as measured by the procedure disclosed herein.

Digital images were collected before the strips were applied on Day 1 (Baseline), Day 2, and Day 3; and after the strips were removed on Day 1, Day 2, and Day 3.

The participants demonstrated a statistically significant ($p<0.0001$) reduction in yellowness ($-\Delta b^*$) at all tested time-points relative to Baseline.

Table III shows the results in detail:

| Mean change in yellowness from baseline ($\Delta b^*$) | Example-IB (0.99995% $H_2O_2$ delivered on a strip and used with an electromagnetic radiation source described herein in the section titled "Clinical Protocol") |
|---|---|
| After 1 treatment (Day 1) | −1.604 |
| After 2 treatments (Day 2) | −1.996 |
| After 3 treatments (Day 3) | −2.931 |
| % of participants who reported or were observed to have oral irritation that was possibly or probably related to the product | 37.5 |
| % of participants who reported tooth sensitivity that was possibly or probably related to the product | 12.5 |
| % of participants who reported or were observed to have oral irritation or tooth sensitivity that was possibly or probably related to the product | 50 |
| Ratio of bleaching efficacy of the present invention, as measured per the clinical protocol as disclosed herein, and calculated as $-\Box b^*$ after 3 treatments to the fraction of participants who reported oral irritation or were observed to have oral irritation that was possibly or probably attributed to the composition tested | 7.816 |
| Ratio of bleaching efficacy of the present invention, as measured per the clinical protocol as disclosed herein, and calculated as $-\Box b^*$ after 3 treatments to the fraction of participants who reported tooth sensitivity that was possibly or probably attributed to the composition tested | 23.448 |
| Ratio of bleaching efficacy of the present invention, as measured per the clinical protocol as disclosed herein, and calculated as $-\Box b^*$ after 3 treatments to the fraction of participants who reported tooth sensitivity or reported oral irritation or were observed to have oral irritation that was possibly or probably attributed to the composition tested | 5.862 |

These results clearly demonstrate the surprisingly high efficacy of Example-IB (delivered on a strip and used with electromagnetic radiation, as disclosed herein) even though it has less than 1% $H_2O_2$. This is even more surprising since this high efficacy was delivered after just 1, 2 or 3 treatments. Furthermore, despite the high efficacy, surprisingly only 12.5% of the participants reported tooth sensitivity and even this was characterized as mild.

It is worth noting from table II that even after 7 treatments, comparative Example II (aqueous gel with 5.25% $H_2O_2$. delivered on a strip for 60 minutes) produced a mean change in yellowness of only −0.985 while Example-IB (also delivered on a strip, and used with an electromagnetic radiation source) delivered a mean change in yellowness of −2.931 after just 3 treatments even though it had approximately 525% lower concentration of $H_2O_2$ vs. the aqueous gel (0.99995% $H_2O_2$ Vs. 5.25% $H_2O_2$) used in Comparative Example II. It is also worth noting from table I that even after 7 treatments, comparative Example I which had the same electromagnetic radiation source disclosed herein, but with 0.0% $H_2O_2$ delivered a mean change in yellowness of only 0.005 while Example-IB (also delivered on a strip, and used with the same electromagnetic radiation source) delivered a mean change in yellowness of −2.931 after just 3 treatments. This further highlights the surprisingly high efficacy of Example-IB.

Bleaching Efficacy of Examples IV-A and IV-B

The bleaching efficacy of Examples IV-A and IV-B were measured per the clinical protocol disclosed herein. Specifically, this was a randomized, single-center, two-treatment, parallel group, clinical study with 23 adults who had never had a professional, over-the-counter or investigational tooth bleaching treatment. All participants were at least 18 years old, had all four measurable maxillary incisors, and had no self-reported tooth sensitivity. Participants were randomized to study treatments based on L* and b* color values and age. Participants were assigned to one of two treatment groups:

Example-IV-A (11 participants, mean L* of 70.342 and mean b* of 16.669) or

Example-IV-B (12 participants, mean L* 72.146 and mean b* of 17.170)

The maxillary anterior teeth of the participants were treated with the assigned multi-phase oral composition for 60 minutes once daily using a strip of polyethylene as a delivery carrier for three days. The polyethylene strips were 66 mm×15 mm in size and 0.0178 mm thick. 0.6 grams to 0.8 grams of the multi-phase oral composition was applied across each strip of polyethylene prior to applying to the maxillary anterior teeth.

Distribution of the maxillary strips and all applications were performed by a clinical site staff. Participants wore the strip with the multi-phase oral composition for a total of 60 minutes each day for three days. After 50 minutes of each strip wear, a trained hygienist applied electromagnetic radiation toward the facial surfaces of the maxillary anterior teeth for 10 minutes. The electromagnetic radiation was directed toward the teeth through the strip and through the multi-phase oral composition. The electromagnetic radiation was delivered using the source of electromagnetic radiation described herein in the section titled "Clinical Protocol". The intensity of the electromagnetic radiation from 400 nm to 500 nm measured at the central axis of each cone of electromagnetic radiation exiting at the exit surface of the transparent window, through which the electromagnetic radiation passes toward the maxillary anterior teeth was measured to be from about 175 mW/cm$^2$ to about 225 mW/cm$^2$ as measured by the procedure disclosed herein.

Digital images were collected before the strips were applied on Day 1 (Baseline), Day 2, and Day 3; and after the strips were removed on Day 1, Day 2, and Day 3.

The participants demonstrated a statistically significant ($p<0.0001$) reduction in yellowness ($-\Delta b^*$) at all tested time-points relative to Baseline.

Table IV shows the results in detail:

| | Example-IV-A (0.99995% $H_2O_2$ delivered on a strip and used with an electromagnetic radiation source described herein in the section titled "Clinical Protocol") | Example-IV-B (2.99985% $H_2O_2$ delivered on a strip and used with an electromagnetic radiation source described herein in the section titled "Clinical Protocol") |
|---|---|---|
| Mean change in yellowness from baseline ($\Delta b^*$) after 1 treatment (Day 1) | −1.294 | −1.778 |
| Mean change in yellowness from baseline ($\Delta b^*$) after 2 treatments (Day 2) | −1.946 | −2.286 |
| Mean change in yellowness from baseline ($\Delta b^*$) after 3 treatments (Day 3) | −2.086 | −3.204 |
| % of participants who reported or were observed to have oral irritation that was possibly or probably related to the product | 9.1 | 16.7 |
| % of participants who reported tooth sensitivity that was possibly or probably related to the product | 0 | 16.7 |
| % of participants who reported or were observed to have oral irritation or tooth sensitivity that was possibly or probably related to the product | 9.1 | 33.3 |
| Ratio of bleaching efficacy of the present invention, as measured per the clinical protocol as disclosed herein, and calculated as $-\Delta b^*$ after 3 treatments to the fraction of participants who reported oral irritation or were observed to have oral irritation that was possibly or probably attributed to the composition tested | 22.923 | 19.186 |
| Ratio of bleaching efficacy of the present invention, as measured per the clinical protocol as disclosed herein, and calculated as $-\Delta b^*$ after 3 treatments to the fraction of participants who reported tooth sensitivity that was possibly or probably attributed to the composition tested | >100 | 19.186 |
| Ratio of bleaching efficacy of the present invention, as measured per the clinical protocol as disclosed herein, and calculated as $-\Delta b^*$ after 3 treatments to the fraction of participants who reported sensitivity or reported oral irritation or were observed to have oral irritation that was possibly or probably attributed to the composition tested | 22.923 | 9.622 |

These results clearly demonstrate the surprisingly high efficacy and low level of oral irritation and tooth sensitivity of Examples-IV-A (delivered on a strip and used with electromagnetic radiation as disclosed herein). This is even more surprising since this high efficacy was delivered after just 1, 2 or 3 treatments even though it had only about 0.99995% $H_2O_2$.

As before, it is worth noting from table II that even after 7 treatments, comparative Example II (aqueous gel with 5.25% $H_2O_2$, delivered on a strip for 60 minutes) produced a mean change in yellowness of only −0.985 while Example-IV-A (also delivered on a strip, and used with an electromagnetic radiation source) delivered a mean change in yellowness of −2.086 after just 3 treatments even though it had approximately 525% lower concentration of $H_2O_2$ vs. the aqueous gel (0.99995% $H_2O_2$ Vs. 5.25% $H_2O_2$) used in Comparative Example II. It is also worth noting from Table I that even after 7 treatments comparative Example I, which had the same electromagnetic radiation source disclosed herein, but with 0.0% $H_2O_2$ delivered a mean change in yellowness of only 0.005 while Example-IV-A (also delivered on a strip, and used with the same electromagnetic radiation source) delivered a mean change in yellowness of −2.086 after just 3 treatments. This further highlights the surprisingly high efficacy of Example-IV-A.

Combining the observation that: 1) Example I-B delivered a mean decrease in yellowness (−Δb*) of 2.931 after three treatments while Example IV-A delivered a mean decrease in yellowness (−Δb*) of 2.086 after three treatments with the observation that; 2) the mean peroxide concentration of the multi-phase oral composition smeared on peroxide test strips measured using the procedure specified herein is also higher for Example I-B Vs. IV-A (47.55 Vs. 14.87) despite both examples having the same level of H2O2 (about 0.99995%) shows that bleaching efficacy, as measured by the mean decrease in yellowness (−Δb*), increases as the mean peroxide concentration of the multi-phase oral composition smeared on peroxide test strips measured using the procedure specified herein increases.

Furthermore, despite the high efficacy of Example-IV-A, surprisingly only 9.1% of the participants reported or were observed to have oral irritation, 0% of the participants reported tooth sensitivity, and only 9.1% of the participants were observed to have or to have oral irritation or tooth sensitivity that was possibly or probably related to the product and even these were characterized as mild.

Combining the observation that: 1) only 9.1% of participants reported or were observed to have oral irritation and 0% of participants reported tooth sensitivity when treated with Example IV-A, while 37.5% of participants reported or were observed to have oral irritation and 12.5% of participants reported tooth sensitivity when treated with Example I-B with the observation that; 2) the two-dimensional density of droplets of aqueous phase with a cross-sectional area larger than 10000 square microns per square centimeter of the two-dimensional plane measured using the procedure specified herein was also lower for Example IV-A Vs. I-B (0.1 Vs. 10.3) despite both examples having the same level of $H_2O_2$ (about 0.99995%%) shows that oral irritation and tooth sensitivity decrease as two-dimensional density of droplets of aqueous phase with a cross-sectional area larger than 10000 square microns per square centimeter of the two-dimensional plane measured using the procedure specified herein decreases.

Combining the observation that: 1) only 9.1% of participants reported or were observed to have oral irritation and 0% of participants reported tooth sensitivity when treated with Example IV-A while 37.5% of participants reported or were observed to have oral irritation and 12.5% of participants reported tooth sensitivity when treated with Example I-B with the observation that; 2) the standard deviation of the peroxide concentration of the multi-phase oral composition smeared on peroxide test strips measured using the procedure specified herein was also lower for Example IV-A Vs. I-B (5.15 Vs. 50.17), despite both examples having the same level of $H_2O_2$ (about 0.99995%), shows that oral irritation and tooth sensitivity decrease as the standard deviation of the peroxide concentration of the multi-phase oral composition smeared on peroxide test strips measured using the procedure specified herein decreases.

Further, combining the observation that: 1) the ratio of the bleaching efficacy to the fraction of participants who reported oral irritation or were observed to have oral irritation was 22.923 for Example IV-A and only 7.816 for Example I-B with the observation that 2) the ratio of the mean peroxide concentration of the multi-phase oral composition smeared onto peroxide test strips to the standard deviation of the peroxide concentration of the multi-phase oral composition smeared onto peroxide test strips was also higher for Example IV-A Vs. Example I-B (2.89 Vs. 0.95), even though both examples had the same level of bleaching agent (about 1%), shows that the ratio of the bleaching efficacy to the fraction of participants who reported oral irritation or were observed to have oral irritation decreases as the ratio of the mean peroxide concentration of the multi-phase oral composition smeared onto peroxide test strips to the standard deviation of the peroxide concentration of the multi-phase oral composition smeared on peroxide test strips decreases.

Combining the observation that: 1) the ratio of the bleaching efficacy to the fraction of participants who reported tooth sensitivity was >100 for Example IV-A and only 23.448 for Example I-B with the observation that; 2) the ratio of the mean peroxide concentration of the multi-phase oral composition smeared onto peroxide test strips to the standard deviation of the peroxide concentration of the multi-phase oral composition smeared on peroxide test strips was also higher for Example IV-A Vs. Example I-B (2.89 Vs. 0.95), even though both examples had the same level of bleaching agent (about 1%), shows that the ratio of the bleaching efficacy to the fraction of participants who reported tooth sensitivity decreases as the ratio of the mean peroxide concentration of the multi-phase oral composition smeared onto peroxide test strips to the standard deviation of the peroxide concentration of the multi-phase oral composition smeared on peroxide test strips decreases.

Further, combining the observation that: 1) the ratio of the bleaching efficacy to the fraction of participants who reported tooth irritation or reported oral irritation or were observed to have oral irritation was 22.923 for Example IV-A and only 5.862 for Example I-B with the observation that; 2) the ratio of the mean peroxide concentration of the multi-phase oral composition smeared onto peroxide test strips to the standard deviation of the peroxide concentration of the multi-phase oral composition smeared on peroxide test strips was also higher for Example IV-A Vs. Example I-B (2.89 Vs. 0.95), even though both examples had the same level of bleaching agent (about 1%), shows that the ratio of the bleaching efficacy to the fraction of participants who reported tooth irritation or reported oral irritation or were observed to have oral irritation decreases as the ratio of the mean peroxide concentration of the multi-phase oral composition smeared onto peroxide test strips to the standard deviation of the peroxide concentration of the multi-phase oral composition smeared on peroxide test strips decreases.

The above clinical results also show that Example IV-B delivered very high efficacy as measured by the mean decrease in yellowness (−Δb*) of 3.204, while having low oral irritation (only 16.7%), low tooth sensitivity (only 16.7%), and low oral irritation or tooth sensitivity (only 33.3%).

Comparative Example III

Comparative example III is a tooth whitening strip product with 14% $H_2O_2$ (from Procter & Gamble, Cincinnati, OH, USA). This is an aqueous gel containing 14% hydrogen peroxide ($H_2O_2$)

Bleaching Efficacy of Comparative Example III (Aqueous Gel with 14% $H_2O_2$)

The bleaching efficacy of a third comparative composition (Comparative Example III—tooth whitening strip product with 14% H2O2) containing a final concentration of 14% $H_2O_2$ in an aqueous gel was measured as a part of five different clinical studies. The target populations were adult participants with no previous history of tooth whitening. Participants were treated with the above comparative aqueous gel with 14% $H_2O_2$ (Comparative Example III) delivered on a strip of polyethylene. All five separate groups (totaling over 100 participants) wore the strip for 30 minutes twice daily for 21 days.

Digital images were obtained at Baseline, and the day after the 21$^{st}$ treatment day. The combined results of all five clinical studies on the participants who wore the comparative Example III (aqueous gel with 14% $H_2O_2$) delivered on a strip for 30 minutes twice daily for 21 days are shown in the table below.

Table V shows the results in detail:

in yellowness of −3.09 while Example-IV-B (also delivered on a strip, and used with an electromagnetic radiation source) delivered a mean change in yellowness of −3.204 even though it had approximately 466% lower concentration of $H_2O_2$ vs. the aqueous gel (2.99985% $H_2O_2$ Vs. 14% $H_2O_2$) used in Comparative Example III. These results show the surprisingly high efficacy of Example IV-B especially since it was it was treated for only 3 days (once daily) while Comparative Example III was treated for 21 days (twice daily).

Furthermore, Comparative Example III delivered a high efficacy (−Δb* of 3.09), but also had high oral irritation (29.6%), high tooth sensitivity (38.3%), and high oral irritation or tooth sensitivity (58.3%). In contrast, Example IV-B also delivered high efficacy (−Δb* of −3.204) while having low oral irritation (only 16.7%), low tooth sensitivity (only 16.7%), and low oral irritation or tooth sensitivity (only 33.3%). These clinical results highlight the surprisingly high efficacy combined with the surprisingly low oral irritation and tooth sensitivity of Example IV-B.

The ratio of bleaching efficacy (−□b*) to the fraction of participants who reported oral irritation or were observed to have oral irritation was 19.186 for Example IV-B and 22.923 for Example IV-A Vs. only 10.439 for Comparative Example III. Similarly, the ratio of bleaching efficacy

|  | Comparative Example III (14% $H_2O_2$ aqueous gel delivered on a strip) | Example-IV-B (2.99985% $H_2O_2$ delivered on a strip and used with an electromagnetic radiation source described herein in the section titled "Clinical Protocol") |
|---|---|---|
| Treatment time | 30 minutes twice daily | 60 minutes once daily |
| Number of treatments days | 21 | 3 |
| Mean change in yellowness from baseline (Δb*) | −3.09 | −3.204 |
| % of participants who reported or were observed to have oral irritation that was possibly or probably related to the product | 29.6 | 16.7 |
| % of participants who reported tooth sensitivity that was possibly or probably related to the product | 38.3 | 16.7 |
| % of participants who reported or were observed to have oral irritation or tooth sensitivity that was possibly or probably related to the product | 58.3 | 33.3 |
| Ratio of bleaching efficacy (−□b*) to the fraction of participants who reported oral irritation or were observed to have oral irritation that was possibly or probably attributed to the composition tested | 10.439 | 19.186 |
| Ratio of bleaching efficacy (−□b*) to the fraction of participants who reported tooth sensitivity that was possibly or probably attributed to the composition tested | 8.067 | 19.186 |
| Ratio of bleaching efficacy (−□b*) to the fraction of participants who reported tooth sensitivity or reported oral irritation or were observed to have oral irritation that was possibly or probably attributed to the composition tested | 5.300 | 9.622 |

Comparative Example III (aqueous gel with 14% $H_2O_2$, delivered on a strip for 60 minutes) produced a mean change (−□b*) to the fraction of participants who reported tooth sensitivity was 19.186 for example IV-B and >100 for Example IV-A Vs. only 8.067 for comparative Example III. Similarly, the ratio of bleaching efficacy (−□b*) to the fraction of participants who reported tooth sensitivity or reported oral irritation or were observed to have oral irritation was 9.622 for Example IV-B and 22.923 for Example IV-A Vs. only 5.300 for Comparative Example III. These data highlight the surprisingly high ratio of bleaching efficacy to tooth sensitivity and/or oral irritation delivered by Examples IV-B and IV-A.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A kit comprising:
   a) a multi-phase oral composition for whitening teeth, the multi-phase oral composition comprising:
      i) from about 0.002% to about 30%, by weight of the multi-phase oral composition, of a discontinuous aqueous phase comprising up to 10%, by weight of the multi-phase oral composition, of a bleaching agent; and
      ii) a continuous hydrophobic phase comprising at least about 50%, by weight of the multi-phase oral composition, of petrolatum,
      wherein the multi-phase oral composition is a water-in-oil emulsion; and
   b) a delivery carrier.

2. The kit of claim 1, wherein the delivery carrier is a dental tray.

3. The kit of claim 1, wherein the delivery carrier is a strip, wherein the strip is deformable and made of plastic or wax.

4. The kit of claim 1, wherein the delivery carrier is a brush tip applicator.

5. The kit of claim 1, wherein a ratio of a concentration in weight percent of bleaching agent present in the aqueous phase to a concentration in weight percent of bleaching agent present in the multi-phase oral composition is at least about 10.

6. The kit of claim 5, wherein the ratio is at least about 50.

7. The kit of claim 1, wherein an amount of the bleaching agent ranges from about 0.01% to about 0.03%, by weight of the multi-phase oral composition.

8. The kit of claim 1, wherein an amount of the bleaching agent ranges from about 0.1% to about 5%, by weight of the multi-phase oral composition.

9. The kit of claim 1, wherein a two-dimensional density of droplets with a cross-sectional area larger than about 10000 square microns is no more than about 20 per square centimeter.

10. The kit of claim 9, wherein the two-dimensional density of droplets with a cross-sectional area larger than about 10000 square microns is no more than about 10 per square centimeter.

11. The kit of claim 1, wherein the bleaching agent is a peroxide bleaching agent, and wherein a standard deviation of a peroxide concentration of the multi-phase oral composition smeared onto peroxide test strips is no more than about 50.

12. The kit of claim 1, wherein the bleaching agent is a peroxide bleaching agent, and wherein a mean residual peroxide concentration of the multi-phase oral composition smeared onto peroxide test strips is from about 1 to about 100.

13. The kit of claim 1, wherein the bleaching agent in the multi-phase oral composition comprises hydrogen peroxide.

14. The kit of claim 1, wherein a bleaching efficacy of the multi-phase oral composition calculated as −Δb* is at least about 1.5.

15. The kit of claim 1, wherein a ratio of a bleaching efficacy of the multi-phase oral composition calculated as −Δb* to a weight percentage of the bleaching agent present in the multi-phase oral composition is at least about 1.5.

16. The kit of claim 1, wherein the discontinuous aqueous phase is dispersed as droplets within the continuous hydrophobic phase.

17. The kit of claim 1, wherein the multi-phase oral composition comprises from greater than 0% to about 0.5%, by weight of the multi-phase oral composition, of emulsifier.

18. A method of using the kit of claim 1, the method comprising:
   applying the multi-phase oral composition to one or more teeth using the delivery carrier;
   maintaining the multi-phase oral composition on the one or more teeth for a first period of time without directing radiation toward the one or more teeth; and
   activating an electromagnetic radiation source after the first period of time to direct electromagnetic radiation toward the one or more teeth for a second period of time, wherein the electromagnetic radiation source is capable of directing electromagnetic radiation with one or more wavelength in a range from about 200 nm to about 1700 nm toward at least one tooth, wherein the electromagnetic radiation source emits the electromagnetic radiation in a range from about 75 mW/cm$^2$ to about 250 mW/cm$^2$.

19. The method of claim 18, further comprising removing the multi-phase oral composition from the one or more teeth after activating the electromagnetic radiation source.

20. The method of claim 18, further comprising removing the multi-phase oral composition from the one or more teeth before activating the electromagnetic radiation source.

* * * * *